(12) United States Patent
Hey-Hawkins et al.

(10) Patent No.: US 10,774,097 B2
(45) Date of Patent: Sep. 15, 2020

(54) BORON COMPOUNDS AS INHIBITORS OF LIPOXYGENASE AND THE LIPOXYGENASE PATHWAY, AND PREPARATION AND USE THEREOF

(71) Applicant: UNIVERSITÄT LEIPZIG, Leipzig (DE)

(72) Inventors: Evamarie Hey-Hawkins, Polent (DE); Robert Kuhnert, Flöha (DE)

(73) Assignee: UNIVERSITÄT LEIPZIG, Leipzig (DE)

( * ) Notice: Subject to any disclaimer, the term of this patent is extended or adjusted under 35 U.S.C. 154(b) by 0 days.

(21) Appl. No.: 15/770,477

(22) PCT Filed: Oct. 21, 2016

(86) PCT No.: PCT/EP2016/075419
§ 371 (c)(1),
(2) Date: Apr. 23, 2018

(87) PCT Pub. No.: WO2017/068145
PCT Pub. Date: Apr. 27, 2017

(65) Prior Publication Data
US 2019/0055268 A1 Feb. 21, 2019

(30) Foreign Application Priority Data

Oct. 22, 2015 (DE) .......................... 10 2015 220 700

(51) Int. Cl.
| C07F 5/02 | (2006.01) |
| A61P 25/28 | (2006.01) |
| A61P 37/08 | (2006.01) |

(52) U.S. Cl.
CPC .............. *C07F 5/027* (2013.01); *A61P 25/28* (2018.01); *A61P 37/08* (2018.01)

(58) Field of Classification Search
CPC ........................................................ C07F 5/02
See application file for complete search history.

(56) References Cited

U.S. PATENT DOCUMENTS 4,794,188 A 12/1988 Musser et al.
2018/0264017 A1* 9/2018 Tjarks .................... A61K 45/06

FOREIGN PATENT DOCUMENTS

| CA | 2348853 A1 | 11/2002 |
| WO | 2006/073938 A2 | 7/2006 |
| WO | 2008/145733 A2 | 12/2008 |

OTHER PUBLICATIONS

Kreienbrink, A. et al. Chemical Communications 51(5), 836-838 (2015). (Year: 2015).*

International Search Report, European Patent Office Acting as International Searching Authority, issued in counterpart International Application No. PCT/EP2016/075419, dated Nov. 23, 2016.
German Patent Office, Search Report issued in German Counterpart Application No. DE 10 2015 220 700.5, dated Jun. 21, 2016.
Teixidor et al., "The First Optically Pure nido-Monothiocarborane Cluster," Organometallics, 18:5409-5411 (1999).
Boehnke et al., "Facile Synthesis of the Versatile Trifunctionalized Building Block 1,2-bis(hydroxymethyl)-9-mercapto-1,2-dicarba-close-dodecaborane(12)," Biochemical and Biophysical Journal of Neutron Therapy & Cancer Treatments, 1(1):22-27 (2013).
Neumann et al., "Reduction of Hydroxy-Functionalised Carbaboranyl Carboxylic Acids and Ketones by Organolithium Reagents," Dalton Transactions, 44:6638-6644 (2015).
Neumann et al., "Reduction of Hydroxy-Functionalised Carbaboranyl Carboxylic Acids to Tertiary Alcohols by Organolithium Reagents," Dalton Transactions, 43:4935-4937 (2014).
Mano et al., "Novel Imidazole Compounds as a New Series of Potent, Orally Active Inhibitors of 5-Lipoxygenase," Bioorg. Med. Chem., 11:3879-3887 (2003).
Lesnikowski, Z.J., "Boron Units as Pharmacophors—New Applications and Opportunities of Boron Cluster Chemistry," Collect. Czech. Chem. Commun., 72:1646-1658 (2007).
Koo et al., "Synthesis and Comparative Toxicology of a Series of Polyhedral Borane Anion-Substituted Tetraphenyl Porphyrins," J. Med. Chem., 50:820-827 (2007).
Beer et al., "Preparation and Evaluation of Carborane Analogues of Tamoxifen," J. Med. Chem., 53:8012-8020 (2010).

* cited by examiner

*Primary Examiner* — Joseph R Kosack
(74) *Attorney, Agent, or Firm* — FisherBroyles, LLP; Andrew K. Gonsalves, Esq.

(57) ABSTRACT

The invention relates to chemical compound of the general structure

[A-R₃—X—R₄]

where
A=[R₁-R₂] or [R₁]
R₁=aryl, heteroaryl
R₂=alkyl, aryl, heteroaryl, carbonyl, thiocarbonyl, alkyl ester, alkyl thioester
R₃=O, S, NH
X=closo- or nido-boron cluster
R₄=

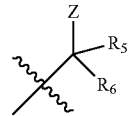

where Z=OH, SH, NH₂
where R₅ is selected from H, alkyl, aryl, heteroaryl, alkyl ether, alkyl thioether, alkylamine
and R₆ is selected from alkyl, aryl, heteroaryl, alkyl ether, alkyl thioether, alkylamine
and where R₃ and R₄ are in meta or para positions to one another,
to a process for preparation thereof and to the use thereof, especially in medicine, for example in the inhibition of lipoxygenase.

12 Claims, 7 Drawing Sheets

BORON COMPOUNDS AS INHIBITORS OF LIPOXYGENASE AND THE LIPOXYGENASE PATHWAY, AND PREPARATION AND USE THEREOF

FIELD OF THE DISCLOSURE

The invention relates to novel, boron-containing chemical compounds, to a method for preparing said compounds and to the use thereof in medicine, but also for catalysts or other materials.

BACKGROUND

Lipoxygenases are a class of enzymes which are involved in the metabolism of arachidonic acid. Said acid is converted to biologically active leukotrienes, which are involved in inflammatory reactions. Lipoxygenases therefore play a role, for example, in asthma and some cancers as they are overexpressed by some tumours. The subsequent inflammatory reaction causes new blood vessels to form (angiogenesis) such that the tumour is able to build up an independent blood supply and generate metastases.

Inhibiting lipoxygenase is therefore of central importance for suppressing the breakdown of arachidonic acid and for minimising the subsequent inflammatory reactions.

The inhibition of 5-lipoxygenase, also referred to as 5-LO or 5-LOX, is of particular importance.

There are currently only a few drugs on the market which inhibit lipoxygenase. Many previous candidates from clinical studies failed due to excessively low bioavailability and high metabolic breakdown and an associated low level of in vivo activity.

As described in a publication by Mano et al. [T. Mano, K. Mlyamoto, Bioorg. Med. Chem., 2003, 11, 3,879-3,887], experiments with imidazole derivatives have already been carried out in order to improve the solubility behaviour of 5-LOX inhibitors. However, the syntheses for these derivatives are very complex, thus making them very expensive to prepare. At the same time, some of the compounds lose a great deal of their effectiveness within the organism as they are metabolically extremely unstable.

It is known that dicarba-closododecaboranes (also carbaboranes or carboranes, $C_2B_{10}H_{12}$) are non-toxic [M. S. Koo, S. B. Kahl, J. Med. Chem., 2007, 50, 820-827] and chemically and metabolically extremely stable compounds [Z. J. Lesnikowski, Collect. Czech. Chem. Commun., 2007, 72, 1,646-1,658]. Furthermore, it has already been demonstrated that the use of carboranes in drugs may lead to increased metabolic stability [M. L. Beer, J. Lemon, J. F. Valliant, J. Med. Chem., 2010, 53, 8,012-8,020; J. F. Valliant, P. Schaffer, K. Stephenson, CA 2348853 A1].

CA 2348853 A1 discloses a compound, an analogue of tamoxifen, in which one of the three phenyl rings is replaced by a carborane cluster, the cluster having a mono-functionalisation. The cluster analogue demonstrates pharmacological activity for breast cancer therapy and can be used, inter alia, in boron neuron capture therapy (BNCT).

WO 2008/145733 describes, inter alia, the substitution of aromatic ring structures within particular compounds by boron-containing clusters, preferably carboranes, in order to thus achieve improved pharmaceutical properties. Disclosed is a method for preparing ortho-substituted carboranes which assume the position of ortho-substituted phenyl rings within known compounds, such as salicylic acid. However, the drawback to these ortho-carboranes is that they have high metabolic instability and restricted effectiveness. The mentioned compounds are intended to be used for improved inhibition of cyclooxygenase; however, inhibition tests on the enzyme or cytotoxicity tests have not been carried out and demonstrated. No evidence has been provided for the effectiveness of the substances either. Meta- and para-carboranyl compounds are cited as carboxylic acids and carboxylic acid chlorides known in the literature; however, these compounds have no structural similarity to inhibitors or precursors of inhibitors of lipoxygenase or the lipoxygenase pathway. The subsequent conversion to compounds having LOX-inhibiting properties was not sought after or investigated in WO 2008/145733.

WO 20061073938 describes, inter alia, the use of boron clusters which are mono-functionalised, i.e. only substituted at one position, for substituting indolizine rings in compounds which, as anti-bacterial, inflammation-inhibiting and anti-viral compounds, are intended to be effective in particular against HIV.

The drawback to mono-functionalised clusters is that they have only insufficient cytotoxicity towards various cancer cell lines.

Publications by W. Neumann et al. illustrate the introduction of tertiary alcohol substituents on the carborane frame which are in ortho positions in relation to already present substituents. In this case, a carboxylic acid unit introduced on the carborane frame is reduced/alkylated two-fold by means of alkyl lithium. [W. Neumann, Dalton Trans., 2014, 43, 4,935-4,937; W. Neumann, Dalton Trans., 2015, 44, 6,638-6,644]. The drawback is that only ortho-substituted carborane frames can be generated on this pathway. No primary or secondary alcohols can be generated in this way either, which considerably restricts the applicability of the synthesis. The subsequent conversion to compounds having LOX-Inhibiting properties was not investigated in the publications.

BRIEF DESCRIPTION OF THE DRAWINGS

In FIG. 1, the enzyme activity values are plotted with respect to the concentration of the inhibitors from embodiment 3 (symbol: ●) and 5 (symbol: ▲) and inhibitor Rev-5901 (symbol: ■).

In FIG. 2, the enzyme activity values are plotted with respect to the concentration of the inhibitors from embodiment 8 (symbol: ▲) and 9 (symbol: ▼).

In FIG. 3, the enzyme activity values are plotted with respect to the concentration of the inhibitors from comparative example 1 (symbol: ■) and 2 (symbol: ●).

DETAILED DESCRIPTION

The object of the invention is to provide novel chemical compounds which have improved pharmacokinetic properties and may be used to inhibit lipoxygenases. Said compounds are intended to be used in particular in medicine as pharmacophores or drugs, but also for catalysts or other materials.

The object is achieved by compounds of the general structure

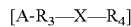

where
A=[$R_1$-$R_2$] or [$R_1$]
$R_1$=aryl, heteroaryl
$R_2$=alkyl, aryl, heteroaryl, carbonyl, thiocarbonyl, alkyl ester, alkyl thioester
$R_3$=O, S, NH
X=closo- or nido-boron cluster
$R_4$=

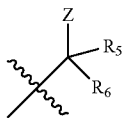

where Z=OH, SH, $NH_2$
where $R_5$ is selected from H, alkyl, aryl, heteroaryl, alkyl ether, alkyl thioether, alkylamine
and $R_6$ is selected from alkyl, aryl, heteroaryl, alkyl ether, alkyl thioether, alkylamine
and where $R_3$ and $R_4$ are in meta or para positions in relation to one another.

These compounds are derived from basic structures or lead structures which already have inhibiting effects on lipoxygenase, for example naphthyl and quinoline derivatives such as Rev-5901, MK-0591, L-674 or ICI-211965 or phenyl tetrahydropyran derivatives, such as ZD2138 or CJ-13610. What all these compounds have in common is that they have a central aromatic ring system, e.g. a phenyl ring, which can be replaced by a, preferably boron-containing, cluster.

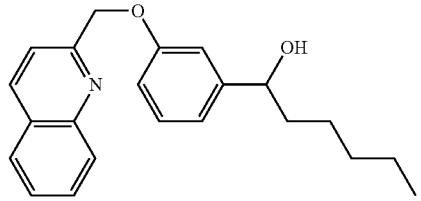

Rev-5901

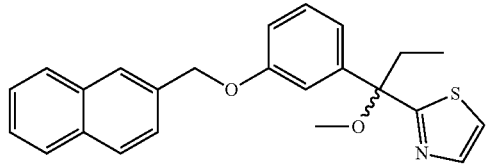

ICI-211965

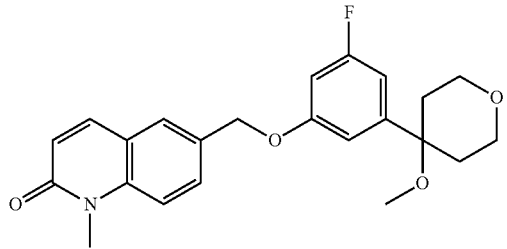

ZD2138

The invention is based on the idea that this central, sterically demanding, aromatic group is replaced by a cluster. All the compounds according to the invention have an in principle similar composition, which corresponds in general to the structure

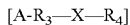

Figure 4:
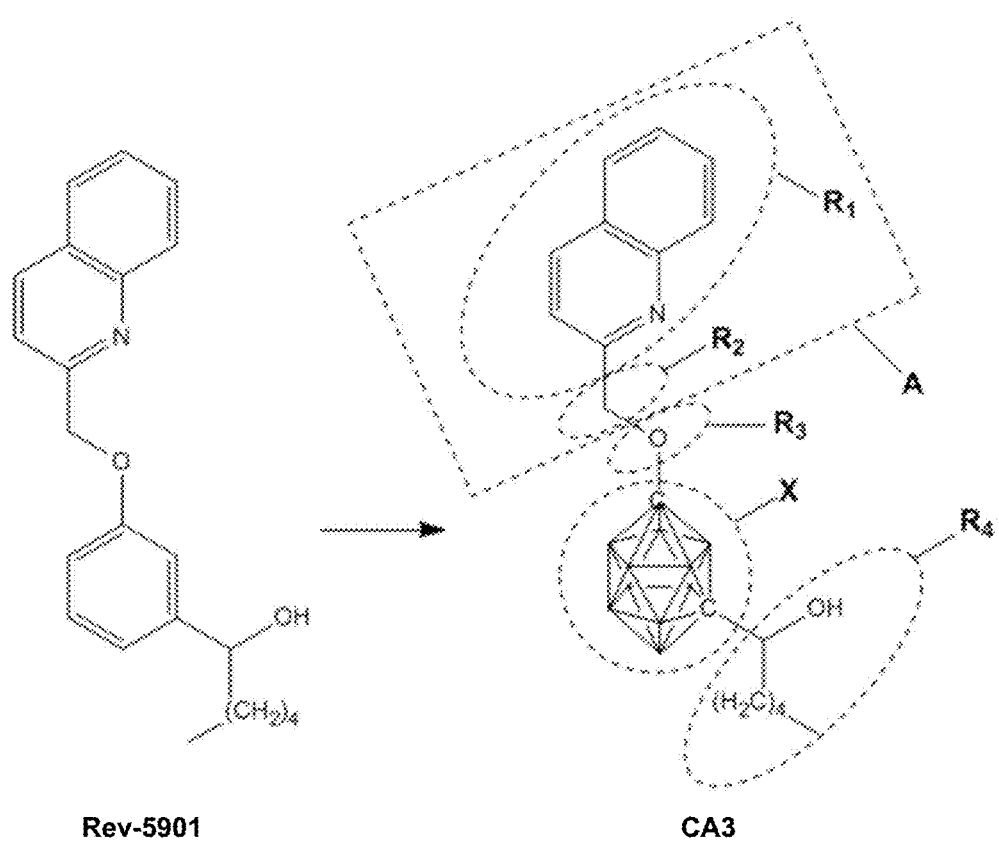
FIG. 4 is a diagram illustrating an example of the cluster analogue CA3 of lipoxygenase inhibitor Rev-5901 according to the invention.

This is illustrated in FIG. 4 with the example of the cluster analogue CA3 of lipoxygenase inhibitor Rev-5901 according to the invention:

The central phenyl ring in Rev-5901 is replaced by a carborane cluster in this case, thus arriving at cluster analogue CA3. The individual structural components of the general structure [A-$R_3$—X—$R_4$] are shown in FIG. 4.

The advantageous structural differences of the new compounds lead to improved metabolic stability and improved bioavailability in comparison with the known, for example phenyl-substituted, compounds, while having comparable or improved activity towards the enzymes.

According to the invention, the boron cluster is mete-substituted or pare-substituted as the ortho-compounds are known for being chemically and metabolically considerably more unstable, and the synthesis of said compounds is also extremely complex.

The two-fold substitution is also advantageous since, in many cases, mono-functionalised clusters have a considerably lower selective cytotoxicity towards tumour cells.

The replacement of phenyl rings by boron-containing clusters also leads to a considerable increase in the selective cytotoxicity towards various cancer cell lines.

In addition, the boron-containing compounds are in principle suitable for boron neutron capture therapy (BNCT), whereas the phenyl derivatives are not suitable for this.

The compounds according to the invention have the general structure

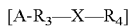

where
A=[R$_1$-R$_2$] or [R$_1$]
R$_1$=aryl, heteroaryl
R$_2$ f alkyl, aryl, heteroaryl, carbonyl, thiocarbonyl, alkyl ester, alkyl thioester
R$_3$=O, S, NH
X=closo- or n/do-boron cluster
R$_4$=

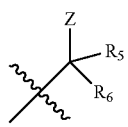

where Z=OH, SH, NH$_2$
where R$_5$ is selected from H, alkyl, aryl, heteroaryl, alkyl ether, alkyl thioether, alkylamine
and R$_6$ is selected from alkyl, aryl, heteroaryl, alkyl ether, alkyl thioester, alkylamine
and where R$_3$ and R$_4$ are in meta or pare positions in relation to one another.

The group A is connected to the group R$_3$ and is formed of R$_1$ or [R$_1$-R$_2$]. If A=[R$_1$-R$_2$], R$_2$ is a divalent group that interconnects R$_1$ and R$_3$.

R$_1$ is a functional group that is important for the pharmacological effect in the molecule, and comprises aromatic and heteroaromatic groups which are substituted or non-substituted in each case. The aromatic group preferably comprises 3 to 30 C atoms, more preferably 6 to 20 C atoms, most preferably 6 to 15 C atoms. The heteroaromatic group preferably contains one or more nitrogen atoms as heteroatoms. The heteroaromatic group preferably also contains 2 to 30 C atoms, more preferably 2 to 20 C atoms, most preferably 2 to 10 C atoms.

In a preferred embodiment, R$_1$ is a quinoline or naphthyl group that is substituted or non-substituted in each case.

For naphthyl and quinoline compounds which are phenyl-substituted in a central position in the molecule, LOX-inhibiting properties are already known. Examples thereof are known pharmaceutical compounds Rev-5901, MK-0591, L-674 or ICI-21965.

According to the invention, the group R$_2$ is selected from alkyl, aryl, heteroaryl, carbonyl, thiocarbonyl, alkyl ester, alkyl thioester.

According to the invention, the following applies to the above-mentioned formulae and for all the formulae mentioned below:

According to the invention, alkyl is understood to mean branched and non-branched, substituted and non-substituted groups. C$_1$ to C$_{20}$ alkyl groups are preferred, C$_1$ to C$_{10}$ alkyl groups are particularly preferred, and C$_1$ to C$_5$ alkyl groups are most preferred. Preferred substituents on the alkyl groups are selected from hydroxy, thio or amino groups.

According to the invention, aryl is understood to mean substituted and non-substituted aromatic groups having preferably 3 to 30 C atoms, more preferably 6 to 20 C atoms.

According to the invention, heteroaryl is understood to mean substituted and non-substituted aromatic groups having preferably 2 to 20 C atoms, more preferably 3 to 10 C atoms and at least one heteroatom, preferably up to 50% of the atoms contained in the heteroaromate. The heteroatoms are preferably selected from N, S and O.

In an advantageous embodiment, R$_2$ is a non-branched, preferably non-substituted alkyl group, having preferably 1 to 3 C atoms.

According to the invention, R$_4$ is understood to mean the following structure:
R$_4$=

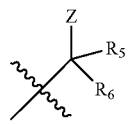

where Z=OH, SH, NH$_2$
where
where Z=OH, SH, NH$_2$
where R$_5$ is selected from H, alkyl, aryl, heteroaryl, alkyl ether, alkyl thioether, alkylamine
and R$_6$ is selected from alkyl, aryl, heteroaryl, alkyl ether, alkyl thioether, alkylamine
Preferably, Z=OH.

In a preferred embodiment, the groups R$_5$ and R$_6$ form a tetrahydropyranyl unit. For tetrahydropyranyl derivates which contain a phenyl ring in a central position, LOX-inhibiting properties are also known. ZD2138 is mentioned here by way of example.

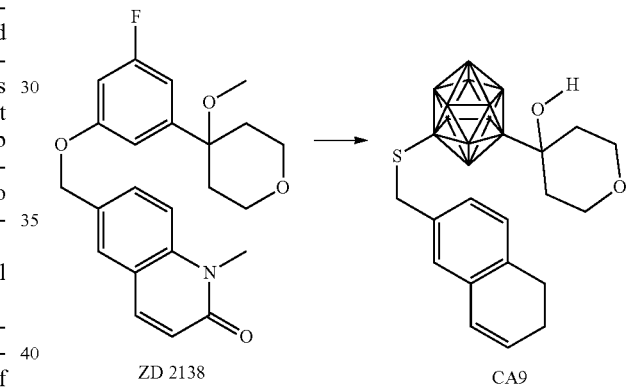

ZD 2138     CA9

In ZD 2138, the substituted phenyl ring is replaced by a cluster, thus arriving at cluster analogue CA9, which has improved pharmacokinetic properties. The extremely hydrophobic clusters allow the cell membrane to be crossed in an improved manner so that entering cells is thus easier and more efficient and said clusters can exert their effect on the LOX system in said cells.

In a preferred embodiment, Z is esterified or etherified by a group that is different from A. The etherification or esterification takes place following the method according to the invention.

According to the invention, the aromatic or heteroaromatic groups R$_1$ are connected to the group R$_3$ either directly or by means of a divalent group R$_2$. R$_2$ is preferably selected from alkyl, aryl, heteroaryl, carbonyl, thiocarbonyl, alkyl ester, alkyl thioester.

R$_3$ is directly bonded to the boron-containing cluster X and is selected from heteroatoms. R$_3$ is preferably represented by O, S or NH.

According to the invention, X is a nido- or closo-boron cluster.

Clusters of this kind may advantageously be used as pharmacophores, functional groups and three-dimensional structural elements.

In general, clusters are considered to be similar to their general definition as "an accumulation of the same thing"; they can have various geometries and can be charged or non-charged.

The geometries of the clusters are derived from Wade's rules [K. Wade, *Adv. Inorg. Chem. Radiochem.*, 1976, 18. 1] or the extended Wade-Mingos rules.

According to the invention, X represents nido- or closo-boron clusters which contain n=6 to 12 boron atoms, and m hydrogen atoms, where m=n+i, where i is an integer (from 1 to 10, preferably from 2 to 10, particularly preferably from 2 to 6).

Covered by the invention are n/do- or closo-boron clusters X where 1 to 4 B atoms within a cluster may be replaced by atoms of main-group elements or where 0 to 4 B atoms of a cluster are replaced by atoms of main-group elements.

The nido- or closo-boron clusters X preferably contain 1 to 4, preferably 1 or 2 carbon atoms, these carbon atom-containing boron clusters being referred to as carbaboranes, dicarbaboranes, dicarbadodecacarborane, dicarba-closo-dodecaboranes or also carboranes.

However, also covered by the invention are compounds in which X represents silaboranes having Si atoms instead of 1 to 4 boron atoms, phosphaboranes having P atoms instead of 1 to 4 boron atoms, azaboranes having N atoms instead of 1 to 4 boron atoms, thiaboranes having S atoms instead of 1 to 4 boron atoms.

However, compounds where X=boron-containing clusters which contain metals, referred to as metallacarboranes, are also covered by the invention. Said metallacarboranes are easily obtainable by reacting a boron-containing cluster with metal salts [M. F. Hawthorne, *Organomet. Chem.*, 1975, 100, 97].

Closo-boron clusters within the meaning of the invention describe compounds in which the boron atoms are at the corners of a deltahedron, i.e. a polyhedron, which is delimited by triangular faces only. An icosahedron is preferred such that the boron cluster is therefore in the shape of an icosahedron.

The hydrogen atoms of the B—H bonds of the closo-boron cluster are covalently bonded to the particular boron atom and face radially outwards.

Closo-boron clusters can be easily converted to nido-boron clusters. The structure of the nido-boron clusters is derived from the structure of the closo-boron clusters by one corner of the closo-cluster not being occupied by a boron atom. This therefore results in an "open" structure. The hydrogen atoms of said boranes again occupy all the radially outward positions on the boron atoms and additional places on the open parts of the polyhedron [see also Hey-Hawkins at al. *Chem Rev.* 2011, 111, 7,035].

A closo-carborane can be converted to the corresponding nido-carborane by means of any of the common methods, for example [see e.g. R. A. Wiesboeck, M. F. Hawthorne, *J. Am. Chem. Soc.*, 1964, 86, 1,642, M. F. Hawthorne, D. C. Young, P. M. Garrett, D. A. Owen, S. G. Schwern, F. N. Tebbe, P. A. Wegner, *J. Am. Chem. Soc.*, 1968, 90, 862, L. I. Zakharkin, V. S. Kirillova, *Izv. Akad. Nauk. SSSR. Ser. Khim.*, 1975, 11, 2,596, J. L. Maurer, A. J. Serino, M. F. Hawthorne, *Organometalics*, 1988, 7, 2,519, H. Tomita, H. Luu, T. Onak, *Inorg. Chem.*, 1991, 30, 812, J. J. Schaeck, S. B. Kahl, *Inorg. Chem.*, 1999, 38, 204].

Nido-carborane-containing compounds, namely both neutral, monoanionic and dianionic nido-carboranes, are also covered by the invention, the dianionic nido-carboranes also being referred to as carbollides or dicarbollides.

Corresponding metallacarboranes can also be formed from nido-carboranes that are isolobal in relation to cyclopentadienyl anions. According to the invention, the transformation into metallacarboranes is also considered to be a tool for modifying the properties of the clusters as pharmacophores and adapting said properties to the particular system. The metallacarboranes are themselves considered to be pharmacophores.

Preferred clusters X are:
a) boranes having main-group elements: $C_2B_8H_{10}$, $C_2B_{10}H_{12}$, $Si_2B_{10}H_{12}$, $P_2B_{10}H_{10}$, $SB_{11}H_{11}$, $C_2B_9H_{11}^{(-)}$, $NB_{11}H_{11}^{(-)}$, $PB_{11}H_{11}^{(-)}$, $CB_6H_7^{(-)}$, $CB_7H_8^{(-)}$, $CB_9H_{10}^{(-)}$, $CB_9H_{12}^{(-)}$, $CB_{10}H_{11}^{(-)}$, $CB_{11}H_{12}^{(-)}$, $SiB_{11}H_{12}^{(-)}$, $CB_{11}H_{12}^{(2-)}$, $SiB_{11}H_{11}^{(2-)}$, $SnB_{11}H_{11}^{(2-)}$, $GeB_{11}H_{11}^{(2-)}$, $C_2B_9H_{12}$, $C_2B_9H_{12}^{(-)}$; $C_2B_9H_{11}^{(2-)}$ b) cluster fragments: $R_aC_3B_nH_{n+3-a}^{(-)}$, $R_aC_2B_nH_{n+2-a}^{(-)}$, $C_3B_8H_{11}^{(-)}$, $R_2C_3B_8H_9^{(-)}$, $C_2B_9H_{11}^{(-)}$, $C_2B_9H_{11}^{(2-)}$, $R_2C_2B_9H_9^{(-)}$, (R=H, alkyl, aryl, silyl);

X=1,6-$C_2B_8H_{10}$, 1,10-$C_2B_8H_{10}$, 1,7-$C_2B_{10}H_{12}$, 1,12-$C_2B_{10}H_{12}$, 2,3-$C_2B_9H_{10}$, $Si_2B_{10}H_{12}$, $P_2B_{10}H_{10}$, $SB_{11}H_{11}$, $NB_{11}H_{11}^{(-)}$, $PB_{11}H_{11}^{(-)}$, $CB_6H_7^{(-)}$, $CB_7H_8^{(-)}$, $CB_9H_{10}^{(-)}$, $CB_9H_{12}^{(-)}$, $CB_{10}H_{11}^{(-)}$, $CB_{11}H_{12}^{(-)}$, $SiB_{11}H_{12}^{(-)}$, $CB_{11}H_{11}^{(2-)}$, $SiB_{11}H_{11}^{(2-)}$, $SnB_{11}H_{11}^{(2-)}$, $GeB_{11}H_{11}^{(2-)}$, 7,9-$C_2B_9H_{12}^{(-)}$, 7,9-$C_2B_9H_{11}^{2(-)}$, 2,9-$C_2B_9H_{12}^{(-)}$; 2,9-$C_2B_9H_{11}^{2(-)}$, $R_aC_3B_nH_{n+3-a}^{(-)}$, $RaC_2BnHn+_2-a^{(-)}$, $C_3B_8H_{11}^{(-)}$, $R_2C_3B_8H_9^{(-)}$, $C_2B_9H_{11}^{(-)}$, $R_2C_2B_9H_9^{(-)}$, (R=H, alkyl, aryl, silyl) is particularly preferred.

In a preferred embodiment, X=1,7-dicarba-closo-dodecaborane (meta-closo-carborane, 1,7-$C_2B_{10}H_{12}$). In a further preferred embodiment, X=1,12-dicarba-closo-dodecaborane (para-closo-carborane, 1,12-$C_2B_{10}H_{12}$).

Carboranes, specifically dicarba-closo-dodecaboranes (12), are distinguished by their lipophilia, electron pull, steric properties and stability (thermal and in relation to biological metabolism). Some of said carboranes are referred to as three-dimensional aromates and can be provided with functional groups or organic and inorganic groups by replacement of the hydrogen atoms both on the boron corners and on the carbon corners.

Preferred boron clusters are carboranes, i.e. carbon-containing boranes, that are derived by integrating isolobal carbon fragments.

If the cluster is a carborane, the BH units in the carborane have not been drawn in full for the sake of easier graphical illustration in this case. That is to say, the corner points in the cluster each represent a BH unit, and the C atoms are shown in their positions, as demonstrated for 1,7-$C_2B_{10}H_{12}$ by way of example:

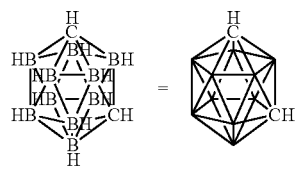

According to the invention, the groups $R_3$ and $R_4$ are in meta or pare positions in relation to one another.

If X represents carborane clusters, then X=1,7-dicarba-closo-dodecaboranes(12) (X=1,7-$C_2B_{10}H_{12}$) or X=1,12-dicarba-closo-dodecaboranes(12) (X=1,12-$C_2B_{10}H_{10}H_{12}$) or a related compound that is derived therefrom by applying the isolobal concept.

A related compound also means related clusters that are obtainable by synthesis from dicarba-closo-dodecaboranes (12).

If X is a boron cluster of main-group elements other than C (carbon), the same definition applies, only that the particular main-group element is in place of the C.

Both the charged and the non-charged clusters or complexes of cluster fragments are abbreviated to X in the following and in the claims. X thus generally represents a boron cluster, especially a carborane cluster, in particular one of the carborane clusters mentioned above or below.

On account of their particular metabolic stability, 1,7-dicarba-closo-dodecaboranes (mete-closo-carboranes, 1,7-$C_2B_{10}H_{12}$) are preferably used as clusters in order to substitute ring systems in the lead structures. The numbers 1 and 7 indicate the position of the carbon atoms within the cluster. The other positions are BH units, it being possible for the hydrogen atoms of individual or all BH units to be replaced by hydroxy groups, methyl groups or halogens (F, Cl, Br, I), optionally radiolabeled halogens.

Of the racemic representatives, enantiomerically pure compounds are also covered by the invention.

The hydrogen atoms of individual or a plurality of BH units may be replaced, completely or in part, by halogens or radiolabelled halogens F, Cl, Br, I (preferably by I=$^{131}$I) (embodiments 20 to 24). The compounds according to the invention are thus also suitable as labels for diagnostic purposes.

Halogens can be introduced, for example, by means of elementary iodine in the presence of acids or Lewis acids [M. Tominga, *Macromol. Rapid Comm.*, 2013, 34, 1,357; M. Scholz, E. Hey-Hawkins, *Chem. Rev.*, 2011, 111, 7,035].

In one embodiment, one or more BH units are substituted by radiolabelled B-halogen units.

According to the invention, the group $R_4$ represents hydroxyalkyl, thioalkyl or aminoalkyl groups which are free, but also etherified or esterified by groups that are the same or not the same as the group A according to the invention.

The carborane-containing compounds according to the invention are advantageously distinguished in that they are in part easier to obtain by synthesis than corresponding phenyl derivatives. The use of specific synthesis steps makes it possible, for example, to do without the use of protective groups.

Another crucial advantage is the improved solubility in many common solvents, which advantage is achieved by the substitution of the phenyl unit by a carborane cluster within the lead structures.

According to the invention, X generally represents a boron cluster, in particular a carborane cluster. X is preferably one of the already previously defined cluster types. $R_1$, $R_2$ and $R_3$ are interlinked in this sequence and bonded to the cluster via $R_3$. This grouping is in the meta position in relation to $R_4$ in a preferred variant and in the pare position in relation to $R_4$ in a further preferred variant.

Figure 5:
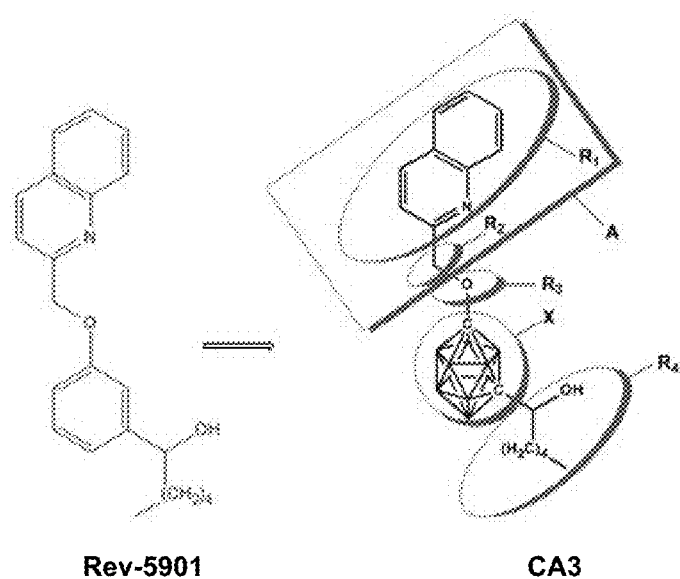
FIG. 5 is a diagram illustrating LOX inhibitor Rev-5901 as an example to show the principle of replacing a ring structure in LOX-inhibiting compounds with a suitable cluster frame.

With LOX inhibitor Rev-5901 taken as an example, the principle of replacing a ring structure in LOX-inhibiting compounds with a suitable cluster frame can be generally depicted as shown in FIG. 5.

The incorporation of a cluster in place of the phenyl ring in Rev-5901 leads to cluster analogue CA3 [1-(7-quinolin-2-ylmethoxy-1,7-dicarba-closo-dodecaboran(12)yl)-hexan-1-ol], embodiment 3.

The compound of formula CA3 (embodiment 3) is the carboranyl analogue of Rev-5901, but in addition advantageously has the positive properties of carboranes. The three-dimensional hydrophobic carborane cage is larger than the phenyl ring and is suitable as a lipophilic, hydrophobic pharmacophore. Said cage gives the OH and quinoline groups a two-dimensional orientation and itself acts as a modifiable functional group.

The compounds according to the invention advantageously have improved solubility behaviour they dissolve both in non-polar solvents, such as pentanes, and in polar solvents, such as ethanol.

For example, Rev-5901 has a solubility of just 29.7 mmol/l in ethanol or 29.8 mmol/l in DMSO. However, cluster analogue CA3 exhibits a significantly increased solubility of 86.8 mmol/l in ethanol or 208.3 mmol/l in DMSO.

It is known in the literature that carboranes also have greater metabolic stability [see e.g. F. Issa, M. Kassiou, L. M. Rendina, *Chem. Rev.* 2011, 111, 5,701 or M. L. Beer, J. F. Valiant, *J. Med. Chem.*, 2010, 53, 8,012].

The carborane analogues of known, phenyl-substituted LOX inhibitors advantageously have comparable $IC_{50}$ values in inhibition tests on enzyme system 5-lipoxygenase/5-lipoxygenase-activating protein in spite of the replacement of the phenyl ring (see Table 2). The effectiveness of the compounds is therefore not negatively influenced by the replacement of the phenyl ring with a carborane cluster. It is thus now possible to combine the advantageous properties of carboranes, such as high solubility, greater metabolic stability and broader application possibilities, with the LOX-inhibiting properties of the phenyl-substituted compounds.

The carborane analogues of known phenyl-substituted LOX inhibitors, such as compound 3 (an analogue of Rev-5901) surprisingly have considerably higher cytotoxicity towards various cancer cell lines in comparison with the phenyl-based compounds (see also section on cytotoxicity).

This can be demonstrated on melanoma and colon cancer cell lines. Particularly melanoma cancer cell line A375, which is highly aggressive and is known for being resistant to chemotherapy, has $IC_{50}$ values in the single-digit micromolar range for the carborane analogues of phenyl-substituted LOX inhibitors, i.e. half of the analysed cells die off at very low concentrations of compound 3 in the medium. This is of great significance in particular to targeted metastasis therapy.

By contrast, the original, phenyl-based comparative substance, Rev-5901, has $IC_{50}$ values of between 25 and more than 50 micromolar, depending on the method of analysis used, and thus has considerably lower cytotoxicity towards the cancer cell line.

A high degree of selectiveness of the compounds towards healthy and pathological cells is also important for subsequent pharmacological applicability.

Cytotoxicity analyses were also carried out on healthy cells to determine the selectiveness. Cell line MRC-5 was used for this purpose. In order to establish the selectiveness between healthy cells and cancer cells, the $IC_{50}$ value for healthy cells was divided by the $IC_{50}$ value for cancer cells. It emerges that phenyl-based comparative substance Rev-5901 has an $IC_{50}$ value of 70 micromolar for healthy cells, and therefore the selectiveness of said compound between healthy cells and cancer cells is of a value of just 2.8.

By contrast, the compound 5 according to the invention (embodiment 5), for example, exhibits an $IC_{50}$ value of 8 micromolar for A375 cancer cells and an $IC_{50}$ value of 82 micromolar for MRC-5, a considerably advantageous selectiveness of 10.2 therefore being calculated. This means that the window of action of these active ingredients is trebled by using carborane-substituted LOX inhibitors.

It also emerges that mono-functionalised clusters in which $R_4$=H only exhibit insufficient cytotoxicity towards cancer cells (comparative examples 1 and 2, section on cytotoxicity).

In one embodiment, the functionalisation takes place by means of deboronation methods and the isolobal replacement of BH units. The hydrogen atoms of individual or a plurality of BH units may also, for example, be substituted by halogens or radiolabelled halogens. The property of the cluster can thus be further modified. For example, the cluster can also be labelled by linking a B—I bond to $^{131}$I.

A charged anionic species is derived from the highly hydrophobic cage by deboronation.

In a further embodiment, the functionalisation takes place by means of conversion to a metallacarborane in order to further modify the existing properties.

The invention also covers a preparation method for the compounds according to the invention, of general structure

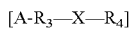

where
A=[$R_1$-$R_2$] or [$R_1$]
$R_1$=aryl, heteroaryl
$R_2$=alkyl, aryl, heteroaryl, carbonyl, thiocarbonyl, alkyl ester, alkyl thioester
$R_3$=O, S, NH
X=closo- or nido-boron cluster
$R_4$=

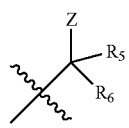

where Z=OH, SH, $NH_2$
where $R_5$ is selected from H, alkyl, aryl, heteroaryl, alkyl ether, alkyl thioether, alkylamine
and $R_5$ is selected from alkyl, aryl, heteroaryl, alkyl ether, alkyl thioether, alkylamine
and where $R_3$ and $R_4$ are in meta or para positions in relation to one another.

The group A is connected to the group $R_3$ and is formed of $R_1$ or [$R_1$-$R_2$]. If A-[$R_1$-$R_2$], then $R_2$ is a divalent group that interconnects $R_1$ and $R_3$.

The preparation method according to the invention comprises the steps of:
a) hydroxyalkylating or thioalkylating or aminoalkylating the cluster X,
b) hydroxylating or thiolating or aminating the cluster X, so as to form an intermediate compound of general formula [H—$R_3$—X—$R_4$]
where
$R_3$=O, S, NH
X=nido- or closo-boron cluster
$R_4$=

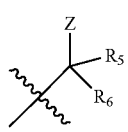

where Z=OH, SH, $NH_2$
where $R_5$ is selected from H, alkyl, aryl, heteroaryl, alkyl ether, alkyl thioether, alkylamine
and $R_6$ is selected from alkyl, aryl, heteroaryl, alkyl ether, alkyl thioether, alkylamine
and where $R_3$ and $R_4$ are in meta or para positions in relation to one another
c) selectively etherifying or esterifying H—$R_3$ in order to introduce A,
it being possible to interchange steps a) and b) as desired.

The first step is preferably the hydroxyalkylation, hydroxythiolation or hydroxyamination, the second step is preferably the hydroxylation or thiolation or amination, and the third step is preferably the selective etherification. However, the sequence of the first two steps can also be modified as desired.

Hydroxyalkylation

Hydroxyalkylation takes places, according to the prior art, by deprotonation of the carborane by means of a suitable base, and subsequent reaction with ketones or aldehydes [J. Cai, Chem. Left., 1996, 791-792]. Similarly, thioalkylation can take place by means of the corresponding thiocarbonyl compound, and aminoalkylation can take place by means of a corresponding enamine.

By means of the following hydroxyalkylation method, a hydroxyalkyl group is preferably introduced on the carborane.

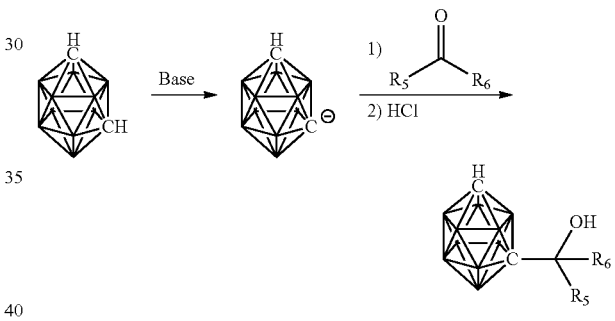

According to the invention, the group $R_5$ is selected from H, alkyl, aryl, heteroaryl, alkyl ether, alkyl thioether.

According to the invention, the group $R_6$ is selected from alkyl, aryl, heteroaryl, alkyl ether, alkyl thioether.

The first step is deprotonation by means of a suitable base, preferably alkali metal organyles, metallamides, silazanes, metal hydrides or ammonium compounds, such as n-BuLi, MeLi, lithium hexamethyldisilazane (LiHMDS), sodium hexamethyldisilazane (NaHMDS), potassium hexamethyldisilazane (KHMDS), lithium diisopropylamide (LDA), tetrabutylammonium fluoride (TBAF), NaH, $NaNH_2$ or compounds having comparable basicity. Subsequently, carbonyl compounds, such as aldehydes or ketones, are added to the resultant carboranyl anions, the carbonyl carbon of said compounds being nucleophilically attacked by the carboranyl anion. Subsequent acidic work-up delivers the desired hydroxyalkyl carboranes.

Similarly, thioalkylation takes place by means of thiocarbonyl compounds, and aminoalkylation takes place by means of the corresponding imine or enamine.

Hydroxylation

Hydroxylation can take place, as previously has done in the prior art, by reacting the mono-lithiated cluster with $O_2$, dibenzoyl peroxide, bis(trimethylsilyl)peroxide or a trialkyl borate, and by subsequent oxidation. However, hydroxylation preferably takes place, according to the prior art, by deprotonation of the cluster by means of a suitable base, linking of a heteronuclear bond to a trialkyl borate or boron trihalide, and subsequent oxidation [K. Ohta, *Inorg. Chem.*, 2007, 46, 3,966].

By means of the following hydroxylation method, a hydroxy group is preferably introduced on the carborane (on a C atom of the carborane cluster), which group may later be further modified, e.g. esterified or etherified:

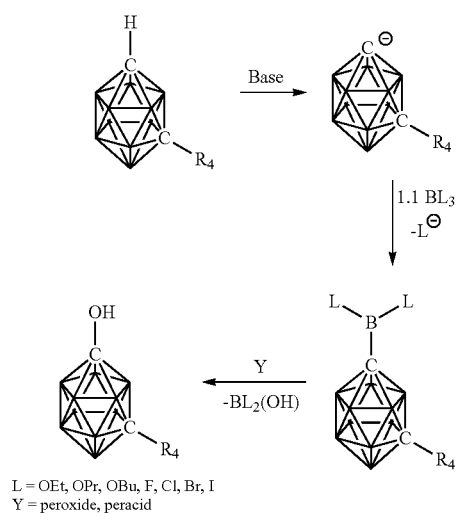

L = OEt, OPr, OBu, F, Cl, Br, I
Y = peroxide, peracid

The first step is the deprotonation of the C atom by means of a suitable base, preferably alkali metal organyles, metal-lamides, silazanes, metal hydrides or ammonium compounds, such as n-Bui, MeLi, lithium hexamethyldisilazane (LiHMDS), sodium hexamethyldisilazane (NaHMDS), potassium hexamethyldisilazane (KHMDS), lithium diisopropylamide (LDA), tetrabutylammonium fluoride (TBAF), NaH, $NaNH_2$ or compounds having comparable basicity. The second and central step of the method is the formation of a heteronuclear bond. B represents the element boron; however, other elements are also conceivable (e.g. P, As). L is a halide (F, Cl, Br, I), an alcoholate (OR) or an alkyl group (R). R is a linear or branched, saturated or unsaturated, aromatic or non-aromatic, chiral or achiral carbon-containing group. L may be different within $BL_3$ and may also be attached in the periphery. The species containing a heteronuclear bond may be isolated; however, said species may also be further reacted directly in situ. The last step in the illustration is the reaction with a peroxo species. This can be either in particular a peracid (e.g. peracetic acid) or a peroxide (hydrogen peroxide, alkyl peroxide) or another typical oxidising agent.

According to the invention, the compound is purified by selecting a suitable aqueous base, preferably selected from NaOH and KOH.

By means of the base, the hydroxycarborane as an anion is advantageously converted to the aqueous phase and is thus isolated from the starting material, which is in protonated form in the organic phase, by means of phase separation. Unreacted starting material can thus advantageously be recovered by means of extraction. A process of purification by means of a solvent, and therefore by means of more expensive column chromatography, is therefore not required.

In the purification process according to the invention, the raw product is preferably suspended in an aqueous basic solution (preferably diluted KOH or NaOH solution) (or is extracted multiple times if the raw product in still in solution) and is then extracted multiple times by means of an organic solvent (preferably an apolar solvent, such as diethyl ether). The starting material is in the organic phase. The aqueous basic phases are then acidulated (preferably by means of HCl down to approximately pH=1). In this process, the product appears as a white solid. Said solid can be extracted again by means of an organic solvent (preferably an apolar solvent, such as diethyl ether). Once the solvent has been removed, the corresponding substituted hydroxycarborane is obtained.

If a sufficient level of purity of the product is not obtained, a sublimation step is possible.

All hydroxycarboranes and other hydroxylated boron-containing clusters can be obtained by means of this method.

Thiolation

Thiolation takes place, according to the prior art, by deprotonation of the carborane (of a C atom of the carborane cluster) by means of a suitable base, and subsequent reaction with elementary sulfur [J. Plešek, S. Heřmánek, *Collect. Czech. Chem. Commun.*, 1981, 46, 687-692]. The reaction sequence is shown schematically as follows:

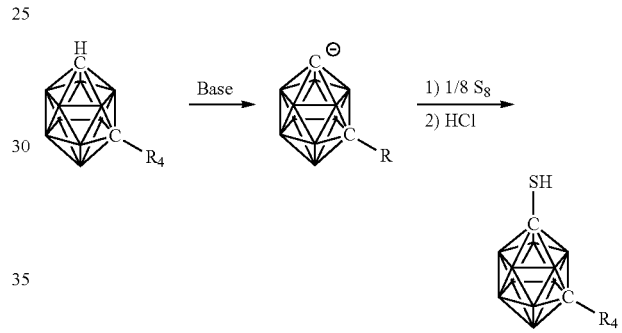

The first step is the deprotonation of a C atom by means of a suitable base, preferably alkali metal organyles, metal-lamides, silazanes, metal hydrides or ammonium compounds, such as n-BuLi, MeLi, lithium hexamethyldisilazane (LiHMDS), sodium hexamethyldisilazane (NaHMDS), potassium hexamethyldisilazane (KHMDS), lithium diisopropylamide (LDA), tetrabutylammonium fluoride (TBAF), NaH, $NaNH_2$ or compounds having comparable basicity. The second step of the method is the nucleophilic substitution of elementary sulfur by means of these carboranyl anions. Following acidic aqueous work-up, the corresponding thiocarboranes are obtained.

According to the invention, the compound is purified by selecting a suitable aqueous base, preferably selected from NaOH and KOH.

By means of the base, the thiocarborane as an anion is advantageously converted to the aqueous phase and is thus isolated from the starting material, which is in protonated form in the organic phase, by means of phase separation. Unreacted starting material can thus advantageously be recovered by means of extraction. A process of purification by means of a solvent, and therefore by means of more expensive column chromatography, is therefore not required.

In the purification process according to the invention, the raw product is preferably suspended in an aqueous basic solution (preferably diluted KOH or NaOH solution) (or is extracted multiple times if the raw product in still in solution) and is then extracted multiple times by means of an organic solvent (preferably an apolar solvent, such as diethyl ether). The starting material is in the organic phase. The aqueous basic phases are then acidulated (preferably by means of HCl down to approximately pH=1). In this process, the product appears as a white solid. Said solid can be extracted again by means of an organic solvent (preferably an apolar solvent, such as diethyl ether). Once the solvent has been removed, the corresponding substituted thiocarborane is obtained.

If a sufficient level of purity of the product is not obtained, a sublimation step is possible.

All thiocarboranes and thiolated boron-containing clusters can be obtained by means of this method.

Amination

According to the invention, amination takes place according to a method from the prior art [see e.g. Scholz et al., *Chem. Rev.*, 2011, 111, 7,035-7,062].

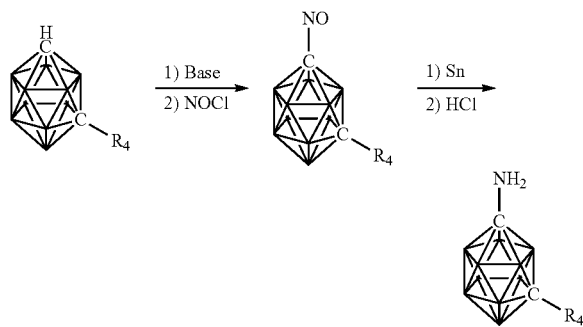

In a manner similar to thiolation and hydroxylation, the carborane (a C atom of the carborane cluster) is first deprotonated by means of a suitable base. The carbanion is then reacted with a nitrogen compound that preferably comprises a positively charged nitrogen atom, e.g. of a nitroso compound. Following reduction and work-up, the free amine is obtained.

The two steps a and b may advantageously proceed in any desired sequence. It is also possible to dispense with a complex protective group strategy. If, for example, a hydroxy or thio function is first introduced, it is not necessary to provide said function with a protective group before the compound is hydroxyalkylated.

Inversely, it is not necessary either to protect the free hydroxy function on the group $R_4$ before hydroxylation or thiolation takes place. This significantly reduces the number of synthesis steps.

Selective Etherification

A substantial component of the method according to the invention is the selective etherification of the hydroxy, thio or amino function H—$R_3$ directly bonded to the cluster.

The reaction of the compounds, from the two method steps a) and b), with benzyl or alkyl halides, tosylates and triflates, and other common alkylation reagents, surprisingly leads only to functionalisation of the hydroxy, mercapto or amino function directly bonded to the carborane. Hydroxyalkyl groups, thioalkyl groups or aminoalkyl groups are advantageously not functionalised in this method. As a result, it is possible to dispense with the complex and expensive use of protective groups. Various bases may advantageously also be used for the deprotonation of the OH, SH or NH function. In this case too, the carborane-bonded hydroxyalkyl, thioalkyl or aminoalkyl groups are not etherified. By means of the following etherification method, an ether or thioether group is preferably introduced on the carborane.

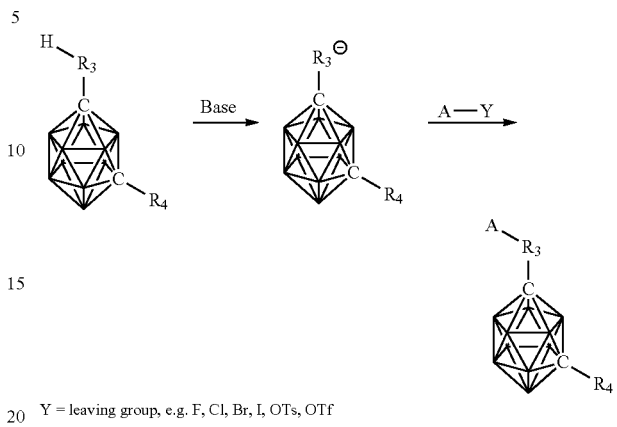

Y = leaving group, e.g. F, Cl, Br, I, OTs, OTf

The first step is deprotonation by means of a suitable base, preferably alkali metal organyles, metallamides, silazanes, metal hydrides or ammonium compounds, such as n-BuLi, MeLi, lithium hexamethyldisilazane (LiHMDS), sodium hexamethyldisilazane (NaHMDS), potassium hexamethyldisilazane (KHMDS), potassium carbonate, lithium diisopropylamide (LDA), tetrabutylammonium fluoride (TBAF), NaH, NaNH$_2$ or compounds having comparable basicity. The second step of the method is the nucleophilic substitution of alkyl or aryl halides by these thio or hydroxy carboranyl anions. According to the invention, the purification process takes place by addition of protic solvents, such as water (bases, particularly KOH or NaOH, may also be added), and subsequent extraction by means of solvents, such as diethyl ether. In the process, the starting material remains in the aqueous phase, and the product remains in the ethereal phase. This means that expensive column-chromatography purification is not necessarily required. Once the solvent has been removed, the products are obtained as solids.

It was previously only possible to synthesise thioethers of ortho-carborane, to a very high degree of complexity, by using symmetrically disubstituted disulfides [F. Teixidor, M. A. Flores, C. Viñas, *Organometallcs*, 1999, 18, 5,409-5,411]. The methods shown here fundamentally simplify this reaction.

In particular, the invention covers the method for selectively etherifying thiocarboranes and hydroxycarboranes or aminocarboranes in the presence of carboranyl-bonded free hydroxyalkyl or thioalkyl or aminoalkyl groups. This is shown by way of example on the basis of a hydroxyalkyl compound.

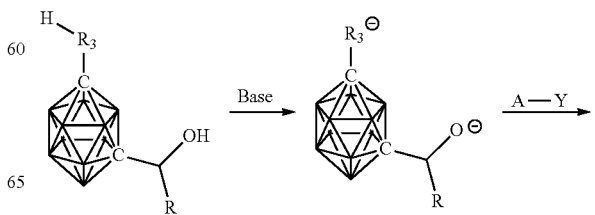

-continued

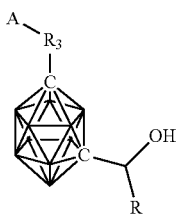

Y = leaving group, e.g. F, Cl, Br, I, OTs, OTf and others

The first step is deprotonation by means of a suitable base, preferably alkali metal organyles, metallamides, silazanes, metal hydrides or ammonium compounds, such as n-BuLi, MeLi, lithium hexamethyldisilazane (LiHMDS), sodium hexamethyldisilazane (NaHMDS), potassium hexamethyldisilazane (KHMDS), potassium carbonate, lithium diisopropylamide (LDA), tetrabutylammonium fluoride (TBAF), NaH, NaNH$_2$ or compounds having comparable basicity. The second step of the method is the nucleophilic substitution of alkyl or aryl halides, triflates and tosylates or other alkylation reagents by the aminocarbonyl, thiocarbonyl or hydroxycarbonyl anions. According to the invention, the purification process takes place by addition of protic solvents, such as water (acids, particularly HCl, may also be added), and subsequent extraction by means of solvents, such as diethyl ether. In the process, the product remains in the ethereal phase. This means that expensive column-chromatography purification is not necessarily required. Once the solvent has been removed, the products are obtained.

By means of this method, advantageously only the carboranyl-bonded thio, amino or hydroxy groups are etherified, while carboranyl-bonded hydroxyalkyl or thioalkyl or aminoalkyl functions do not react.

The compounds according to the Invention of structure

[A-R$_3$—X—R$_4$] where A=[R$_1$-R$_2$] or [R$_1$]

are therefore advantageous and can be obtained in at most three reaction stages in a manner novel over the prior art.

Figure 6:
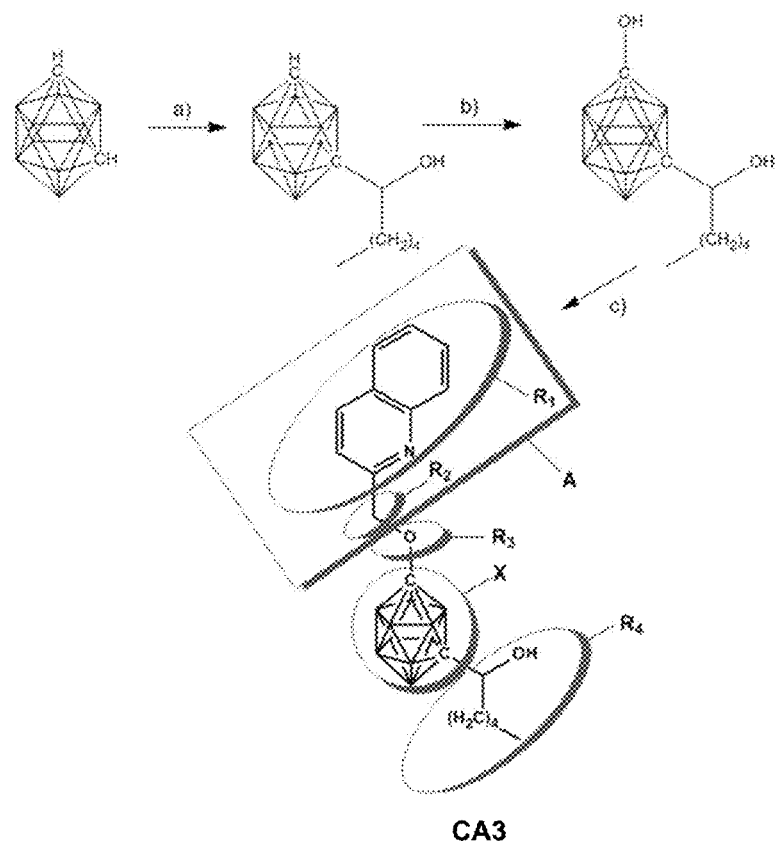
FIG. 6 is a diagram illustrating one embodiment of the overall method of present disclosure, shown by way of example on the basis of the synthesis of compound CA3 (embodiment 3), the carborane analogue of Rev-5901.

The overall method is shown by way of example on the basis of the synthesis of compound CA3 (embodiment 3), the carborane analogue of Rev-5901, as shown in FIG. 6.

It is emphasised that, in the compounds according to the invention, the hydroxy, thio, amino and hydroxyalkyl or thioalkyl or aminoalkyl groups may also be positioned on the boron atoms.

Advantageously, after the groups R$_3$ and R$_4$ have been introduced, one or more B—H hydrogen atoms may also be additionally substituted.

Furthermore, one of the groups R$_3$ and R$_4$ may also be positioned on a C atom, and the other may be positioned on a boron atom. The two groups are in meta or para positions in relation to one another.

According to the invention, Z, namely the free amino, thio or hydroxy group of group R$_4$, may be etherified or esterified by a group that is different from A, in a step following the method according to the invention, by means of common methods. This is also a subject of the invention.

Use

The use of the compounds according to the invention for pharmacological and medical applications is also a subject of the invention.

The central position of the cluster in the compounds according to the invention explicitly influences the metabolic and pharmacokinetic properties of the compounds. The carborane-substituted compounds have improved solubility and greater metabolic stability while having the same inhibiting activity as phenyl-substituted compounds.

Meta-substituted clusters have even greater metabolic stability than their ortho or pare analogues [E. Svantesson, J. Pettersson, A. Oln, K. Markides, S. Sjöberg, Acta Chem. Scand. 1999, 53, 731].

As a result, the compounds are available in the body in their active form for a longer period and have a longer duration of action, without loss of the inhibiting activity.

Furthermore, the carborane-substituted compounds according to the invention have considerably higher cytotoxicity towards various cancer cell lines and have a considerably wider window of action. This means that it is also possible to use concentrations that are considerably higher than are actually required for the cancer cells to die off, without healthy cells being affected.

The use of said compounds or salts thereof for inhibiting or modulating the LOX system, in particular 5-LOX or the 5-lipoxygenase-activating protein, referred to in the following as FLAP, is a subject of the invention. The size, lipophilia and electron pull of the cluster is intended to be exploited to influence the biological properties of the derivatives. The lipophilic nature of the cluster makes the compound well-placed to interact with the membrane-anchored LOX system.

The use of the compounds according to the invention or salts thereof for imitating arachidonic acid and derivatives thereof in biological systems is also a subject of the invention.

The invention covers the use of the compounds according to the invention for imitating arachidonic acid (AA) and derivatives thereof in biological systems. Said invention therefore also covers the use of said compounds in all LOX-independent, but AA-associated processes or systems. These include, inter alia, the effect on other enzymes and receptors. Cyclooxygenase is highlighted as an enzyme; the family of GPCRs (G-protein-coupled receptors), CBs (cannabinoid receptors), CRTH2 (chemoattractant receptor-homologous molecules expressed on TH2 cells) are highlighted as receptors. Nuclear factors, such as PPARs (peroxisome proliferator-activated receptors) and C/EBP, are biological fields of application of the described inhibitors.

The introduction of a cluster also makes it possible to modify known, phenyl-substituted compounds such that the biological targets of these compounds are widened. In this respect, it is now possible for the cluster analogue to target not only the LOX system, but also other components of the organism (enzymes, receptors, nucleic acids, etc.).

The use of the compounds according to the invention or salts thereof as drugs for treating arachidonic acid-associated diseases is also a subject of the invention.

A method for treating or preventing arachidonic acid-associated diseases, comprising the step of administering an effective dose of one or more compounds according to the invention or salts thereof to an individual requiring said dose, is also a subject of the invention.

The use of the compounds according to the invention or salts thereof as drugs for treating or preventing asthma, allergies, rhinitis, cardiovascular diseases, Alzheimer's disease, stomach/intestinal, renal and vascular complaints, complications of pregnancy, disorders of the CNS (central nervous system) and of the visual process, and in pain mediation and cancer.

The compounds according to the invention or salts thereof for use in the treatment of the above-mentioned diseases are also subjects of the invention.

The use of the compounds according to the invention or salts thereof for preparing a drug or diagnostic agent for treating the above-mentioned diseases is also a subject of the invention.

The use of the compounds according to the invention for imaging, diagnostic or therapeutic methods, in particular in biological research, radiology or nuclear medicine, is also a subject of the invention. The following are noted in particular:

BNCT (Boron Neutron Capture Therapy):

The fact that the inhibitors having boron clusters have a higher boron content makes it possible to use the compounds in BNCT (boron neutron capture therapy). BNCT sometimes concentrates on the treatment of cancer. Since the LOX system has significant functions in cancers, the substances according to the invention are suitable not only as BNCT and tumour imaging agents, but also as cancer drugs. Other examples that have targets other than those linked to cancer are also possible candidates for being bombarded with thermal neutrons. In general, an the mentioned boron-containing compounds are suitable for BNCT.

Other Use of the Compounds:

The use of the compounds according to the invention for BNCS (boron neutron capture synovectomy), in MRI (magnetic resonance imaging), PET (positron emission tomography), SPECT (single-photon emission computed tomography), PIGE (particle-induced γ-ray emission) and AFM-NIAR (atomic force microscopy with neutron-induced alpha-autoradiography) is also part of the invention.

The use of the compounds according to the invention, in particular the derived nido-carboranes and metallacarboranes and the radiolabelled derivatives for imaging and diagnostic purposes is also claimed.

A pharmaceutical composition, containing one or more of the compounds according to the invention or salts thereof, is also a subject of the invention. The active ingredients may be present together with one or more typical carriers, solvents, dilutants and/or basic materials in order to prepare typical preparations, such as tablets, pills, powders, pastilles, sachets, capsules, elixirs, suspensions, emulsions, solutions, syrups, aerosols (as a solid or in a liquid medium), ointments, soft and hard gelatin capsules, preparations for local use, sterile-packaged powders, mouthwashes or mouth rinses, or the like.

Examples of suitable carriers, basic materials and dilutants are lactose, glucose, saccharose, sorbitol, mannitol, starches, acacia gum, calcium phosphate, alginates, tragacanth, gelatin, calcium silicate, microcrystalline cellulose, polyvinylpyrrolidone, cellulose, aqueous syrup, water, water/ethanol, ethanol, water/glycol, water/polyethylene, glycol, propylene glycol, methyl cellulose, methyl hydroxybenzoates, propyl hydroxybenzoates, talc, magnesium stearate, mineral oil or fatty substances, such as hard fat, or suitable mixtures thereof. The compositions may additionally contain lubricants, wetting agents, emulsifiers, suspending agents, preservatives, sweeteners, flavours and the like. The drug may be formulated such that the active ingredients are released rapidly, long-lastingly or in a delayed manner after being administered to the patient.

EMBODIMENTS

The invention will be described below in more detail on the basis of embodiments, without the invention being limited thereto.

The synthesis of the cluster analogues of embodiments 1 to 23 and comparative examples 1 to 3 will be first be described:

All the reactions mentioned below were carried out in Schlenk flasks in a protective atmosphere of nitrogen. The solvents (diethyl ether, THF, $CH_2Cl_2$, n-hexane) were purified in a solvent drying system, SPS-800 series (MBRAUN GmbH); tetrahydrofuran (THF) was distilled by means of Na/benzophenone. The acetic ester and the n-hexane for the chromatography were used in an impurified form, n-hexane being used as an isomer mixture. The commercial, deuterated solvents ($CDCl_3$, $CD_3COCD_3$, $CD_3OD$ and $D_2O$) were used unchanged. Trimethyl borate was distilled before use. Meta-carborane, n-BuLi, LiHMDS, NaHMDS, potassium carbonate und peracetic acid (Wofasteril®, KESLA PHARMA WOLFEN GmbH) and all other chemicals were used unchanged. The IR spectra were measured on a PerkinElmer system 2000 FT-IR spectrometer in KBr and on a AutoImage microscope system having an MCT detector (PerkinElmer). The $^1H$, $^{13}C$ and $^{11}B$ NMR spectra were recorded on an ADVANCE DRX 400 spectrometer (Bruker). The chemical shifts in the $^1H$, $^{13}C$ and $^{11}B$ NMR spectra are shown in parts per million (ppm) at 400.13 MHz, 100.63 MHz and 161.97 MHz. Tetramethyl silane is used as an internal standard for the first two, and $BF_3(OEt_2)$ is used as an external standard for the $^{11}B$ NMR spectra. The mass spectra were recorded on an FT-ICR-MS Bruker Daltonics ESI mass spectrometer (APEX II, 7 Tesla); the element analyses were recorded on a VARIO EL (Heraeus). The melting points were determined in capillaries (GALLENKAMP). The data for the X-ray crystal structure analyses were recorded on a Gemini diffractometer (Agilent Technologies) by using Mo—$K_α$ radiation (λ=71.073 pm) and ω-scan rotation. The data reduction was carried out by CrysAlisPro (CrysAlisPro: data colection and data reduction software package, Agiient Technologies) and the program SCALE3 ABSPACK (SCALE3 ABSPACK: empirical absorption correction using spherical harmonics) for empirical absorption correction. The structures were solved by means of direct methods using SIR92. The refinement of all non-hydrogen atoms was carried out by SHELXL-97. The structures were generated by Diamond and ORTEP.

In the drawings, the following applies:
●=oder BH
○=C

 = $CH_2$ or $CR_2$

Each of the drawings for the X-ray structure analyses shows the ORTEP diagram of the compound, showing thermal ellipsoids at 30% probability.

Embodiment 1

1-(1,7-Dicarba-closo-dodecaboran(12)yl)-hexan-1-ol

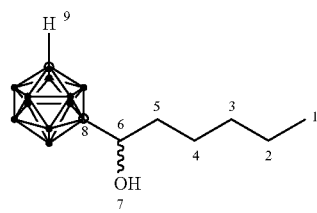

17.7 ml (1.64 M in n-hexane, 29.0 mmol, 1.05 eq.) of an n-butyl lithium solution is slowly dropped into a solution of 4.03 g (27.6 mmol, 1.0 eq.) of 1,7-dicarba-closo-dodecaborane(12) in 80 ml of diethyl ether at 0° C. After two hours, 3.31 ml (2.76 g, 27.6 mmol, 1.0 eq.) of hexanal, dissolved in 10 ml of diethyl ether, is added to the clear, colourless solution. After 30 minutes, the solution is heated to room temperature. After 24 hours, 50 ml of distilled water is added to the solution, which is extracted three times by means of 50 ml of diethyl ether on each occasion. The organic phases are combined and washed by means of saturated sodium chloride solution. Drying takes place by means of sodium sulfate, the solvent is removed under reduced pressure, and the residue is filtered by means of silica gel (eluent: n-hexane/ethyl acetate, 5:1 v/v). The obtained highly viscous liquid is recrystallised from n-hexane, and the product is obtained in the form of colourless flakes.

Yield: 6.34 g (25.8 mmol, 94%)
$R_f$ value: 0.64 (eluent: n-hexane/ethyl acetate 5:1 v/v)
Melting point: 57.6-58.3° C.
$^1$H NMR (CDCl$_3$): δ=0.89 (t, 3H, 1-CH$_3$, $^3J_{HH}$=6.5 Hz), 1.12-2.95 (br m, 10H, BH), 1.28 (m, 6H, 2,3,4-CH$_2$), 1.56 (m, 2H, 5-CH$_2$), 1.82 (br s, 1H, 7-OH), 2.92 (br s, 1H, 9-CH), 3.75 (br d, 1H, 6-CH, $^3J_{HH}$=10.0 Hz) ppm.
$^{11}$B{$^1$H} NMR (CDCl$_3$): δ=−16.2 (s, 2B, BH), −13.6 (s, 2B, BH), −12.2 (s, 2B, BH), −11.1 (s, 2B, BH), −8.7 (s, 1B, BH), −5.1 (s, 1B, BH) ppm.
$^{13}$C{$^1$H} NMR (CDCl$_3$): δ=13.9 (s, 1-CH$_3$), 22.4 (s, 2-CH$_2$), 26.1 (s, 3-CH$_2$), 31.3 (s, 4-CH$_2$), 37.3 (s, 5-CH$_2$), 54.3 (s, 9-CH), 72.6 (s, 6-CH), 82.7 (s, 8-C$_q$) ppm.
Mass spectrometry (ESI neg., CH$_2$Cl$_2$/CH$_3$OH):
Calculated: m/z=244.3
Determined: m/z=243.2 (100%, [M−H]$^-$), 216.2 (22%, [M−C$_2$H$_5$]$^-$), 143.0 (5%, [M−C$_6$H$_{13}$O]$^-$).
IR spectroscopy (KBr, ṽ in cm$^{-1}$): 3,387 (s), 2,957 (s), 2,928 (s), 2,859 (m), 2,602 (s), 1,461 (w), 1,253 (w), 1,137 (s), 842 (m), 732 (w).
Elementary Analysis:
Calculated for C$_8$H$_{24}$B$_{10}$O$_1$: C=39.32% H=9.90%.
Found: C=40.10% H=9.74%.

Embodiment 2

1-((7-Hydroxy)-1,7-dicarba-closo-dodecaboran(12)yl)-hexan-1-ol

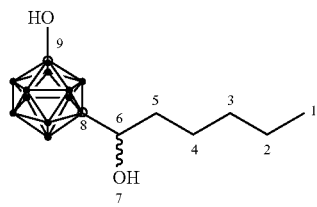

2.7 ml (1.64 M in n-hexane, 4.47 mmol, 2.2 eq.) of an n-butyl lithium solution is carefully dropped into a solution of 0.50 g (2.03 mmol, 1.0 eq.) of 1-(1,7-dicarba-closo-dodecaboran(12)yl)-hexan-1-ol in 20 ml of diethyl ether at 0° C. The clear solution is then heated to room temperature. After three hours, said solution is cooled to −30° C., and 0.28 ml (0.25 g, 2.44 mmol, 1.2 eq.) of boric acid trimethyl ester is dropped in. The solution is heated to room temperature. Within 24 hours, a colourless, highly viscous substance is formed. Said substance is cooled to 0° C., to which 2.0 ml (32% in acetic acid, 0.64 g, 8.41 mmol, 4.1 eq.) of peracetic acid is added. After 24 hours, at room temperature, 2.0 ml of concentrated sodium hydroxide solution is dropped in. 20 ml of distilled water is added to the resultant clear solution after two hours. Extraction is carried out three times by means of 20 ml of diethyl ether on each occasion, and the combined organic phases are washed by means of 20 ml of saturated sodium chloride solution. Drying is then carried out by means of magnesium sulfate, and the solvent is removed under reduced pressure. The residue is purified by column chromatography (eluent: n-hexane/ethyl acetate 5:1 v/v). A colourless solid is obtained.

Yield: 0.27 g (1.05 mmol, 52%)
$R_f$ value: 0.29 (eluent: n-hexane/ethyl acetate 5:1 v/v)
Melting point: 68.3-68.8° C.
$^1$H NMR (CDCl$_3$): δ=0.89 (t, 3H, 1-CH$_3$, $^3J_{HH}$=6.7 Hz), 1.17-3.40 (br m, 10H, BH), 1.27 (m, 8H, 2,3,4-CH$_2$), 1.55 (m, 2H, 5-CH$_2$), 1.94 (d, 1H, 6-OH, $^3J_{HH}$=5.9 Hz), 3.74 (d, 1H, 6-CH, $^3J_{HH}$=7.8 Hz), 3.91 (s, 1H, 7-OH) ppm.
$^{11}$B{$^1$H} NMR (CDCl$_3$): δ=−14.8 (s, 4B, BH), −13.6 (s, 3B, BH), −11.6 (s, 2B, BH), −6.5 (s, 1B, BH) ppm.
$^{13}$C{$^1$H} NMR (CDCl$_3$): δ=14.0 (s, 1-CH$_3$), 22.5 (s, 2-CH$_2$), 26.1 (s, 4-CH$_2$), 31.3 (s, 3-CH$_2$), 37.3 (s, 5-CH$_2$), 72.5 (s, 6-CH), 79.1 (s, 8-C$_q$), 100.9 (s, 9-C$_q$) ppm.
Mass spectrometry (ESI neg., CH$_2$Cl$_2$/CH$_3$OH):
Calculated: m/z=260.3.
Determined: m/z=259.2 (100%, [M−H]$^-$).
IR spectroscopy (KBr, ṽ in cm$^{-1}$): 3,424 (s), 2,959 (m), 2,929 (m), 2,603 (s), 1,635 (m), 1,459 (w), 1,261 (m), 1,205 (m), 1,082 (m) 1,025 (m), 803 (m).
Elementary Analysis:
Calculated for C$_8$H$_{24}$B$_{10}$O$_2$: C=36.90% H=9.29%.
Found: C=37.00% H=9.33%.

Embodiment 3

1-((7-Quinolin-2-ylmethoxy)-1,7-dicarba-closo-dodecaboran(12)yl)-hexan-1-ol—Compound 1

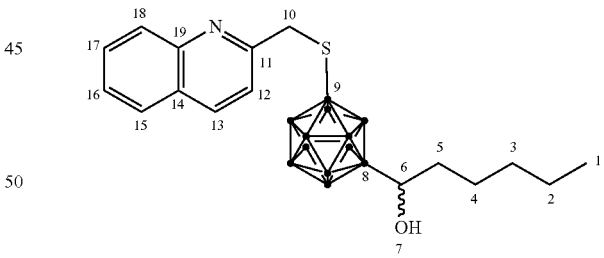

Figure 7:
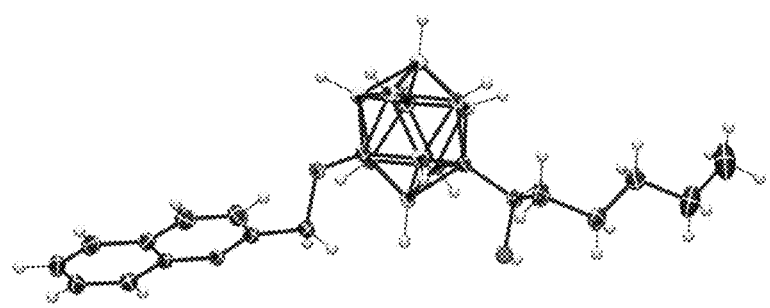
FIG. 7 is a diagram illustrating the 3D chemical structure of 1-((7-Quinolin-2-ylmethoxy)-1,7-dicarba-closo-dodecaboran(12)yl)-hexan-1-ol.

See FIG. 7 for the 3D chemical structure.

24.2 mg (1.0 mmol, 1.0 eq.) of sodium hydride is added to a solution of 0.26 g (1.0 mmol, 1.0 eq.) of 1-(7-hydroxy-1,7-dicarba-closo-dodecaboran(12)yl)-hexan-1-ol in 20 ml of dry tetrahydrofuran at room temperature. 0.25 g (1.1 mmol, 1.1 eq.) of quinaldine bromide is added to the clear solution after four hours, and the solution is heated to 55° C. for 24 hours. 20 ml of distilled water is then added, and extraction is carried out three times by means of 20 ml of diethyl ether on each occasion. The combined organic phases are washed by means of 20 ml of saturated sodium chloride solution and dried by means of magnesium sulfate. The solvent is removed under reduced pressure, and the highly viscous residue is purified by column chromatography (eluent: n-hexane/ethyl acetate, 5:1 v/v). A colourless solid is obtained.

Yield: 122 mg (34%)

$R_f$ value: 0.48 (eluent: n-hexane/ethyl acetate 5:1 v/v)

Melting point: 86.6-87.5° C.

$^1$H NMR (CDCl$_3$): δ=0.87 (t, 3H, 1-CH$_3$, $^3J_{HH}$=6.7 Hz), 1.18-3.62 (br m, 10H, BH), 1.27 (m, 2H, 3-CH$_2$), 1.28 (m, 2H, 2-CH$_2$), 1.39 (m, 2H, 5-CH$_2$), 1.56 (m, 2H, 4-CH$_2$), 2.47 (br s, 1H, 7-OH), 3.75 (br d, 1H, 6-CH, $^3J_{HH}$=8.9 Hz), 4.84 (s, 2H, 10-CH$_2$), 7.44 (d, 1H, 12-CH, $^3J_{HH}$=8.5 Hz), 7.55 (t, 1H, 16-CH, $^3J_{HH}$=8.6 Hz), 7.71 (t, 1H, 17-CH, $^3J_{HH}$=8.5 Hz), 7.80 (d, 1H, 15-CH, $^3J_{HH}$=8.0 Hz), 8.02 (d, 1H, 18-CH, $^3J_{HH}$=8.9 Hz), 8.16 (d, 1H, 13-CH, $^3J_{HH}$=8.5 Hz) ppm.

$^{11}$B{$^1$H} NMR (CDCl$_3$): δ=−14.9 (s, 4B, BH), −13.7 (s, 3B, BH), −12.7 (s, 2B, BH), −7.8 (s, 1B, BH) ppm.

$^{13}$C{$^1$H} NMR (CDCl$_3$): δ=14.0 (s, 1-CH$_3$), 22.5 (s, 2-CH$_2$), 26.2 (s, 4-CH$_2$), 31.3 (s, 3-CH$_2$), 37.3 (s, 5-CH$_2$), 72.5 (s, 6-CH), 76.5 (s, 10-CH$_2$), 78.4 (s, 8-C$_q$), 106.3 (s, 9-C$_q$), 119.0 (s, 12-CH), 126.7 (s, 16-CH), 127.6 (s, 14-C$_q$), 127.7 (s, 15-CH), 128.9 (s, 18-CH), 129.9 (s, 17-CH), 137.0 (s, 13-CH), 147.2 (s, 19-C$_q$), 156.1 (s, 11-C$_q$) ppm.

Mass spectrometry (ESI pos., CH$_2$CO$_2$/CH$_3$OH):

Calculated: m/z=401.3.

Determined: m/z=402.4 (100%, [M+H]$^+$), 423.4 (21%, [M+Na]$^+$), 440.3 (24%, [M+K]*).

IR spectroscopy (KBr, ṽ in cm$^{-1}$): 3,165 (m), 2,955 (m), 2,933 (m), 1,601 (w), 1,508 (m), 1,464 (w), 1,429 (w), 1,380 (w), 1,319 (w), 1,197 (s), 1,142 (m), 1,036 (s), 824 (m), 762 (m), 740 (m), 477 (w).

Elementary Analysis:

Calculated for C$_{18}$H$_{31}$B$_{10}$N$_1$O$_2$: C=53.84% H=7.78% N=3.49%.

Found: C=54.80% H=7.91% N=3.44%.

X-Ray Crystal Structure Analysis

| Empirical formula | C$_{18}$H$_{31}$B$_{10}$N$_1$O$_2$ |
| --- | --- |
| Formula weight | 401.54 |
| Temperature | 130(2) K |
| Wavelength | 71.073 pm |
| Crystal system | triclinic |
| Space group | P-1 |
| Lattice constants | a = 722.51(7) pm   α = 71.713(7)°. |
| | b = 1,268.63(8) pm  β = 81.786(7)°. |
| | c = 1,311.04(11) pm γ = 83.030(7)°. |
| Cell volume | 1.12555(17) nm$^3$ |
| Number of formula units | 2 |
| Density (calculated) | 1.185 mg/m$^3$ |
| Absorption coefficient | 0.067 mm$^{-1}$ |
| F(000) | 424 |
| Size of the crystal | 0.7 × 0.2 × 0.05 mm$^3$ |
| Measurement range of θ | 1.975 to 32.522°. |
| Index ranges | −10 ≤ h ≤ 10, −18 ≤ k ≤ 18, |
| | −19 ≤ l ≤ 19 |
| Measured reflections | 17,867 |
| Independent reflections | 7,406 [R(int) = 0.0450] |
| Completeness up to θ = 30.510° | 100.0% |
| Absorption correction | semi-empirical from equivalents |
| Max. and min. transmission | 1 and 0.82496 |
| Refinement method | full-matrix least-squares on F$^2$ |
| Data/restraints/parameters | 7,406/76/386 |
| Goodness-of-fit on F$^2$ | 1.016 |
| R values [I > 2σ(I)] | R1 = 0.0635, wR2 = 0.1412 |
| R values (all reflections) | R1 = 0.1189, wR2 = 0.1686 |
| Max. and min. residual electron density | 0.296 and −0.237 e · Å−3 |

Embodiment 4

1-(7-(Hexan-1-olyl)-1,7-dicarba-closo-dodecaboran(12)yl)-thiol

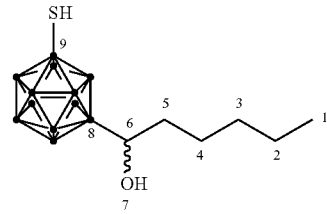

2.7 ml (1.64 M in n-hexane, 4.47 mmol, 2.2 eq.) of an n-butyl lithium solution is carefully dropped into a solution of 0.50 g (2.03 mmol, 1.0 eq.) of 1-(1,7-dicarba-closo-dodecaboran(12)yl)-hexan-1-ol in 20 ml of diethyl ether at 0° C. The clear solution is then heated to room temperature. After three hours, said solution is cooled again to 0° C., and 71.5 mg (2.23 mmol, 1.1 eq.) of sulfur is added. The solution is heated to room temperature, to which 20 ml of distilled water is added after 24 hours. Extraction is carried out three times by means of 20 ml of diethyl ether on each occasion, and the combined organic phases are washed by means of 20 ml of saturated sodium chloride solution. Drying is then carried out by means of magnesium sulfate, and the solvent is removed under reduced pressure. The resultant highly viscous residue is recrystallised from n-hexane, and the product is obtained as a colourless solid.

Yield: 0.55 g (98%)

$R_f$ value: 0.65 (eluent: n-hexane/ethyl acetate 5:1 v/v)

Melting point: 51.8-52.3° C.

$^1$H NMR (CDCl$_3$): δ=0.89 (t, 3H, 1-CH$_3$, $^3J_{HH}$=7.0 Hz), 1.10-3.20 (m, 10H, BH), 1.28 (m, 6H, 2,3,4-CH$_2$), 1.55 (m, 2H, 5-CH$_2$), 1.82 (d, 1H, 7-OH, $^3J_{HH}$=6.9 Hz), 3.39 (S, 1H, 9-SH), 3.75 (br t, 1H, 6-CH, $^3J_{HH}$=7.3 Hz) ppm.

$^{11}$B{$^1$H} NMR (CDCl$_3$): δ=−12.9 (s, 2B, BH), −12.1 (s, 2B, BH), −10.6 (s, 2B, BH), −9.1 (s, 2B, BH), −4.0 (s, 1B, BH) ppm.

$^{13}$C{$^1$H} NMR (CDCl$_3$): δ=14.0 (s, 1-CH$_3$), 22.5 (s, 2-CH$_2$), 26.12 (s, 4-CH$_2$), 31.3 (s, 3-CH$_2$), 37.3 (s, 5-CH$_2$), 63.5 (s, 8-C$_q$), 72.7 (s, 6-CH), 84.2 (s, 9-C$_q$) ppm.

Mass spectrometry (ESI neg., CH$_2$Cl$_2$/CH$_3$OH):

Calculated: m/z=276.3.

Determined: m/z=275.3 (100%, [M−H]$^−$).

IR spectroscopy (KBr, ṽ in cm$^{-1}$): 3,407 (s), 2,957 (m), 2,928 (m), 2,602 (s), 1,639 (m), 1,156 (m), 1,125 (m), 1,078 (m), 735 (m), 611 (w).

Elementary Analysis:

Calculated for C$_8$H$_{24}$B$_{10}$O$_1$S$_1$: C=34.76% H=8.75%.

Found: C=34.89% H=8.47%.

Embodiment 5

1-(7-Thiomethylquinolin-2-yl-1,7-dicarba-closo-dodecaboran(12)yl)-hexan-1-ol

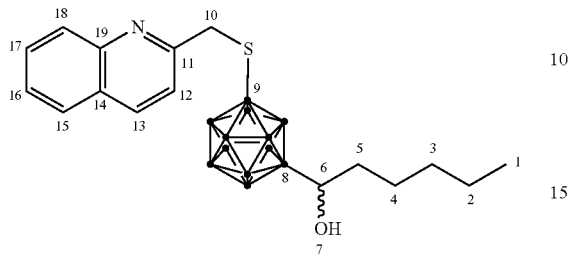

0.48 ml (1.64 M in n-hexane, 0.79 mmol, 1.0 eq.) of an n-butyl lithium solution is carefully dropped into a solution of 220 mg (0.79 mmol, 1.0 eq.) of 1-(7-(hexan-1-olyl)-1,7-dicarba-closo-dodecaboran(12)yl)-thiol in 20 ml of diethyl ether at 0° C. in inert conditions. After 30 minutes, the solution is heated to room temperature. After three hours, the solution is cooled to −50° C., to which 175.7 mg (0.79 mmol, 1.0 eq.) of 2-bromomethyl quinoline is added. The solution is then heated to room temperature. After 24 hours, a yellow precipitate has formed. 20 ml of distilled water is added to the suspension, which is then extracted three times by means of 20 ml of diethyl ether on each occasion. The combined organic phases are washed by means of 20 ml of saturated sodium chloride solution and dried by means of magnesium sulfate, and the solvent is then removed under reduced pressure. The residue is purified by column chromatography (eluent: n-hexane/ethyl acetate 5:1 v/v). A slightly yellowish liquid is obtained.

Yield: 166 mg (51%)

$R_f$ value: 0.36 (eluent: n-hexane/ethyl acetate 5:1 v/v)

$^1$H NMR (CDCl$_3$): δ=0.87 (t, 3H, 1-CH$_3$, $^3J_{HH}$=7.0 Hz), 1.25 (br m, 4H, 3,4-CH$_2$), 1.26-3.47 (br m, 10H, BH), 1.34 (m, 2H, 2-CH$_2$), 1.51 (m, 2H, 5-CH$_2$), 2.52 (br s, 2H, 7-OH), 3.74 (brt, 1H, 6-CH, $^3J_{HH}$=8.7 Hz), 4.30 (S, 2H, 10-CH$_2$), 7.45 (d, 1H, 12-CH, $^3J_{HH}$=8.7 Hz), 7.52 (t, 1H, 17-CH, $^3J_{HH}$=8.0 Hz), 7.69 (t, 1H, 16-CH, $^3J_{HH}$=8.0 Hz), 7.77 (d, 1H, 15-CH, $^3J_{HH}$=8.7 Hz), 8.04 (d, 1H, 18-CH, $^3J_{HH}$=8.0 Hz), 8.10 (d, 1H, 13-CH, $^3J_{HH}$=8.0 Hz) ppm.

$^{11}$B{$^1$H} NMR (CDCl$_3$): δ=−13.6 (s, 2B, BH), −12.2 (s, 2B, BH), −11.0 (s, 4B, BH), −7.8 (s, 1B, BH), −5.4 (s, 1B, BH) ppm.

$^{13}$C{$^1$H} NMR (CDCl$_3$): δ=14.0 (s, 1-CH$_3$), 22.5 (s, 2-CH$_2$), 26.2 (s, 4-CH$_2$), 31.1 (s, 3-CH$_2$), 37.3 (s, 5-CH$_2$), 43.2 (s, 10-CH$_2$), 71.2 (s, 9-C$_q$), 72.6 (s, 6-CH), 83.3 (s, 8-C$_q$), 120.8 (s, 12-CH), 126.8 (s, 17-CH), 127.1 (s, 19-C$_q$), 127.6 (s, 15-CH), 128.9 (s, 18-CH), 129.9 (s, 16-CH), 137.0 (s, 13-CH), 147.6 (s, 14-CH), 155.5 (s, 11-CH) ppm.

Mass spectrometry (ESI pos., CH$_2$Cl$_2$/CH$_3$OH):

Calculated: m/z=417.3.

Determined: m/z=418.4 (100%, [M+H]$^+$), 441.4 (50%, [M+Na]$^+$), 456.3 (45%, [M+K]$^+$).

IR spectroscopy (KBr, ṽ in cm$^{-1}$): 3,434 (s), 2,963 (m), 2,600 (w), 1,631 (w), 1,262 (s), 1,096 (s), 1,022 (s), 865 (w), 802 (s), 704 (w).

Elementary Analysis:

Calculated for C$_7$H$_{20}$B$_{10}$O$_2$: C=51.77% H=7.48% N=3.35%.

Found: C=51.60% H=7.25% N=3.13%.

Embodiment 6

1-(Tetrahydro-2H-pyran-4-olyl)-1,7-dicarba-closo-dodecaborane(12)

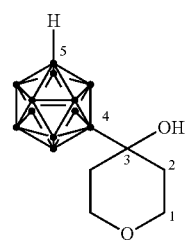

2.0 g (13.7 mmol, 1.0 eq.) of 1,7-dicarba-closo-dodecaborane(12) is dissolved in 60 ml of diethyl ether, to which 9.78 ml (1.54 M in n-hexane, 15.1 mmol, 1.1 eq.) of n-butyl lithium is added at 0° C. and which is then heated to room temperature. After three hours, the solution is cooled to 0° C., to which 1.27 ml (1.37 g, 13.7 mmol, 1.0 eq.) of tetrahydro-2H-pyranone is added. Said solution is then heated to room temperature. After 24 hours, 30 ml of distilled water is added to the obtained white suspension, and the resultant phases are separated. The organic phase is then extracted by means of 20 ml of 10% sodium hydroxide solution, and the combined aqueous phases are acidulated by means of concentrated hydrochloric acid and extracted three times by means of 20 ml of diethyl ether on each occasion. The combined organic phases are dried by means of magnesium sulfate, and the solvent is removed under reduced pressure. The residue is recrystallised from n-hexane, and the product is obtained as a colourless solid.

Yield: 2.86 g (11.6 mmol, 85%)

$R_f$ value: 0.32 (eluent: n-hexane/ethyl acetate 5:2 v/v)

Melting point: 109.0-110.2° C.

$^1$H NMR (CDCl$_3$): δ=1.50-3.20 (br m, 10H, BH), 1.53 (d, 2H, chair-2-CH$_2$, $^3J_{HH}$=13.3 Hz), 1.82 (dt, 2H, boat-2-CH$_2$, $^3J_{HH}$=13.0 Hz), 2.92 (br s, 1H, 5-CH), 3.66 (t, 2H, chair-1-CH$_2$, $^3J_{HH}$=12.2 Hz), 3.80 (dd, 2H, boat-1-CH$_2$, $^3J_{HH}$=11.0 Hz) ppm.

$^{11}$B{$^1$H} NMR (CDCl$_3$): δ=−15.8 (s, 5B, BH), −13.1 (s, 2B, BH), −11.3 (s, 2B, BH), −4.6 (s, 1B, BH) ppm.

$^{13}$C{$^1$H} NMR (CDCl$_3$): δ=39.3 (s, 2-CH$_2$), 53.9 (s, 5-CH), 63.8 (s, 1-CH$_2$), 69.3 (s, 3-C$_q$), 69.4 (s, 5-C$_q$) ppm.

Mass spectrometry (ESI neg., acetone):

Calculated: m/z=244.3

Determined: m/z=243.2 (100%, [M−H]$^-$), 216.2 (22%, [M−C$_2$H$_5$]$^-$).

IR spectroscopy (KBr, ṽ in cm$^{-1}$): 3,430 (s), 3,062 (w), 2,964 (w), 2,934 (w), 2,864 (w), 2,600 (s), 1,468 (w), 1,387 (w), 1,356 (w), 1,159 (m), 1,123 (m), 1,022 (m), 852 (w), 732 (w), 550 (m).

Elementary Analysis:

Calculated for C$_7$H$_{20}$B$_{10}$O$_2$: C=34.41% H=8.25%.

Found: C=34.28% H=8.27%.

Embodiment 7

1-Mercapto-7-(tetrahydro-2H-pyran-4-olyl)-1,7-dicarba-closo-dodecaborane(12)

Figure 8:
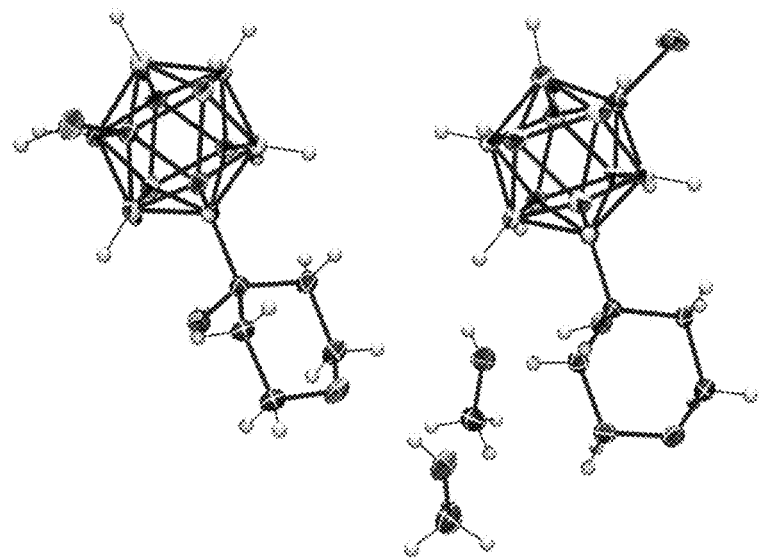
FIG. 8 is a diagram illustrating the 3D chemical structure of 1-Mercapto-7-(tetrahydro-2H-pyran-4-olyl)-1,7-dicarba-ciso-dodecaborane(12).

See FIG. 8 for the 3D chemical structure.

1.5 g (8.42 mmol, 1.0 eq.) of 1-thio-1,7-dicarba-closo-dodecaborane(12) is dissolved in 50 ml of diethyl ether, to which 11.50 ml (1.54 M in n-hexane, 17.71 mmol, 2.1 eq.) of n-butyl lithium is added at 0° C. and which is then heated to room temperature. After three hours, the obtained suspension is cooled to 0° C., to which 0.78 ml (0.84 g, 8.42 mmol, 1.0 eq.) of tetrahydro-2H-pyranone is added. Said suspension is then heated to room temperature. After 24 hours, 20 ml of distilled water is added to the obtained white suspension, which is acidulated by means of concentrated hydrochloric acid and extracted three times by means of 20 ml of diethyl ether on each occasion. The combined organic phases are dried by means of magnesium sulfate, and the solvent is removed under reduced pressure. The residue is applied to silica gel, and the starting material is separated (eluent: n-hexane/ethyl acetate 10:1 v/v). The product is then eluted by means of ethyl acetate, the solvent is removed under reduced pressure, and the residue is recrystallised from n-hexane/methanol (20:1 v/v). A colourless solid is obtained.

Yield: 1.15 g (4.13 mmol, 49%)

$R_f$ value: 0.32 (eluent: n-hexane/ethyl acetate 5:2 v/v)

Melting point: 91.2-92.3° C.

$^1$H NMR (CDCl$_3$): δ=1.45-3.80 (br m, 10H, BH), 1.53 (d, 2H, chair-2-CH$_2$, $^3J_{HH}$=13.8 Hz), 1.61 (br s, 1H, 5-SH), 1.83 (dt, 2H, boat-2-CH$_2$, $^3J_{HH}$=13.1 Hz), 3.66 (dt, 2H, chair-1-CH$_2$, $^3J_{HH}$=11.6 Hz), 3.81 (dd, 2H, boat-1-CH$_2$, $^3J_{HH}$=11.6 Hz) ppm.

$^{11}$B{$^1$H} NMR (CDCl$_3$): δ=−12.8 (s, 2B, BH), −12.4 (s, 2B, BH), −10.5 (s, 2B, BH), −9.0 (s, 3B, BH), −3.2 (s, 1B, BH) ppm.

$^{13}$C{$^1$H} NMR (CDCl$_3$): δ=39.3 (s, 2-CH$_2$), 42.8 (s, 5-C$_q$), 63.7 (s, 1-CH$_2$), 67.8 (s, 4-C$_q$), 69.5 (s, 3-C$_q$) ppm.

Mass spectrometry (ESI neg., CHCl$_3$, CH$_3$OH):

Calculated: m/z=276.2

Determined: m/z=275.2 (100%, [M−H]$^-$).

IR spectroscopy (KBr, $\tilde{v}$ in cm$^{-1}$): 3,347 (s), 2,974 (m), 2,952 (s), 2,941 (m), 2,865 (s), 2,634 (s), 2,571 (s), 2,557 (s), 1,406 (m), 1,388 (m), 1,355 (m), 1,305 (m), 1,249 (m), 1,161 (s), 1,138 (s), 1,102 (s), 1,019 (s), 973 (m), 849 (m), 739 (w), 553 (s).

Elementary Analysis:

Calculated for C$_7$H$_{20}$B$_{10}$O$_2$S$_1$: C=30.42% H=7.29%.

Found: C=30.68% H=7.31%.

X-Ray Crystal Structure Analysis

| | |
|---|---|
| Empirical formula | C$_8$H$_{24}$B$_{10}$O$_3$S$_1$ |
| Formula weight | 308.43 |
| Temperature | 130(2) K |
| Wavelength | 71.073 pm |
| Crystal system | triclinic |
| Space group | P-1 |
| Lattice constant | a = 760.23(5) pm    α = 85.472(4)°. |
| | b = 969.71(5) pm    β = 84.192(4)°. |
| | c = 2,324.27(10) pm    γ = 73.010(5)°. |
| Cell volume | 1.62807(16) nm$^3$ |
| Number of formula units | 4 |
| Density (calculated) | 1.258 mg/m$^3$ |
| Absorption coefficient | 0.197 mm$^{-1}$ |
| F(000) | 648 |
| Size of the crystal | 0.4 × 0.1 × 0.1 mm$^3$ |
| Measurement range of θ | 2.199 to 30.512°. |
| Index ranges | −10 ≤ h ≤ 10, −13 ≤ k ≤ 13, −31 ≤ l ≤ 32 |
| Measured reflections | 29,901 |
| Independent reflections | 8,982 [R(int) = 0.0531] |
| Completeness up to θ = 28.285° | 100.0% |
| Absorption correction | semi-empirical from equivalents |
| Max. and min. transmission | 1 and 0.97336 |
| Refinement method | full-matrix least-squares on F$^2$ |
| Data/restraints/parameters | 8,982/0/589 |
| Goodness-of-fit on F$^2$ | 1.019 |
| R values [I > 2σ(I)] | R1 = 0.0505, wR2 = 0.1025 |
| R values (all reflections) | R1 = 0.0855, wR2 = 0.1155 |
| Extinction coefficient | n/a |
| Max. and min. residual electron density | 0.354 and −0.307 e · Å−3 |

Embodiment 8

1-(2-Mercaptomethyl)quinolyl-7-(tetrahydro-2H-pyran-4-olyl)-1,7-dicarba-closo-dodecaborane(12)

Figure 9:
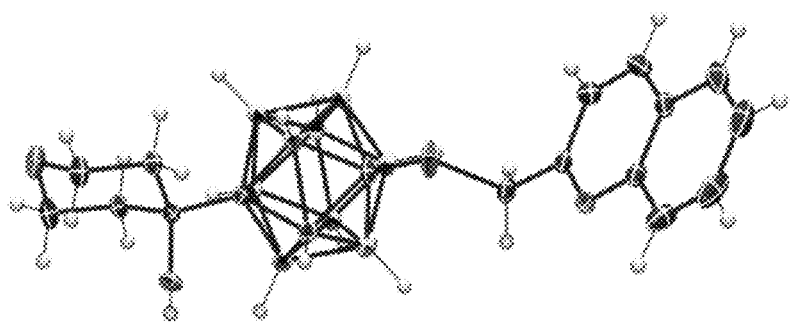
FIG. 9 is a diagram illustrating the 3D chemical structure of 1-(2-Mercaptomethyl)quinolyl-7-(tetrahydro-2H-pyran-4-olyl)-1,7-dicarba-closo-dodecaborane(12).

See FIG. 9 for the 3D chemical structure.

450.0 mg (3.24 mmol, 3.0 eq.) of potassium carbonate is added to a solution of 1-mercapto-7-(tetrahydro-2H-pyran-4-olyl)-1,7-dicarba-closo-dodecaborane(12) (0.3 g, 1.08 mmol, 1.0 eq.) and 2-bromomethyl quinoline (240.0 mg, 1.08 mmol, 1.0 eq.) in 30 ml of acetone at room temperature, and then heated under reflux for 24 hours. After being cooled to room temperature, 20 ml of distilled water and 10 ml of saturated sodium chloride solution are added. Extraction is carried out three times by means of 20 ml of diethyl ether on each occasion, the organic phases are combined, and dried by means of magnesium sulfate, and the solvent is removed under reduced pressure. The raw product is purified by column chromatography (eluent: n-hexane/ethyl acetate 5:1 v/v). The product is obtained as a slightly yellowish solid.

Yield: 246 mg (0.59 mmol, 54%)

$R_f$ value: 0.20 (eluent: n-hexane/ethyl acetate 5:1 v/v)

Melting point: 91.8-92.5° C.

$^1$H NMR (CDCl$_3$): δ=1.20-3.70 (br m, 10H, BH), 1.49 (d, 2H, chair-2-CH$_2$, $^3J_{HH}$=13.3 Hz), 1.76 (dt, 2H, boat-2-

CH$_2$, $^3J_{HH}$=12.8 Hz), 1.93 (s, 1H, 3-OH), 3.63 (t, 2H, chair-1-CH$_2$, $^3J_{HH}$=11.1 Hz), 3.76 (dd, 2H, boat-1-CH$_2$, $^3J_{HH}$=11.6 Hz), 4.30 (s, 2H, 6-CH$_2$), 7.46 (d, 1H, 8-CH, $^3J_{HH}$=8.5 Hz), 7.53 (t, 1H, 12-CH, $^3J_{HH}$=8.0 Hz), 7.71 (t, 1H, 13-CH, $^3J_{HH}$=7.4 Hz), 7.79 (d, 2H, 11-CH, $^3J_{HH}$=8.4 Hz), 8.05 (d, 1H, 14-CH, $^3J_{HH}$=8.4 Hz), 8.13 (d, 1H, 9-CH, $^3J_{HH}$=8.5 Hz) ppm.

$^{11}$B{$^1$H} NMR (CDCl$_3$): δ=−13.6 (s, 2B, BH), −12.6 (s, 2B, BH), −11.0 (s, 4B, BH), −8.2 (s, 1B, BH), −4.6 (s, 1B, BH) ppm.

$^{13}$C{$^1$H} NMR (CDCl$_3$): δ=39.3 (s, 2-CH$_2$), 43.2 (s, 6-CH$_2$), 63.8 (s, 1-CH$_2$), 69.4 (s, 3-C$_q$), 70.9 (s, 5-C$_q$), 88.4 (s, 4-C$_q$), 120.8 (s, 8-CH), 126.8 (s, 12-CH), 127.2 (s, 10-C$_q$), 127.6 (s, 11-CH), 129.0 (s, 14-CH), 129.9 (s, 13-CH), 137.0 (s, 9-CH), 147.6 (s, 15-C$_q$), 155.6 (s, 7-C$_q$) ppm.

Mass spectrometry (ESI neg., CH$_2$Cl$_2$, CH$_3$CN):

Calculated: m/z=417.3

Determined: m/z=416.3 (100%, [M−H]$^-$).

IR spectroscopy (KBr, ṽ in cm$^{-1}$): 3,427 (s), 2,962 (w), 2,870 (w), 2,606 (s), 1,619 (m), 1,599 (m), 1,505 (m), 1,427 (m), 1,304 (w), 1,244 (w), 1,160 (m), 1,019 (m), 822 (m), 766 (m), 547 (m).

Elementary Analysis:

Calculated for C$_{17}$H$_{27}$B$_{10}$N$_1$O$_2$S$_1$: C=48.90% H=6.52% N=3.35%.

Found: C=50.64% H=6.53% N=3.60%.

X-Ray Crystal Structure Analysis

| Empirical formula | C$_{17}$H$_{27}$B$_{10}$N$_1$O$_2$S$_1$ |
| --- | --- |
| Formula weight | 417.55 |
| Temperature | 130(2) K |
| Wavelength | 71.073 pm |
| Crystal system | monoclinic |
| Space group | P 21/n |
| Lattice constant | a = 964.84(4) pm   α = 90°. |
| | b = 1,816.00(6) pm  β = 102.951(3)°. |
| | c = 1,270.03(4) pm  γ = 90°. |
| Cell volume | 2.16868(14) nm$^3$ |
| Number of formula units | 4 |
| Density (calculated) | 1.279 mg/m$^3$ |
| Absorption coefficient | 0.165 mm$^{-1}$ |
| F(000) | 872 |
| Size of the crystal | 0.4 × 0.15 × 0.1 mm$^3$ |
| Measurement range of θ | 1.991 to 32.567°. |
| Index ranges | −14 ≤ h ≤ 14, −27 ≤ k ≤ 26, −19 ≤ l ≤ 18 |
| Measured reflections | 47,840 |
| Independent reflections | 7,494 [R(int) = 0.0477] |
| Completeness up to θ = 30.510° | 100.0% |
| Absorption correction | semi-empirical from equivalents |
| Max. and min. transmission | 1 and 0.96721 |
| Refinement method | full-matrix least-squares on F$^2$ |
| Data/restraints/parameters | 7,494/0/388 |
| Goodness-of-fit on F$^2$ | 1.013 |
| R values [I > 2σ(I)] | R1 = 0.0436, wR2 = 0.0932 |
| R values (all reflections) | R1 = 0.0663, wR2 = 0.1018 |
| Max. and min. residual electron density | 0.307 and −0.384 e · Å$^{-3}$ |

Embodiment 9

1-(2-Mercaptomethyl)naphthyl-7-(tetrahydro-2H-pyran-4-olyl)-1,7-dicarba-closo-dodecaborane(12)—Compound 2

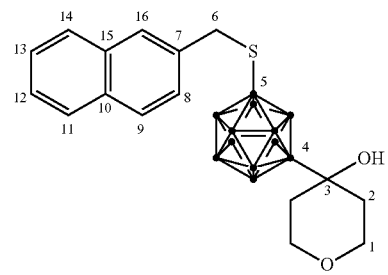

Figure 10:
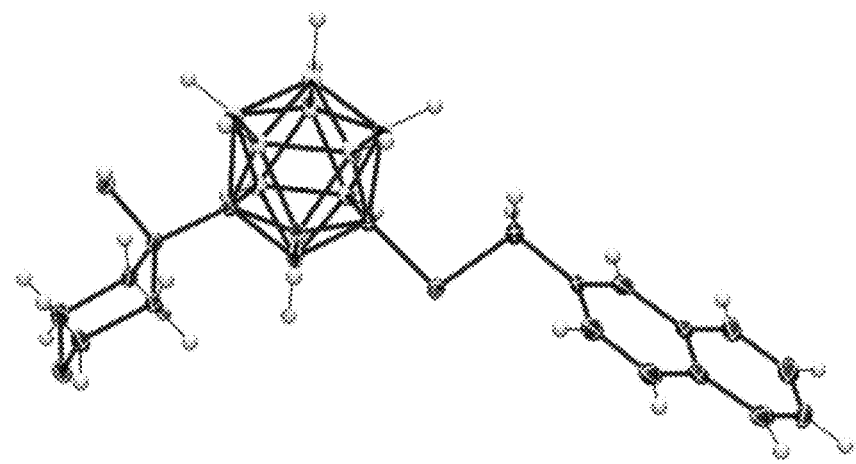
FIG. 10 is a diagram illustrating the 3D chemical structure of 1-(2-Mercaptomethyl)naphthyl-7-(tetrahydro-2H-pyran-4-olyl)-1,7-dicarba-closo-dodecaborane(12)—Compound 2.

See FIG. 10 for the 3D chemical structure.

373.0 mg (2.70 mmol, 3.0 eq.) of potassium carbonate is added to a solution of 1-mercapto-7-(tetrahydro-2H-pyran-4-olyl)-1,7-dicarba-closo-dodecaborane(12) (0.25 g, 0.90 mmol, 1.0 eq.) and 2-bromomethyl naphthalene (197.0 mg, 0.90 mmol, 1.0 eq.) in 50 ml of acetone at room temperature, and then heated under reflux for 24 hours. After being cooled to room temperature, 20 ml of distilled water and 10 ml of saturated sodium chloride solution are added. Extraction is carried out three times by means of 20 ml of diethyl ether on each occasion, the organic phases are combined, and dried by means of magnesium sulfate, and the solvent is removed under reduced pressure. The raw product is purified by column chromatography (eluent: n-hexane/ethyl acetate 5:1 v/v). The product is obtained as a colourless solid.

Yield: 184 mg (0.44 mmol, 49%)

R$_f$ value: 0.44 (eluent: n-hexane/ethyl acetate 5:2 v/v)

Melting point: 100.5-101.3° C.

$^1$H NMR (CDCl$_3$): δ=1.10-3.70 (br m, 10H, BH), 1.52 (d, 2H, seat-2-CH$_2$, $^3J_{HH}$=13.4 Hz), 1.63 (br s, 1H, 3-OH), 1.82 (dt, 2H, boat-2-CH$_2$, $^3J_{HH}$=13.1 Hz), 3.67 (dt, 2H, seat-1-CH$_2$, $^3J_{HH}$=11.6 Hz), 3.81 (dd, 2H, boat-1-CH$_2$, $^3J_{HH}$=11.6 Hz), 4.14 (s, 2H, 6-CH$_2$), 7.39 (d, 1H, 8-CH, $^3J_{HH}$=8.5 Hz), 7.48 (t, 1H, 13-CH, $^3J_{HH}$=9.0 Hz), 7.49 (t, 1H, 12-CH, $^3J_{HH}$=9.7 Hz), 7.75 (s, 1H, 16-CH), 7.80 (d, 1H, 9-CH, $^3J_{HH}$=8.5 Hz), 7.81 (d, 1H, 14-CH, $^3J_{HH}$=8.4 Hz), 7.82 (d, 1H, 11-CH, $^3J_{HH}$=8.5 Hz) ppm.

$^{11}$B{$^1$H} NMR (CDCl$_3$): δ=−13.6 (s, 2B, BH), −12.6 (s, 2B, BH), −10.9 (s, 4B, BH), −8.2 (s, 1B, BH), −4.5 (s, 1B, BH) ppm.

$^{13}$C{$^1$H} NMR (CDCl$_3$): δ=39.3 (s, 2-CH$_2$), 41.1 (s, 6-CH$_2$), 63.7 (s, 1-CH$_2$), 69.4 (s, 3-C$_q$), 71.3 (s, 5-C$_q$), 88.0 (s, 4-C$_q$), 126.2 (s, 12-CH), 126.3 (s, 13-CH), 126.8 (s, 8-CH), 127.6 (s, 9-CH, 14-CH), 128.2 (s, 16-CH), 128.5 (s, 11-CH), 131.6 (s, 7-C$_q$), 132.7 (s, 10-C$_q$), 133.2 (s, 15-C$_q$) ppm.

Mass spectrometry (ESI neg., acetone):

Calculated: m/z=416.3

Determined: m/z=415.3 (100%, [M−H]$^-$), 452.2 (50%, [M+Cl]$^-$).

IR spectroscopy (KBr, ṽ in cm$^{-1}$): 3,472 (s), 2,957 (s), 2,979 (m), 2,957 (m), 2,918 (m), 2,865 (m), 2,598 (s), 1,508 (w), 1,464 (w), 1,437 (w), 1,390 (m), 1,361 (m), 1,303 (m), 1,243 (m), 1,159 (m), 1,124 (s), 1,102 (s), 1,019 (s), 973 (m), 848 (m), 822 (s), 755 (s), 549 (m), 472 (m).

Elementary Analysis:
Calculated for $C_{18}H_{28}B_{10}O_2S_1$: C=51.90% H=6.77%.
Found: C=53.23% H=6.92%.
X-Ray Crystal Structure Analysis

| | |
|---|---|
| Empirical formula | $C_{18}H_{31}B_{10}O_{3.5}S_1$ |
| Formula weight | 443.59 |
| Temperature | 130(2) K |
| Wavelength | 71.073 pm |
| Crystal system | monoclinic |
| Space group | P 21/c |
| Lattice constant | a = 1,428.01(4) pm   α = 90°. |
| | b = 660.10(2) pm   β = 94.490(3)°. |
| | c = 5,004.4(2) pm   γ = 90°. |
| Cell volume | 4.7028(3) nm³ |
| Number of formula units | 8 |
| Density (calculated) | 1.253 mg/m³ |
| Absorption coefficient | 0.160 mm⁻¹ |
| F(000) | 1,864 |
| Size of the crystal | 0.4 × 0.1 × 0.02 mm³ |
| Measurement range of θ | 2.085 to 27.024°. |
| Index ranges | −18 ≤ h ≤ 16, −8 ≤ k ≤ 8, |
| | −61 ≤ l ≤ 62 |
| Measured reflections | 37,852 |
| Independent reflections | 9,494 [R(int) = 0.0725] |
| Completeness up to θ = 25.350° | 99.9% |
| Absorption correction | semi-empirical from equivalents |
| Max. and min. transmission | 1 and 0.93162 |
| Refinement method | full-matrix least-squares on F² |
| Data/restraints/parameters | 9,424/96/696 |
| Goodness-of-fit on F² | 1.030 |
| R values [I > 2σ(I)] | R1 = 0.0632, wR2 = 0.1255 |
| R values (all reflections) | R1 = 0.1183, wR2 = 0.1476 |
| Max. and min. residual electron density | 0.597 and −0.434 e · Å−3 |

Embodiment 10

1-Cyclopentylhydroxymethyl-1,7-dicarba-closo-dodecaborane(12)

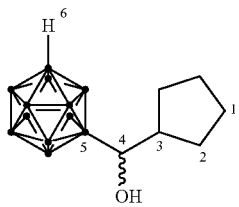

5.0 ml (1.45 M in n-hexane, 7.19 mmol, 1.05 eq.) of an n-butyl lithium solution is slowly dropped into a solution of 1.00 g (6.85 mmol, 1.0 eq.) of 1,7-dicarba-closo-dodecaborane(12) in 50 ml of diethyl ether at 0° C. After 30 minutes, the solution is heated to room temperature. After three hours, the solution is cooled again to 000° C., and 0.62 ml (0.67 mg, 6.85 mmol, 1.0 eq.) of cyclopentaldehyde is dropped in. The solution is then heated to room temperature. After 24 hours, 20 ml of distilled water is added to the white suspension, which is acidulated by means of concentrated hydrochloric acid and then extracted three times by means of 20 ml of diethyl ether on each occasion. The combined organic phases are washed by means of 20 ml of saturated sodium chloride solution and dried by means of magnesium sulfate, and the solvent is then removed under reduced pressure. The residue is purified by column chromatography (eluent: hexane/ethyl acetate 5:1 v/v). A white solid is obtained.

Yield: 0.5 g (2.06 mmol, 30.1%)
$R_f$ value: 0.74 (eluent: hexane/ethyl acetate 5:1 v/v)
Melting point: 50.2-51.3° C.
¹H NMR (CDCl₃): δ=1.25-3.10 (br m, 10H, BH), 1.36 (m, 2H, 2-CH₂a), 1.46 (m, 2H, 1-CH₂a), 1.66 (m, 2H, 2-CH$_{2b}$), 1.78 (m, 2H, 1-CH₂b), 1.94 (br s, 1H, 4-OH), 2.08 (dt, 1H, 3-CH, ³J$_{HH}$=8.2 Hz, ³J$_{HH}$=3.6 Hz), 2.92 (br s, 1H, 6-CH), 3.81 (d, 1H, 4-CH, ³J$_{HH}$=3.6 Hz) ppm.
¹¹B{¹H} NMR (CDCl₃): δ=−16.0 (s, 2B, BH), −13.6 (s, 2B, BH), −11.9 (s, 2B, BH), −11.0 (s, 28, BH), −8.5 (s, 1B, BH), −4.9 (s, 1B, BH) ppm.
¹³C{¹H} NMR (CDCl₃): δ=25.5 (s, 1-CH₂), 26.0 (s, 2-CH₂), 31.8 (s, 2-CH₂), 44.6 (s, 3-CH), 54.5 (s, 6-CH), 75.5 (s, 4-CH), 82.6 (s, 5-C$_q$) ppm.
Mass spectrometry (ESI neg., CH₂Cl₂/CH₃CN):
Calculated: m/z=242.3
Determined: m/z=241.2 (100%, [M−H]⁻), 278.2 (50%, [M+Cl]⁻).
IR spectroscopy (KBr, ṽ in cm⁻¹): 3,591 (m), 3,486 (s), 3,060 (m), 2,955 (s), 2,868 (m), 2,603 (s), 1,450 (w), 1,385 (m), 1,131 (s), 1,009 (m), 817 (w), 732 (m), 707 (w), 669 (w), 608 (w).
Elementary Analysis:
Calculated for $C_8H_{22}B_{10}O_1$: C=39.64% H=9.15%.
Found: C=39.77% H=9.10%.

Embodiment 11

1-Cyclopentylhydroxymethyl-7-thio-1,7-dicarba-closo-dodecaborane(12)

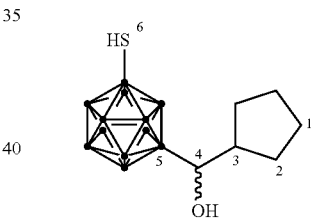

2.54 ml (1.45 M in n-hexane, 3.69 mmol, 2.1 eq.) of an n-butyl lithium solution is slowly dropped into a solution of 425.0 mg (1.76 mmol, 1.0 eq.) of 1-cyclopentylhydroxymethyl-1,7-dicarba-closo-dodecaborane(12) in 50 ml of diethyl ether at 0° C., and after 30 minutes, the solution is heated to room temperature. After three hours, the solution is cooled again to 0° C., to which 56.3 mg (1.76 mmol, 1.0 eq.) of sulfur is added and which is then heated to room temperature. After 24 hours, 50 ml of distilled water is added to the white suspension, which is acidulated by means of concentrated hydrochloric acid and extracted three times by means of 50 ml of diethyl ether on each occasion. The organic phases are combined and washed by means of saturated sodium chloride solution. Drying is carried out by means of magnesium sulfate, the solvent is removed under reduced pressure, and the residue is purified by column chromatography (eluent: hexane/ethyl acetate, 5:1 v/v). A slightly yellowish, highly viscous liquid is obtained.
Yield: 6.34 g (25.8 mmol, 94%)
$R_f$ value: 0.64 (eluent: hexane/ethyl acetate 5:1 v/v)
Melting point: 57.6-58.3° C.
¹H NMR (CDCl₃): δ=1.15-3.20 (br m, 10H, BH), 1.35 (t, 2H, 2-CH₂a, ³J$_{HH}$=8.7 Hz), 1.46 (m, 2H, 1-CH$_{1a}$), 1.65 (m, 2H, 1-CH$_{2b}$), 1.78 (m, 2H, 1-CH$_{1b}$), 2.09 (m, 1H, 3-CH), 3.81 (br d, 1H, 4-CH, $^3J_{HH}$=3.2 Hz) ppm.

$^{11}$B{$^1$H} NMR (CDCl$_3$): δ=−14.8 (s, 2B, BH), −11.5 (s, 1B, BH), −10.6 (s, 2B, BH), −9.2 (s, 2B, BH), −6.6 (s, 2B, BH), −3.8 (s, 1B, BH) ppm.

$^{13}$C{$^1$H} NMR (CDCl$_3$): δ=25.5 (s, 1-CH$_2$), 25.6 (s, 2-CH$_2$), 26.0 (s, 5-C$_q$), 31.9 (s, 6-C$_q$), 44.5 (s, 3-CH), 75.6 (s, 4-CH) ppm.

Mass spectrometry (ESI neg., CH$_2$Cl$_2$/CH$_3$CN):
Calculated: m/z=274.2
Determined: m/z=273.2 (100%, [M−H]$^−$).

IR spectroscopy (KBr, ṽ in cm$^{−1}$): 3,448 (m), 2,952 (s), 2,867 (m), 2,598 (s), 1,451 (w), 1,389 (w), 1,462 (m), 1,093 (m), 1,028 (m), 939 (w), 808 (w), 737 (w).

Elementary Analysis:
Calculated for C$_8$H$_{22}$B$_{10}$O$_1$S$_1$: C=35.01% H=8.08%.
Found: C=44.18% H=8.07%.

Embodiment 12

1-Cyclopentylhydroxymethyl-7-((quinolin-2-ylmethyl)thio)-1,7-dicarba-closo-dodecaborane(12)

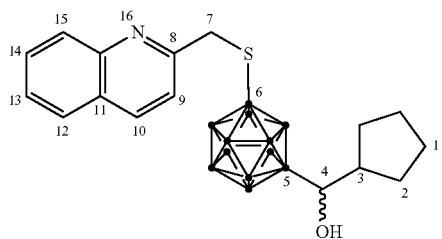

Figure 11:
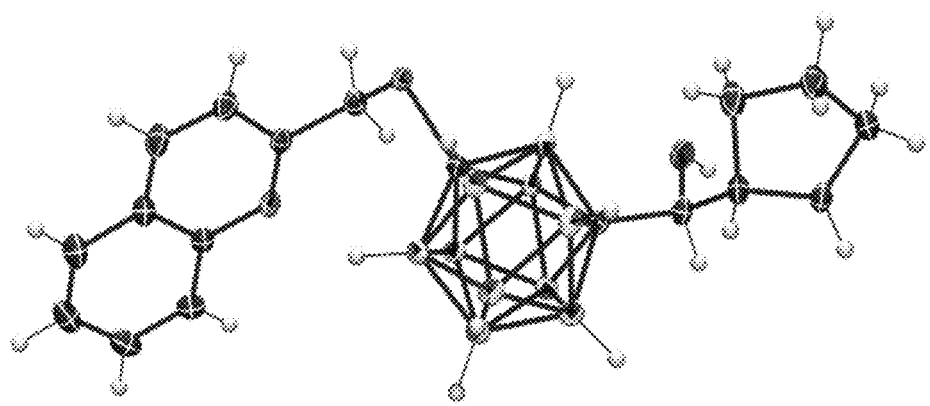
FIG. 11 is a diagram illustrating the 3D chemical structure of 1-Cyclopentylhydroxymethyl-7-((quinolin-2-ylmethyl)thio)-1,7-dicarba-closo-dodecaborane(12).

See FIG. 11 for the 3D chemical structure.

456.0 mg (3.30 mmol, 3.0 eq.) of potassium carbonate is added to a solution of 1-cyclopentylhydroxymethyl-7-thio-1,7-dicarba-closo-dodecaborane(12) (0.3 g, 1.10 mmol, 1.0 eq.) and 2-bromomethyl quinoline (265.0 mg, 1.20 mmol, 1.2 eq.) in 20 ml of acetone at room temperature, and then heated under reflux for 24 hours. After being cooled to room temperature, 20 ml of distilled water and 10 ml of saturated sodium chloride solution are added. Extraction is carried out three times by means of 20 ml of diethyl ether on each occasion, the organic phases are combined, and dried by means of magnesium sulfate, and the solvent is removed under reduced pressure. The raw product is purified by column chromatography (eluent: n-hexane/ethyl acetate 5:1 v/v). The product is obtained as a white solid and is crystallised from methanol.

Yield: 260 mg (0.63 mmol, 56.8%)
R$_f$ value: 0.30 (eluent: hexane/ethyl acetate 5:1 v/v)
Melting point: 108-109° C.

$^1$H NMR (CDCl$_3$): δ=1.15-2.95 (br m, 10H, BH), 1.23 (m, 2H, 2-CH$_2$a), 1.35 (m, 2H, 1-CH$_2$a), 1.51 (m, 2H, 1-CH$_{2b}$), 1.67 (br m, 2H, 2-CH$_{2b}$), 1.96 (m, 1H, 3-CH), 3.72 (br m, 1H, 4-CH), 4.23 (s, 2H, 7-CH$_2$), 7.41 (d, 1H, 9-CH, $^3J_{HH}$=8.7 Hz), 7.45 (t, 1H, 13-CH, $^3J_{HH}$=8.0 Hz), 7.63 (t, 1H, 14-CH, $^3J_{HH}$=7.9 Hz), 7.71 (d, 1H, 12-CH, $^3J_{HH}$=8.0 Hz), 7.98 (d, 1H, 15-CH, $^3J_{HH}$=7.9 Hz), 8.04 (d, 1H, 10-CH, $^3J_{HH}$=8.7 Hz) ppm.

$^{11}$B{$^1$H} NMR (CDCl$_3$): δ=−13.4 (s, 3B, BH), −11.9 (s, 2B, BH), −11.0 (s, 3B, BH), −7.3 (s, 1B, BH), −5.2 (s, 1B, BH) ppm.

$^{13}$C{$^1$H} NMR (CDCl$_3$): δ=25.5 (s, 1-CH$_2$), 31.8 (s, 2-CH$_2$), 43.1 (s, 7-CH$_2$), 44.5 (s, 3-CH), 71.3 (s, 6-C$_q$), 75.5 (s, 4-CH), 83.0 (s, 5-C$_q$), 120.7 (s, 9-CH), 126.6 (s, 13-CH), 127.0 (s, 11-C$_q$), 127.5 (s, 12-CH), 129.0 (s, 15-CH), 129.8 (s, 14-CH), 136.9 (s, 10-CH), 147.6 (s, 16-CH), 155.5 (s, 8-C$_q$) ppm.

Mass spectrometry (ESI pos., CH$_2$Cl$_2$/CH$_3$OH):
Calculated: m/z=415.3
Determined: m/z=416.3 (40%, [M+H]*), 438.3 (100%, [M+Na]$^+$).

IR spectroscopy (KBr, ṽ in cm$^{−1}$): 3,181 (m), 2,955 (w), 2,593 (s), 2,582 (s), 2,570 (s), 1,602 (w), 1,507 (m), 821 (m), 761 (m).

Elementary Analysis:
Calculated for C$_{18}$H$_{29}$B$_{10}$N$_1$O$_1$S$_1$: C=52.02% H=7.03% N=3.37%.
Found: C=52.38% H=6.86% N=3.04%.

X-Ray Crystal Structure Analysis

| | |
|---|---|
| Empirical formula | C$_{18}$H$_{29}$B$_{10}$N$_1$O$_1$S$_1$ |
| Formula weight | 415.58 |
| Temperature | 130(2) K |
| Wavelength | 71.073 pm |
| Crystal system | monoclinic |
| Space group | P 2$_1$/n |
| Lattice constant | a = 1,310.67(2) pm  α = 90°. |
| | b = 1,086.26(2) pm  β = 100.665(2)°. |
| | c = 1,569.12(3) pm  γ = 90°. |
| Cell volume | 2.19541(7) nm$^3$ |
| Number of formula units | 4 |
| Density (calculated) | 1.257 mg/m$^3$ |
| Absorption coefficient | 0.159 mm$^{−1}$ |
| F(000) | 872 |
| Size of the crystal | 0.4 × 0.35 × 0.3 mm$^3$ |
| Measurement range of θ | 2.240 to 32.554°. |
| Index ranges | −19 ≤ h ≤ 18, −16 ≤ k ≤ 15, −23 ≤ l ≤ 23 |
| Measured reflections | 28,941 |
| Independent reflections | 7,380 [R(int) = 0.0440] |
| Completeness up to θ = 30.510° | 100.0% |
| Absorption correction | semi-empirical from equivalents |
| Max. and min. transmission | 1 and 0.97922 |
| Refinement method | full-matrix least-squares on F$^2$ |
| Data/restraints/parameters | 7,380/29/381 |
| Goodness-of-fit on F$^2$ | 1.012 |
| R values [I > 2σ(I)] | R1 = 0.0446, wR2 = 0.0984 |
| R values (all reflections) | R1 = 0.0681, wR2 = 0.1082 |
| Max. and min. residual electron density | 0.370 and −0.327 e · Å−3 |

Embodiment 13

1-Cyclopentylhydroxymethyl-7-hydroxy-1,7-dicarba-closo-dodecaborane(12)

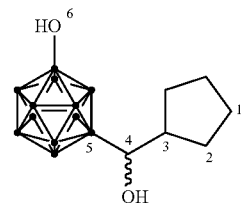

3.45 ml (1.45 M in n-hexane, 4.97 mmol, 2.3 eq.) of an n-butyl lithium solution is carefully dropped into a solution of 350.0 mg (2.16 mmol, 1.0 eq.) of 1-hydroxy-1,7-dicarba-closo-dodecaborane(12) in 100 ml of diethyl ether at 000° C.

in inert conditions. After 30 minutes, the solution is heated to room temperature. After three hours, the solution is cooled again to 0° C., and 0.2 ml (212.0 mg, 2.16 mmol, 1.0 eq.) of cyclopentaldehyde is dropped in. The solution is then heated to room temperature. After 24 hours, 20 ml of distilled water is added to the white suspension, which is acidulated by means of concentrated hydrochloric acid and extracted three times by means of 20 ml of diethyl ether on each occasion. The combined organic phases are washed by means of 20 ml of saturated sodium chloride solution and dried by means of magnesium sulfate, and the solvent is then removed under reduced pressure. The residue is purified by column chromatography (eluent: hexane/ethyl acetate 5:1 v/v). A colourless liquid which solidifies when at rest for long periods is obtained.

Yield: 283.0 mg (1.09 mmol, 50.7%)
$R_f$ value: 0.43 (eluent: hexane/ethyl acetate 5:1 v/v)
Melting point: 71.9-72.8° C.
$^1$H NMR (CDCl$_3$): b=1.05-3.39 (br m, 10H, BH), 1.35 (m, 2H, 2-CH$_2$a), 1.46 (m, 2H, 1-CH$_2$a), 1.70 (m, 2H, 2-CH$_2$b), 1.79 (m, 2H, 1-CH$_2$b), 2.09 (m, 1H, 3-CH), 3.80 (d, 1H, 4-CH, $^3J_{HH}$=3.6 Hz) ppm.
$^{11}$B{$^1$H} NMR (CDCl$_3$): δ=−14.4 (s, 4B, BH), −13.6 (s, 3B, BH), −11.5 (s, 2B, BH), −6.2 (s, 1B, BH) ppm.
$^{13}$C{$^1$H} NMR (CDCl$_3$): δ=25.6 (s, 1-CH$_2$), 31.9 (s, 2-CH$_2$), 44.6 (s, 3-CH), 74.1 (s, 5-C$_q$), 75.5 (s, 4-CH) ppm.
Mass spectrometry (ESI neg., CH$_2$Cl$_2$/CH$_3$CN):
Calculated: m/z=258.3
Determined: m/z=257.3 (100%, [M−H]$^-$).
IR spectroscopy (KBr, ṽ in cm$^{-1}$): 3,454 (w), 3,230 (m), 2,956 (w), 2,866 (w), 2,611 (s), 2,600 (s), 2,591 (s), 1,202 (m), 1,020 (m).
Elementary Analysis:
Calculated for C$_8$H$_{22}$B$_{10}$O$_2$: C=37.19% H=8.58%.
Found: C=40.16% H=8.52%.

Embodiment 14

1-Cyclopentylhydroxymethyl-7-(quinolin-2-yl-methoxy)-1,7-dicarba-closo-dodecaborane(12)

159.2 mg (1.15 mmol, 3.0 eq.) of potassium carbonate is added to a solution of 1-cyclopentylhydroxymethyl-7-hydroxy-1,7-dicarba-closo-dodecaborane(12) (100.0 g, 0.38 mmol, 1.0 eq.) and 2-bromomethyl quinoline (85.0 mg, 0.38 mmol, 1.0 eq.) in 50 ml of acetone at room temperature, and then heated under reflux for 24 hours. After being cooled to room temperature, the suspension is filtered, and remaining potassium carbonate is extracted three times by means of 20 ml of diethyl ether on each occasion. The organic phases are combined, and dried by means of magnesium sulfate, and the solvent is removed under reduced pressure. The raw product is purified by column chromatography (eluent: n-hexane/ethyl acetate 5:1 v/v). The product is obtained as a white solid and is crystallised from ethyl acetate.

Yield: 166 mg (0.40 mmol, 51%)
$R_f$ value: 0.25 (eluent: hexane/ethyl acetate 10:1 v/v)
Melting point: 108-109° C.
$^1$H NMR (CDCl$_3$): 5=1.19-3.63 (br m, 10H, BH), 1.39 (m, 2H, 2-CH$_2$a), 1.48 (m, 2H, 1-CH$_2$a), 1.68 (m, 2H, 2-CH$_{2b}$), 1.81 (m, 2H, 1-CH$_{2b}$), 2.11 (dt, 1H, 3-CH, $^3J_{HH}$=8.4 Hz, $^3J_{HH}$=3.5 Hz), 3.83 (br q, 1H, 4-CH, $^3J_{HH}$=3.6 Hz), 4.86 (s, 2H, 7-CH$_2$), 7.47 (d, 1H, 9-CH, $^3J_{HH}$=8.5 Hz), 7.55 (t, 1H, 13-CH, $^3J_{HH}$=8.2 Hz), 7.73 (t, 1H, 14-CH, $^3J_{HH}$=8.5 Hz), 7.82 (d, 1H, 12-CH, $^3J_{HH}$=8.2 Hz), 8.05 (d, 1H, 15-CH, $^3J_{HH}$=8.5 Hz), 8.19 (d, 1H, 10-CH, $^3J_{HH}$=8.5 Hz) ppm.
$^{11}$B{$^1$H} NMR (CDCl$_3$): δ=−14.7 (s, 5B, BH), −13.8 (s, 2B, BH), −12.8 (s, 2B, BH), −7.6 (s, 1B, BH) ppm.
$^{13}$C{$^1$H} NMR (CDCl$_3$): 5=25.5 (s, 1-CH$_2$), 31.9 (s, 2-CH$_2$), 44.6 (s, 3-CH), 75.4 (s, 4-CH), 78.2 (s, 5-C$_q$), 106.4 (s, 6-C$_q$), 119.0 (s, 9-CH), 126.6 (s, 13-CH), 127.5 (s, 11-C$_q$), 127.6 (s, 12-CH), 128.9 (s, 15-CH), 129.8 (s, 14-CH), 136.9 (s, 10-CH), 147.2 (s, 16-C$_q$), 156.1 (s, 8-C$_q$) ppm.
Mass spectrometry (ESI pos., CH$_2$Cl$_2$/CH$_3$CN):
Calculated: m/z=399.3
Determined: m/z=400.3 (100%, [M+H]$^+$), 422.3 (10%, [M+Na]$^+$).
IR spectroscopy (KBr, Q in cm$^{-1}$): 3,434 (s), 2,963 (m), 2,600 (w), 1,631 (w), 1,262 (s), 1,096 (s), 1,022 (s), 865 (w), 802 (s), 704 (w).
Elementary Analysis:
Calculated for C$_{18}$H$_{29}$B$_{10}$NOS: C=52.02% H=7.03% N=3.37%.
Found: C=51.60% H=7.25% N=3.13%.

Embodiment 15

1-Cyclopentylhydroxymethyl-12-thio-1,12-dicarba-closo-dodecaborane(12)

1.43 ml (1.45 M in n-hexane, 2.07 mmol, 2.1 eq.) of an n-butyl lithium solution is carefully dropped into a solution of 176.0 mg (0.99 mmol, 1.0 eq.) of 1-mercapto-1,12-dicarba-closo-dodecaborane(12) in 50 ml of diethyl ether at 0° C. in inert conditions. After 30 minutes, the solution is heated to room temperature. After three hours, the solution is cooled again to 0° C., and 84 µl (91.0 mg, 0.93 mmol, 1.0 eq.) of cyclopentaldehyde is dropped in. The solution is then heated to room temperature. After 24 hours, 20 ml of distilled water is added to the white suspension, which is acidulated by means of concentrated hydrochloric acid and then extracted three times by means of 20 ml of diethyl ether on each occasion. The combined organic phases are washed by means of 20 ml of saturated sodium chloride solution and dried by means of magnesium sulfate, and the solvent is then removed under reduced pressure. The residue is purified by column chromatography (eluent: hexane/ethyl acetate 5:1 v/v). A slightly yellowish solid is obtained.

Yield: 247.2 mg (0.90 mmol, 91%)

$R_f$ value: 0.64 (eluent: hexane/ethyl acetate 5:1 v/v)

Melting point: 57.6-58.3° C.

$^1$H NMR (CDCl$_3$): δ=1.18-3.20 (br m, 10H, BH), 1.23 (m, 2H, 2-CH$_2$a), 1.31 (m, 2H, 1-CH$_2$a), 1.55 (m, 2H, 2-CH$_{2b}$), 1.68 (m, 2H, 1-CH$_{2b}$), 1.83 (m, 1H, 3-CH), 3.44 (d, 1H, 4-CH, $^3J_{HH}$=3.4 Hz) ppm.

$^{11}$B{$^1$H} NMR (CDCl$_3$): δ=−14.7 (s, 2B, BH), −13.8 (s, 1B, BH), −13.2 (s, 3B, BH), −11.1 (s, 4B, BH) ppm.

$^{13}$C{$^1$H} NMR (CDCl$_3$): δ=25.6 (s, 1-CH$_2$), 31.8 (s, 2-CH$_2$), 44.1 (s, 3-CH), 75.5 (s, 4-CH), 72.6 (s, 6-C$_q$), 82.7 (s, 5-C$_q$) ppm.

Mass spectrometry (ESI neg., CH$_2$Cl$_2$/CH$_3$CN):

Calculated: m/z=274.2

Determined: m/z=273.2 (20%, [M−H]$^−$).

IR spectroscopy (KBr, ṽ in cm$^{-1}$): 3,387 (s), 2,957 (s), 2,928 (s), 2,859 (m), 2,602 (s), 1,461 (w), 1,253 (w), 1,137 (s), 842 (m), 732 (w).

Elementary Analysis:

Calculated for C$_8$H$_{22}$B$_{10}$O$_S$: C=35.01% H=8.08%.

Found: C=40.10% H=9.74%.

Embodiment 16

1-Cyclopentylhydroxymethyl-12-(quinolin-2-ylm-ethyl)thio-1,12-dicarba-closo-dodecaborane(12)

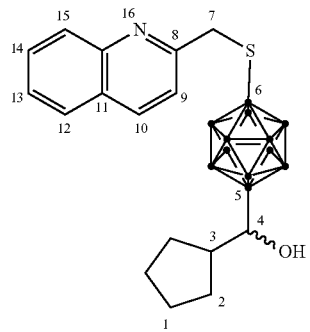

Figure 12:
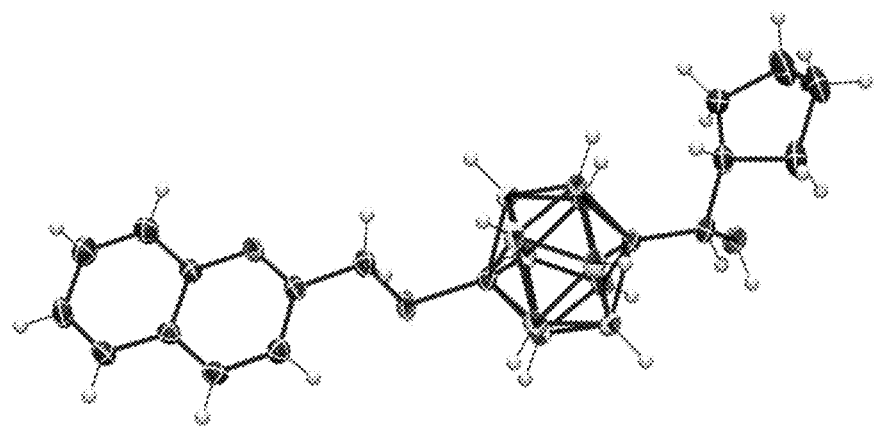
FIG. 12 is a diagram illustrating the 3D chemical structure of 1-Cyclopentylhydroxymethyl-12-(quinolin-2-ylmethyl)thio-1,12-dicarba-closo-dodecaborane(12).

See FIG. 12 for the 3D chemical structure.

410.0 mg (2.97 mmol, 3.0 eq.) of potassium carbonate is added to a solution of 1-cyclopentylhydroxymethyl-12-thio-1,12-dicarba-closo-dodecaborane(12) (273.0 g, 0.99 mmol, 1.0 eq.) and 2-bromomethyl quinoline (242.0 mg, 1.09 mmol, 1.1 eq.) in 50 ml of acetone at room temperature, and then heated under reflux for 24 hours. After being cooled to room temperature, the suspension is filtered, and remaining potassium carbonate is extracted three times by means of 20 ml of diethyl ether on each occasion. The organic phases are combined, and dried by means of magnesium sulfate, and the solvent is removed under reduced pressure. The raw product is purified by column chromatography (eluent: n-hexane/ethyl acetate 5:1 v/v). The product is obtained as a white solid and is crystallised from ethyl acetate.

Yield: 130.0 mg (0.31 mmol, 31.6%)

$R_f$ value: 0.40 (eluent: hexane/ethyl acetate 5:1 v/v)

Melting point: 135.0-136.0° C.

$^1$H NMR (CDCl$_3$): δ=1.12-3.30 (br m, 10H, BH), 1.23 (m, 2H, 2-CH$_{2a}$), 1.35 (m, 2H, 1-CH$_2$a), 1.47 (m, 2H, 2-CH$_{2b}$), 1.54 (m, 2H, 1-CH$_{2b}$), 1.69 (d, 1H, 3-CH, $^3J_{HH}$=7.0 Hz), 3.47 (q, 1H, 4-CH, $^3J_{HH}$=3.4 Hz), 4.14 (s, 2H, 7-CH$_2$), 7.39 (d, 1H, 9-CH, $^3J_{HH}$=8.4 Hz), 7.52 (t, 1H, 13-CH, $^3J_{HH}$=7.4 Hz), 7.69 (t, 1H, 14-CH, $^3J_{HH}$=7.4 Hz), 7.76 (d, 1H, 12-CH, $^3J_{HH}$=8.1 Hz), 8.01 (d, 1H, 15-CH, $^3J_{HH}$=8.3 Hz), 8.08 (d, 1H, 10-CH, $^3J_{HH}$=8.4 Hz) ppm.

$^{11}$B{$^1$H} NMR (CDCl$_3$): δ=−13.4 (s, 5B, BH), −12.3 (s, 5B, BH) ppm.

$^{13}$C{$^1$H} NMR (CDCl$_3$): δ=26.0 (s, 1-CH$_2$), 31.8 (s, 2-CH$_2$), 42.9 (s, 7-CH$_2$), 44.1 (s, 3-CH), 75.6 (s, 4-CH), 78.2 (s, 6-C$_q$), 85.5 (s, 5-C$_q$), 120.7 (s, 9-CH), 126.5 (s, 13-CH), 127.0 (s, 11-C$_q$), 127.4 (s, 12-CH), 129.0 (s, 15-CH), 129.7 (s, 14-CH), 136.8 (s, 10-CH), 147.6 (s, 16-C$_q$), 155.6 (s, 8-C$_q$) ppm.

Mass spectrometry (ESI pos., CH$_2$Cl$_2$/CH$_3$CN):

Calculated: m/z=415.3

Determined: m/z=438.3 (100%, [M+Na]$^+$).

IR spectroscopy (KBr, G in cm$^{-1}$): 3,241 (m), 2,938 (m), 2,856 (w), 2,593 (s), 2,362 (w), 1,597 (w), 1,507 (m), 1,428 (m), 1,133 (m), 1,099 (m), 832 (m), 761 (m), 624 (w).

Elementary Analysis:

Calculated for C$_{18}$H$_{29}$B$_{10}$N$_1$O$_1$S$_1$: C=52.02% H=7.03% N=3.37%.

Found: C=51.25% H=6.82% N=3.04%.

X-Ray Crystal Structure Analysis:

| | |
|---|---|
| Empirical formula | C$_{18}$H$_{29}$B$_{10}$N$_1$O$_1$S$_1$ |
| Formula weight | 415.58 |
| Temperature | 130(2) K |
| Wavelength | 71.073 pm |
| Crystal system | monoclinic |
| Space group | P 21/c |
| Lattice constant | a = 1,015.91(3) pm    α = 90°. |
| | b = 1,519.89(4) pm    β = 90.400(2)°. |
| | c = 1,456.58(4) pm    γ = 90°. |
| Cell volume | 2.24901(11) nm$^3$ |
| Number of formula units | 4 |
| Density (calculated) | 1.227 mg/m$^3$ |
| Absorption coefficient | 0.156 mm$^{-1}$ |
| F(000) | 872 |
| Size of the crystal | 0.3 × 0.2 × 0.1 mm$^3$ |
| Measurement range of θ | 1.937 to 30.608°. |
| Index ranges | −13 ≤ h ≤ 13, −21 ≤ k ≤ 21, |
| | −12 ≤ l ≤ 20 |
| Measured reflections | 20,798 |
| Independent reflections | 6,289 [R(int) = 0.0515] |
| Completeness up to θ = 28.285° | 100.0% |
| Absorption correction | semi-empirical from equivalents |
| Max. and min. transmission | 1 and 0.99096 |
| Refinement method | full-matrix least-squares on F$^2$ |
| Data/restraints/parameters | 6,289/51/388 |
| Goodness-of-fit on F$^2$ | 1.032 |
| R values [I > 2σ(I)] | R1 = 0.0545, wR2 = 0.1155 |
| R values (all reflections) | R1 = 0.1041, wR2 = 0.1351 |
| Max. and min. residual electron density | 0.347 and −0.269 e · Å−3 |

Embodiment 17

1-Cyclopentylhydroxymethyl-12-hydroxy-1,12-dicarba-closo-dodecaborane(12)

1.40 ml (1.45 M in n-hexane, 2.03 mmol, 2.2 eq.) of an n-butyl lithium solution is carefully dropped into a solution of 150.0 mg (0.93 mmol, 1.0 eq.) of 1-hydroxy-1,12-dicarba-closo-dodecaborane(12) in 50 ml of diethyl ether at 0° C. in inert conditions. After 30 minutes, the solution is heated to room temperature. After three hours, the solution is cooled again to 0° C., and 84 µl (91.0 mg, 0.93 mmol, 1.0 eq.) of cyclopentaldehyde is dropped in. The solution is then heated to room temperature. After 24 hours, 20 ml of distilled water is added to the white suspension, which is acidulated by means of concentrated hydrochloric acid and then extracted three times by means of 20 ml of diethyl ether on each occasion. The combined organic phases are washed by means of 20 ml of saturated sodium chloride solution and dried by means of magnesium sulfate, and the solvent is then removed under reduced pressure. The residue is purified by column chromatography (eluent: hexane/ethyl acetate 5:1 v/v). A white solid is obtained.

Yield: 127.0 mg (0.49 mmol, 53%)

$R_f$ value: 0.49 (eluent: hexane/ethyl acetate 5:1 v/v)

Melting point: 57.6-58.3° C.

$^1$H NMR (CDCl$_3$): δ=1.13-3.39 (br m, 10H, BH), 1.26 (m, 2H, 2-CH$_2$a), 1.36 (m, 2H, 1-CH$_2$a), 1.56 (m, 2H, 2-CH$_{2b}$), 1.68 (m, 2H, 1-CH$_{2b}$), 1.86 (m, 2H, 3-CH), 3.56 (br s, 1H, 4-CH) ppm.

$^{11}$B{$^1$H} NMR (CDCl$_3$): δ=−15.5 (s, 5B, BH), −13.2 (s, 5B, BH) ppm.

$^{13}$C{$^1$H} NMR (CDCl$_3$): δ=25.6 (s, 1-CH$_2$), 31.9 (s, 2-CH$_2$), 44.5 (s, 3-CH), 74.9 (s, 4-CH), 74.9 (s, 5-C$_q$), 74.9 (s, 6-C$_q$) ppm.

Mass spectrometry (ESI neg., CH$_2$Cl$_2$/CH$_3$OH):

Calculated: m/z=258.3

Determined: m/z=257.3 (100%, [M−H]$^-$).

IR spectroscopy (KBr, G in cm$^{-1}$): 3,485 (w), 3,255 (m), 2,955 (m), 2,860 (w), 2,607 (s), 1,392 (w), 1,206 (m), 1,145 (w), 1,016 (m), 999 (w), 978 (w), 758 (w), 729 (w).

Elementary Analysis:

Calculated for C$_8$H$_{22}$B$_{10}$O$_2$: C=37.19% H=8.58%.

Found: C=32.89% H=8.19%.

Embodiment 18

1-Cyclopentylhydroxymethyl-12-(quinolin-2-yl-methoxy)-1,12-dicarba-closo-dodecaborane(12)

Figure 13:
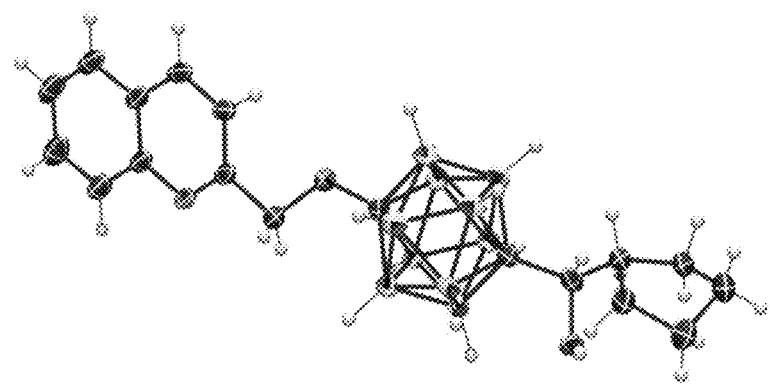
FIG. 13 is a diagram illustrating the 3D chemical structure of 1-Cyclopentylhydroxymethyl-12-(quinolin-2-ylmethoxy)-1,12-dicarba-closo-dodecaborane(12).

See FIG. 13 for the 3D chemical structure.

159.2 mg (1.15 mmol, 3.0 eq.) of potassium carbonate is added to a solution of 1-cyclopentylhydroxymethyl-12-hydroxy-1,12-dicarba-closo-dodecaborane(12) (100.0 mg, 0.38 mmol, 1.0 eq.) and 2-bromomethyl quinoline (85.0 mg, 0.38 mmol, 1.0 eq.) in 50 ml of acetone at room temperature, and then heated under reflux for 24 hours. After being cooled to room temperature, the suspension is filtered, and remaining potassium carbonate is extracted three times by means of 20 ml of diethyl ether on each occasion. The organic phases are combined, and dried by means of magnesium sulfate, and the solvent is removed under reduced pressure. The raw product is purified by column chromatography (eluent: n-hexane/ethyl acetate 5:1 v/v). The product is obtained as a white solid and is crystallised from ethyl acetate.

Yield: 52.0 mg (13.0 mmol, 33.9%)

$R_f$ value: 0.24 (eluent: hexane/ethyl acetate 10:1 v/v)

Melting point: 154.0-154.9° C.

$^1$H NMR (CDCl$_3$): δ=1.16-3.40 (br m, 10H, BH), 1.27 (m, 2H, 2-CH$_2$a), 1.39 (m, 2H, 1-CH$_2$a), 1.58 (m, 2H, 1-CH$_{2b}$), 1.70 (m, 2H, 2-CH$_{2b}$), 1.89 (m, 1H, 3-CH), 3.61 (q, 1H, 4-CH, $^3J_{HH}$=3.4 Hz), 4.66 (s, 2H, 7-CH$_2$), 7.37 (d, 1H, 9-CH, $^3J_{HH}$=8.4 Hz), 7.53 (t, 1H, 13-CH, $^3J_{HH}$=8.0 Hz), 7.71 (t, 1H, 14-CH, $^3J_{HH}$=8.5 Hz), 7.79 (d, 1H, 12-CH, $^3J_{HH}$=8.0 Hz), 8.00 (d, 1H, 15-CH, $^3J_{HH}$=8.5 Hz), 8.13 (d, 1H, 10-CH, $^3J_{HH}$=8.4 Hz) ppm.

$^{11}$B{$^1$H} NMR (CDCl$_3$): δ=−15.7 (s, 5B, BH), −14.0 (s, 5B, BH) ppm.

$^{13}$C{$^1$H} NMR (CDCl$_3$): δ=25.6 (s, 1-CH$_2$), 31.9 (s, 2-CH$_2$), 44.5 (s, 3-CH$_2$), 75.1 (s, 4-CH), 75.4 (s, 5-C$_q$), 76.0 (s, 7-CH$_2$), 112.1 (s, 6-C$_q$), 119.0 (s, 9-CH), 126.7 (s, 13-CH), 127.6 (s, 11-C$_q$), 127.7 (s, 12-CH), 129.0 (s, 15-CH), 129.9 (s, 14-CH), 137.0 (s, 10-CH), 147.3 (s, 16-C$_q$), 155.9 (s, 8-C$_q$) ppm.

Mass spectrometry (ESI pos., CH$_2$Cl$_2$/CH$_3$OH):

Calculated: m/z=399.3

Determined: m/z=400.3 (100%, [M+H]$^+$), 422.3 (40%, [M+Na]$^+$).

IR spectroscopy (KBr, Q in cm$^{-1}$): 3,215 (m), 2,945 (w), 2,611 (s), 2,361 (w), 1,508 (w), 1,207 (m), 1,138 (w), 1,089 (m), 1,055 (m), 825 (m), 754 (w).

Elementary Analysis:

Calculated for C$_{ia}$H$_{29}$B$_{10}$N$_1$O$_2$: C=54.11% H=7.32% N=3.51%.

Found: C=54.18% H=7.27% N=3.00%.

X-Ray Crystal Structure Analysis:

| | |
|---|---|
| Empirical formula | $C_{18}H_{29}B_{10}N_1O_2$ |
| Formula weight | 399.52 |
| Temperature | 130(2) K |
| Wavelength | 71.073 pm |
| Crystal system | monoclinic |
| Space group | P 21/n |
| Lattice constant | a = 723.56(2) pm  α = 90°. |
| | b = 1,133.24(3) pm  β = 90.135(2)°. |
| | c = 2,672.53(7) pm  γ = 90°. |
| Cell volume | 2.19138(10) nm³ |
| Number of formula units | 4 |
| Density (calculated) | 1.211 mg/m³ |
| Absorption coefficient | 0.069 mm$^{-1}$ |
| F(000) | 840 |
| Size of the crystal | 0.2 × 0.15 × 0.15 mm³ |
| Measurement range of θ | 1.952 to 30.587°. |
| Index ranges | −10 ≤ h ≤ 10, −15 ≤ k ≤ 15, −35 ≤ l ≤ 36 |
| Measured reflections | 24,067 |
| Independent reflections | 6,101 [R(int) = 0.0524] |
| Completeness up to θ = 28.285° | 100.0% |
| Absorption correction | semi-empirical from equivalents |
| Max. and min. transmission | 1 and 0.98423 |
| Refinement method | full-matrix least-squares on F² |
| Data/restraints/parameters | 6,101/16/381 |
| Goodness-of-fit on F² | 1.017 |
| R values [I > 2σ(I)] | R1 = 0.0585, wR2 = 0.1260 |
| R values (all reflections) | R1 = 0.0984, wR2 = 0.1434 |
| Max. and min. residual electron density | 0.312 and −0.322 e · Å−3 |

Embodiment 19

1-(Tetrahydro-2H-pyran-4-olyl)-7-((3-mercaptomethyl-1-(4-methansulfonylphenyl)-5-phenyl-1H-pyrazolyl)-1,7-dicarba-closo-dodecaborane(12)

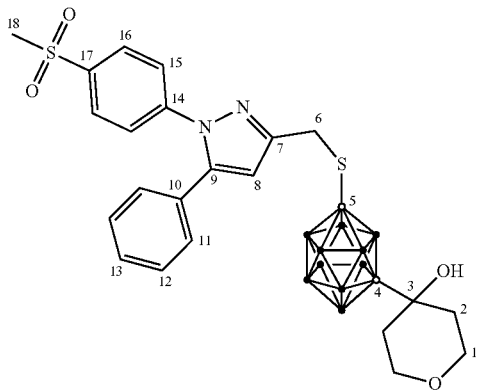

50.0 mg (0.36 mmol, 1.0 eq.) of potassium carbonate is added to a solution of 1-mercapto-7-(tetrahydro-2H-pyran-4-olyl)-1,7-dicarba-closo-dodecaborane(12) (100.0 mg, 0.36 mmol, 1.0 eq.) and 3-bromomethyl-1-(4-methanesulfonylphenyl)-5-phenyl-1H-pyrazole (140.7 mg, 0.36 mmol, 1.0 eq.) in 50 ml of acetone at room temperature, and then heated under reflux for 24 hours. After being cooled to room temperature, 20 ml of distilled water and 10 ml of saturated sodium chloride solution are added. Extraction is carried out three times by means of 20 ml of diethyl ether on each occasion, the organic phases are combined, and dried by means of magnesium sulfate, and the solvent is removed under reduced pressure. The raw product is purified by column chromatography (eluent: n-hexane/ethyl acetate 1:1 v/v). The product is obtained as a colourless solid.

Yield: 84.0 mg (0.14 mmol, 40%)

$R_f$ value: 0.27 (eluent: n-hexane/ethyl acetate 1:1 v/v)

Melting point: 88.0-89.0° C.

$^1$H NMR (CDCl$_3$): δ=1.12-3.79 (br m, 10H, BH), 1.53 (d, 2H, seat-2-CH$_2$, $^3J_{HH}$=13.3 Hz), 1.65 (br s, 1H, 3-OH), 1.81 (dt, 2H, boat-2-CH$_2$, $^3J_{HH}$=13.3 Hz), 3.05 (s, 3H, 18-CH$_3$), 3.65 (dt, 2H, seat-1-CH$_2$, $^3J_{HH}$=11.2 Hz), 3.79 (dd, 2H, boat-1-CH$_2$, $^3J_{HH}$=11.2 Hz), 4.08 (s, 2H, 6-CH$_2$), 6.49 (s, 1H, 8-CH), 7.21 (d, 2H, 11-CH, $^3J_{HH}$=8.4 Hz), 7.38 (m, 3H, 12,13-CH), 7.46 (d, 2H, 15-CH, $^3J_{HH}$=8.9 Hz), 7.88 (d, 2H, 16-CH, $^3J_{HH}$=8.9 Hz) ppm.

$^{11}$B{$^1$H} NMR (CDCl$_3$): δ=−13.5 (s, 2B, BH), −12.5 (s, 2B, BH), −10.8 (s, 3B, BH), −7.8 (s, 1B, BH), −4.4 (s, 2B, BH) ppm.

$^{13}$C{$^1$H} NMR (CDCl$_3$): δ=33.4 (s, 6-CH$_2$), 39.4 (s, 2-CH$_2$), 44.5 (s, 18-CH$_3$), 63.8 (s, 1-CH$_2$), 69.5 (s, 4-C$_q$), 70.8 (s, 5-C$_q$), 88.2 (s, 3-C$_q$), 109.0 (s, 8-CH), 125.0 (s, 15-CH), 128.4 (s, 16-CH), 128.7 (s, 11-CH), 128.9 (s, 12-CH), 129.2 (s, 13-CH), 129.6 (s, 10-C$_q$), 138.8 (s, 17-C$_q$), 143.9 (s, 14-C$_q$), 144.8 (s, 9-C$_q$), 148.6 (s, 7-C$_q$) ppm.

Mass spectrometry (ESI pos., CH$_2$Cl$_2$/CH$_3$CN):

Calculated: m/z=586.3

Determined: m/z=588.3 (100%, [M+H]*), 587.3 (95%, [M+H]*).

IR spectroscopy (KBr, ṽ in cm$^{-1}$): 3,473 (s), 2,960 (s), 2,928 (s), 2,869 (s), 2,602 (s), 1,595 (s), 1,548 (w), 1,504 (s), 1,454 (w), 1,436 (w), 1,406 (m), 1,372 (s), 1,317 (s), 1,300 (s), 1,242 (m), 1,156 (w), 1,152 (s), 1,091 (s) 1,091 (m), 1,016 (m), 956 (m), 876 (w), 844 (m), 807 (w), 782 (s), 762 (m), 697 (m), 587 (m), 556 (m), 547 (m), 533 (m), 490 (w), 446 (w).

Elementary Analysis:

Calculated for $C_{24}H_{34}B_{10}N_2O_4S_2$: C=49.13% H=5.84% N=4.77%.

Found: C=49.56% H=5.93% N=4.42%.

Embodiment 20

9-Iodo-1-mercapto-7-(tetrahydro-2H-pyran-4-olyl)-1,7-dicarba-closo-dodecaborane(12)

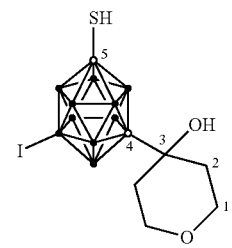

1.5 g (5.50 mmol, 1.0 eq.) of 9-iodo-1,7-dicarba-closo-dodecaborane(12) is dissolved in 300 ml of diethyl ether and carefully dropped into 4.17 ml (1.45 M in n-hexane, 6.04 mmol, 1.1 eq.) of an n-butyl lithium solution at 0° C. The clear yellowish solution is then heated to room temperature. After three hours, said solution is cooled again to 0° C., and 176.0 mg (5.50 mmol, 1.0 eq.) of sulfur is added. The solution is heated to room temperature, to which, after 24 hours, 4.17 ml (1.45 M in n-hexane, 6.04 mmol, 1.1 eq.) of n-butyl lithium is added at 0° C. and which is then heated to room temperature. After three hours, the solution is cooled to 0° C., to which 0.51 ml (550.7 mg, 5.50 mmol, 1.0 eq.) of tetrahydro-2H-pyranone is added. Said solution is then heated to room temperature. After 24 hours, 30 ml of distilled water is added to the obtained white suspension, which is acidulated by means concentrated hydrochloric acid and extracted three times by means of 20 ml of diethyl ether on each occasion. The combined organic phases are neutralised by means of distilled water, washed by means of saturated sodium chloride solution, and dried by means of magnesium sulfate, and the solvent is removed under reduced pressure. The residue is recrystallised from n-hexane, and the product is obtained as a bright yellow solid.

Yield: 2.12 g (5.3 mmol, 96%)

$R_f$ value: 0.08 (eluent: n-hexane/ethyl acetate 5:2 v/v)

$^1$H NMR (acetone-$d_6$): δ=1.10-4.02 (br m, 9H, BH), 1.52 (d, 2H, seat-2-CH$_2$, $^3J_{HH}$=12.6 Hz), 1.58 (dt, 2H, boat-2-CH$_2$, $^3J_{HH}$=12.6 Hz), 3.48 (dt, 2H, seat-1-CH$_2$, $^3J_{HH}$=11.4 Hz), 3.58 (dd, 2H, boat-1-CH$_2$, $^3J_{HH}$=11.4 Hz) ppm.

$^{11}$B NMR (acetone-$d_6$): δ=-24.0 (s, 1B, BI),-14.3 (d, 2B, BH), -12.3 (d, 2B, BH), -9.1 (s, 3B, BH), -3.0 (d, 2B, BH) ppm.

$^{13}$C{$^1$H} NMR (acetone-$d_6$): 5=35.7 (s, 5-C$_q$), 38.9 (s, 2-CH), 63.2 (s, 1-CH$_2$), 68.1 (s, 3-C$_q$), 69.4 (s, 4-C$_q$) ppm.

Mass spectrometry (ESI neg., CH$_3$OH):
Calculated: m/z=402.1
Determined: m/z=401.1 (100%, [M-H]$^-$), 301.1 (15%, [M-C$_5$H$_9$O$_2$]$^-$).

IR spectroscopy (KBr, Q in cm$^{-1}$): 3,407 (s), 3,214 (s), 2,963 (s), 2,871 (m), 2,606 (s), 2,260 (w), 1,969 (w), 1,630 (w), 1,419 (m), 1,385 (m), 1,302 (w), 1,262 (m) 1,199 (m), 1,159 (m), 1,095 (s), 1,020 (s), 973 (w), 885 (w), 802 (s), 684 (w), 641 (w), 546 (w)

Embodiment 21

9-Iodo-1-(2-mercaptomethyl)naphthyl-7-(tetrahydro-2H-pyran-4-olyl)-1,7-dicarba-closo-dodecaborane (12)

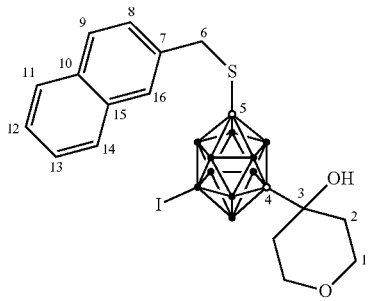

1.10 g (7.95 mmol, 4.0 eq.) of potassium carbonate is added to a solution of 9-iodo-1-mercapto-7-(tetrahydro-2H-pyran-4-olyl)-1,7-dicarba-closo-dodecaborane(12) (0.8 g, 1.99 mmol, 1.0 eq.) and 2-bromomethyl naphthalene (439.5 mg, 1.99 mmol, 1.0 eq.) in 80 ml of acetone at room temperature, and then heated under reflux for 24 hours. After being cooled to room temperature, the suspension is filtered, and the solvent is removed under reduced pressure. The raw product is purified by column chromatography (eluent: n-hexane/ethyl acetate 5:2 v/v). The product is obtained as a brownish oil.

Yield: 400.0 mg (0.74 mmol, 37%)

$R_f$ value: 0.38 (eluent: n-hexane/ethyl acetate 5:2 v/v)

$^1$H NMR (CDCl$_3$): δ=1.11-4.01 (br m, 9H, BH), 1.57 (d, 2H, seat-2-CH$_2$, $^3J_{HH}$=13.4 Hz), 1.80 (dt, 2H, boat-2-CH$_2$, $^3J_{HH}$=13.4 Hz), 3.64 (dt, 2H, seat-1-CH$_2$, $^3J_{HH}$=11.7 Hz), 3.78 (dd, 2H, boat-1-CH$_2$, $^3J_{HH}$=11.7 Hz), 4.14 (s, 2H, 6-CH$_2$), 7.38 (dd, 1H, 8-CH, $^3J_{HH}$=8.5 Hz), 7.46-7.51 (m, 2H, 12,13-CH), 7.74 (br s, 1H, 16-CH), 7.78-7.84 (m, 2H, 11, 14-CH) ppm.

$^{11}$B NMR (CDCl$_3$): δ=-24.1 (s, 1B, BI),-12.8 (d, 2B, BH), -9.6 (d, 2B, BH), -8.4 (d, 3B, BH), -3.9 (d, 2B, BH) ppm.

$^{13}$C{$^1$H} NMR (CDCl$_3$): δ=39.3 (s, 2-CH$_2$), 41.4 (s, 6-CH), 63.6 (s, 1-CH$_2$), 69.8 (s, 3-C$_q$), 72.4 (s, 5-C$_q$), 89.4 (s, 4-C$_q$), 126.4 (s, 12-CH), 126.5 (s, 13-CH), 126.8 (s, 8-CH), 127.7 (s, 11,14-CH), 128.4 (s, 9-CH), 128.7 (s, 16-CH), 131.1 (s, 7-C$_q$), 132.8 (s, 10-C$_q$), 133.2 (s, 15-C$_q$) ppm.

Mass spectrometry (ESI neg., CH$_3$OH):
Calculated: m/z=542.2
Determined: m/z=541.2 (100%, [M-H]$^-$).

IR spectroscopy (KBr, ṽ in cm$^{-1}$): 3,387 (s), 3,053 (m), 2,960 (s), 2,869 (s), 2,607 (s), 1,708 (m), 1,600 (w), 1,509 (m), 1,467 (w), 1,358 (m), 1,301 (m), 1,272 (m), 1,243 (s), 1,204 (w), 1,159 (s), 1,126 (s), 1,020 (m), 973 (w), 944 (w), 894 (w), 853 (m), 816 (s), 752 (s), 633 (w), 620 (w), 547 (m), 472 (m).

Embodiment 22

9-Iodo-1-(2-mercaptomethyl)quinolinyl-7-(tetrahydro-2H-pyran-4-olyl)-1,7-dicarba-closo-dodecaborane(12)

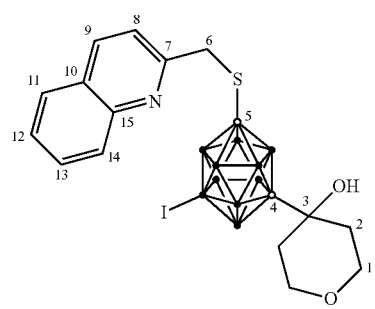

412 mg (2.99 mmol, 4.0 eq.) of potassium carbonate is added to a solution of 9-iodo-1-mercapto-7-(tetrahydro-2H-pyran-4-olyl)-1,7-dicarba-closo-dodecaborane(12) (0.3 g, 0.75 mmol, 1.0 eq.) and 2-chloromethyl quinoline hydrochloride (159.7 mg, 0.75 mmol, 1.0 eq.) in 50 ml of acetone at room temperature, and then heated under reflux for 24 hours. After being cooled to room temperature, the suspension is filtered, and the solvent is removed under reduced pressure. The raw product is purified by column chromatography (eluent: n-hexane/ethyl acetate 5:2 v/v). The product is obtained as a white solid.

Yield: 250 mg (0.46 mmol, 62%)

$R_f$ value: 0.10 (eluent: n-hexane/ethyl acetate 5:2 v/v)

$^1$H NMR (CDCl$_3$): δ=1.29-3.87 (br m, 9H, BH), 1.59 (d, 2H, seat-2-CH$_2$, $^3J_{HH}$=13.2 Hz), 1.75 (dt, 2H, boat-2-CH$_2$, $^3J_{HH}$=13.2 Hz), 3.61 (t, 2H, seat-1-CH$_2$, $^3J_{HH}$=12.1 Hz), 3.76 (dd, 2H, boat-1-CH$_2$, $^3J_{HH}$=12.1 Hz), 4.31 (s, 2H, 6-CH$_2$), 7.45 (d, 1H, 8-CH, $^3J_{HH}$=8.4 Hz), 7.54 (t, 1H, 12-CH, $^3J_{HH}$=7.6 Hz), 7.71 (t, 1H, 13-CH, $^3J_{HH}$=7.6 Hz), 7.81 (d, 1H, 11-CH, $^3J_{HH}$=8.4 Hz), 8.02 (d, 1H, 14-CH, $^3J_{HH}$=8.4 Hz), 8.15 (d, 1H, 9-CH, $^3J_{HH}$=8.4 Hz) ppm.

$^{11}$B NMR (CDCl$_3$): δ=−24.1 (s, 1B, BI),-14.5 (d, 1B, BH), −12.8 (d, 2B, BH), −9.6 (d, 2B, BH), −6.1 (d, 2B, BH), −4.7 (d, 2B, BH) ppm.

$^{13}$C{$^1$H} NMR (CDCl$_3$): δ=39.1 (s, 2-CH$_2$), 43.3 (s, 6-CH), 63.6 (s, 1-CH$_2$), 69.7 (s, 3-C$_q$), 72.0 (s, 5-C$_q$), 89.5 (s, 4-C$_q$), 120.6 (s, 8-CH), 126.8 (s, 12-CH), 127.1 (s, 10-C$_q$), 127.5 (s, 11-CH), 128.9 (s, 14-CH), 129.9 (s, 13-CH), 137.1 (s, 9-CH), 147.5 (s, 15-C$_q$), 155.0 (s, 7-C$_q$) ppm.

Mass spectrometry (ESI pos., CH$_3$OH):
Calculated: m/z=543.2
Determined: m/z=566.2 (100%, [M+Na]$^+$), 544.2 (30%, [M+H]$^+$).

IR spectroscopy (KBr, ṽ in cm$^{-1}$): 3,418 (s), 2,960 (m), 2,930 (m), 2,869 (m), 2,610 (s), 1,703 (w), 1,619 (w), 1,598 (m), 1,562 (w), 1,505 (m), 1,427 (m), 1,385 (m), 1,355 (m), 1,302 (w), 1,244 (m), 1,160 (s), 1,137 (s), 1,099 (m), 1,020 (w), 975 (w), 941 (w), 850 (w), 803 (m), 765 (m), 668 (w), 618 (w), 546 (w), 476 (w).

Embodiment 23

9-9-Iodo-1-mercaptocarbonylphenyl-7-(tetrahydro-2H-pyran-4-olyl)-1,7-dicarba-closo-dodecaborane (12)

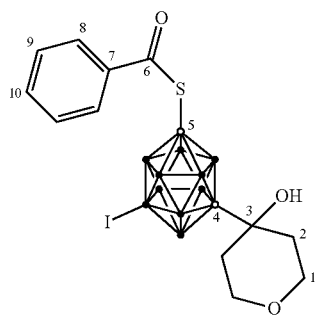

250.0 mg (0.62 mmol, 1.0 eq.) of 9-iodo-1-mercapto-7-(tetrahydro-2H-pyran-4-olyl)-1,7-dicarba-closo-dodecaborane(12) is dissolved in 30 ml of dichloromethane, to which 0.33 ml (1.86 mmol, 3.0 eq.) of diisopropylamine and then 72 μl (87 mg, 0.62 mmol, 1.0 eq.) of benzoyl chloride are added at room temperature. After 24 hours, 30 ml of distilled water is added to the obtained white suspension, which is acidulated by means of diluted hydrochloric acid, and the resultant phases are separated. The organic phase is washed twice by means of 20 ml of diluted hydrochloric acid on each occasion, neutralised by means of distilled water, and washed by means of saturated sodium chloride solution. The organic phase is dried by means of magnesium sulfate, and the solvent is removed under reduced pressure. The raw product is purified by column chromatography (eluent: n-hexane/ethyl acetate 5:2 v/v). The product is obtained as a colourless oil.

Yield: 80.0 mg (0.26 mmol, 25%)
R$_f$ value: 0.35 (eluent: n-hexane/ethyl acetate 5:2 v/v)

$^1$H NMR (CDCl$_3$): δ=1.04-4.07 (br m, 9H, BH), 1.61 (d, 2H, seat-2-CH$_2$, $^3J_{HH}$=13.2 Hz), 1.87 (dt, 2H, boat-2-CH$_2$, $^3J_{HH}$=13.2 Hz), 3.67 (t, 2H, seat-1-CH$_2$, $^3J_{HH}$=11.5 Hz), 3.82 (dd, 2H, boat-1-CH$_2$, $^3J_{HH}$=11.5 Hz), 7.46 (t, 2H, 8-CH, $^3J_{HH}$=7.6 Hz), 7.62 (t, 1H, 12-CH, $^3J_{HH}$=7.3 Hz), 7.81 (d, 2H, 13-CH, $^3J_{HH}$=7.6 Hz) ppm.

$^{11}$B NMR (CDCl$_3$): δ=−24.3 (s, 1B, BI),-14.6 (d, 2B, BH), −13.0 (d, 2B, BH), −9.9 (d, 3B, BH), −3.9 (d, 2B, BH) ppm.

$^{13}$C{$^1$H} NMR (CDCl$_3$): δ=39.2 (s, 2-CH$_2$), 63.6 (s, 1-CH$_2$), 66.3 (s, 5-C$_q$), 66.9 (s, 3-C$_q$), 89.3 (s, 4-C$_q$), 127.1 (s, 8-CH), 129.0 (s, 9-CH), 134.5 (s, 10-CH), 135.0 (s, 7-C$_q$), 184.9 (s, 6-C$_q$) ppm.

Mass spectrometry (ESI pos., CH$_3$OH):
Calculated: m/z=506.1
Determined: m/z=529.1 (100%, [M+Na]$^+$).

IR spectroscopy (KBr, ṽ in cm$^{-1}$): 3,427 (s), 2,967 (w), 2,870 (w), 2,610 (m), 1,696 (m), 1,580 (w), 1,467 (w), 1,448 (w), 1,385 (m), 1,302 (w), 1,244 (w), 1,201 (m), 1,177 (w), 1,159 (m), 1,130 (m), 1,098 (w), 1,021 (w), 974 (w), 940 (w), 888 (m), 850 (w), 804 (w), 769 (w), 683 (m), 668 (m), 641 (w), 546 (w).

Embodiment 24

9-Iodo-1-mercaptocarbonylphenyl-1,7-dicarba-closo-dodecaborane(12)

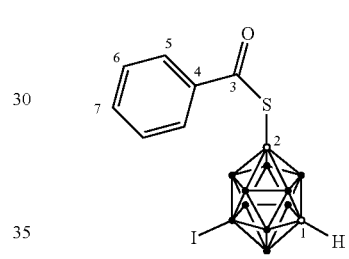

250.0 mg (0.83 mmol, 1.0 eq.) of 9-iodo-1-mercapto-1,7-dicarba-closo-dodecaborane(12) is dissolved in 30 ml of dichloromethane, to which 0.33 ml (1.86 mmol, 3.0 eq.) of diisopropylamine and then 72 μl (87 mg, 0.62 mmol, 1.0 eq.) of benzoyl chloride are added. After 24 hours, 30 ml of distilled water is added to the obtained white suspension, which is acidulated by means of diluted hydrochloric acid, and the resultant phases are separated. The organic phase is washed twice by means of 20 ml of diluted hydrochloric acid on each occasion, neutralised by means of distilled water, and washed by means of saturated sodium chloride solution. The organic phase is dried by means of magnesium sulfate, and the solvent is removed under reduced pressure. The raw product is purified by column chromatography (eluent: n-hexane/ethyl acetate 5:2 v/v). The product is obtained as a colourless oil.

Yield: 40 mg (0.1 mmol, 11%)
R$_f$ value: 0.83 (eluent: n-hexane/ethyl acetate 5:2 v/v)

$^1$H NMR (CDCl$_3$): δ=1.17-4.24 (br m, 9H, BH), 3.16 (s, 1H, 1-CH), 7.47 (t, 2H, 6-CH, $^3J_{HH}$=8.1 Hz), 7.62 (t, 1H, 7-CH, $^3J_{HH}$=7.7 Hz), 7.82 (d, 2H, 5-CH, $^3J_{HH}$=8.1 Hz) ppm.

$^{11}$B NMR (CDCl$_3$): δ=−24.0 (s, 1B, BI),-15.6 (d, 2B, BH), −12.6 (d, 2B, BH), −8.1 (d, 3B, BH), −2.1 (d, 2B, BH) ppm.

$^{13}$C{$^1$H} NMR (CDCl$_3$): b=56.5 (s, 1-CH), 77.2 (s, 2-C$_q$), 127.2 (s, 5-CH), 129.1 (s, 6-CH), 134.5 (s, 7-CH), 135.1 (s, 4-C$_q$), 184.9 (s, 3-CH) ppm.

Mass spectrometry (ESI pos., CH$_3$OH):
Calculated: m/z=406.1
Determined: m/z=429.1 (100%, [M+Na]$^+$).

IR spectroscopy (KBr, Q̃ in cm$^{-1}$): 3,053 (m), 2,942 (w), 2,608 (s), 1,697 (s), 1,596 (w), 1,581 (w), 1,448 (m), 1,385 (w), 1,202 (s), 1,178 (m), 1,130 (w), 1,075 (w), 1,000 (w), 931 (w), 888 (s), 806 (m), 769 (m), 786 (w), 684 (s), 641 (m), 615 (w).

Comparative Examples

Comparative Example 1

1-(Quinolin-2-ylmethoxy)-1,7-dicarba-closo-dodecaborane(12)

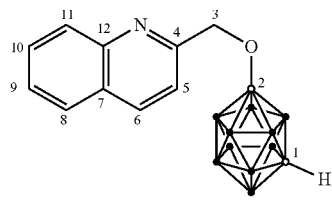

300 mg (1.87 mmol, 1.0 eq.) of 1-hydroxy-1,7-dicarba-closo-dodecaborane(12) and 415 mg (1.87 mmol, 1.0 eq.) of 2-(bromomethyl)quinoline are dissolved in 30 ml of acetone, to which 0.78 g (5.61 mmol, 3.0 eq.) of potassium carbonate is added at room temperature and which is then heated under reflux for 24 hours. The obtained suspension is cooled to room temperature, to which 20 ml of distilled water and 10 ml of saturated sodium chloride solution are added. Extraction is carried out three times by means of 20 ml of diethyl ether on each occasion, the combined organic phases are dried by means of magnesium sulfate, and the solvent is removed under reduced pressure. The residue is applied to silica gel and purified by column chromatography (eluent: n-hexane/ethyl acetate 5:1 v/v). A colourless solid is obtained.

Yield: 0.43 g (1.42 mmol, 76%)

$R_f$ value: 0.47 (eluent: n-hexane/ethyl acetate 5:1 v/v)

Melting point: 121.0-122.0° C.

$^1$H NMR (CDCl$_3$): δ=1.22-3.74 (br m, 10H, BH), 2.84 (br s, 1H, 1-CH), 4.86 (s, 2H, 3-CH$_2$), 7.47 (d, 1H, 5-CH, $^3J_{HH}$=8.4 Hz), 7.55 (t, 1H, 9-CH, $^3J_{HH}$=8.2 Hz), 7.73 (t, 1H, 10-CH, $^3J_{HH}$=8.2 Hz), 7.81 (d, 1H, 8-CH, $^3J_{HH}$=8.2 Hz), 8.02 (d, 1H, 11-CH, $^3J_{HH}$=8.7 Hz), 8.17 (d, 1H, 6-CH, $^3J_{HH}$=8.4 Hz) ppm.

$^{11}$B{$^1$H} NMR (CDCl$_3$): δ=−16.1 (s, 4B), −15.0 (s, 1B), −13.3 (s, 2B), −12.3 (s, 2B), −5.9 (s, 1 B) ppm.

$^{13}$C{$^1$H} NMR (CDCl$_3$): δ=50.7 (s, 1-CH), 76.6 (s, 3-CH$_2$), 107.0 (s, 2-C$_q$), 119.0 (s, 5-CH), 126.7 (s, 9-CH), 127.6 (s, 8-CH), 128.1 (s, 7-C$_q$), 128.9 (s, 11-CH), 129.9 (s, 10-CH), 137.0 (s, 6-CH), 147.3 (s, 12-C$_q$), 156.1 (s, 4-C$_q$) ppm.

Mass spectrometry (ESI pos., acetone):

Calculated: m/z=301.2

Determined: m/z=302.3 (100%, [M+H]$^+$).

IR spectroscopy (KBr, Q̃ in cm$^{-1}$): 3,445 (m), 2,977 (s), 2,624 (s), 2,603 (s), 2,570 (s), 1,601 (m), 1,507 (m), 1,448 (m), 1,428 (m), 1,216 (s), 1,051 (s), 1,009 (m), 821 (s), 780 (m), 745 (m), 727 (m), 621 (w), 473 (w), 437 (w).

Elementary Analysis:

Calculated for C$_{12}$H$_{19}$B$_{10}$N$_1$O$_1$: C=47.82% H=6.35% N=4.65%.

Found: C=47.23% H=6.42% N=4.31%.

Comparative Example 2

1-(Quinolin-2-ylmethyl)thio-1,7-dicarba-closo-dodecaborane(12)

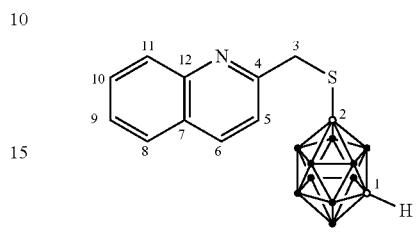

300 mg (1.68 mmol, 1.0 eq.) of 1-mercapto-1,7-dicarba-closo-dodecaborane(12) and 373 mg (1.68 mmol, 1.0 eq.) of 2-(bromomethyl)quinoline are dissolved in 30 ml of acetone, to which 0.70 g (5.04 mmol, 3.0 eq.) of potassium carbonate is added at room temperature and which is then heated under reflux for 24 hours. The obtained suspension is cooled to room temperature, to which 20 ml of distilled water and 10 ml of saturated sodium chloride solution are added. Extraction is carried out three times by means of 20 ml of diethyl ether on each occasion, the combined organic phases are dried by means of magnesium sulfate, and the solvent is removed under reduced pressure. The residue is applied to silica gel and purified by column chromatography (eluent: n-hexane/ethyl acetate 5:1 v/v). A yellowish liquid is obtained.

Yield: 0.42 g (1.32 mmol, 79%)

$R_f$ value: 0.63 (eluent: hexane/ethyl acetate 5:1 v/v)

Melting point: 127.0-128.0° C.

$^1$H NMR (acetone-d$_6$): δ=1.50-3.55 (br m, 10H, BH), 3.79 (br s, 1H, 1-CH), 4.43 (s, 2H, 3-CH$_2$), 7.60 (t, 1H, 9-CH, $^3J_{HH}$=7.2 Hz), 7.61 (d, 1H, 5-CH, $^3J_{HH}$=8.4 Hz), 7.77 (t, 1H, 10-CH, $^3J_{HH}$=8.6 Hz), 7.95 (d, 1H, 8-CH, $^3J_{HH}$=8.1 Hz), 8.00 (d, 1H, 11-CH, $^3J_{HH}$=8.6 Hz), 8.32 (d, 1H, 6-CH, $^3J_{HH}$=8.4 Hz) ppm.

$^{11}$B{$^1$H} NMR (acetone-d$_6$): δ=−14.3 (s, 2B), −13.3 (s, 2B), −10.7 (s, 3B), −10.1 (s, 2B), −3.5 (s, 1B) ppm.

$^{13}$C{$^1$H} NMR (acetone-d$_6$): δ=42.8 (s, 3-CH$_2$), 56.5 (s, 1-CH), 72.6 (s, 2-C$_q$), 120.9 (s, 5-CH), 126.6 (s, 9-CH), 127.1 (s, 7-C$_q$), 127.7 (s 8-CH), 128.7 (s, 11-CH), 129.7 (s, 10-CH), 136.8 (s, 6-CH), 147.5 (s, 12-C$_q$), 155.9 (s, 4-C$_q$) ppm.

Mass spectrometry (ESI pos., CHCl$_3$/CH$_3$OH):

Calculated: m/z=317.2

Determined: m/z=340.2 (100%, [M+Na]$^+$), 318.2 (20%, [M+H]$^+$).

IR spectroscopy (KBr, ṽ in cm$^{-1}$): 3,428 (s), 2,625 (s), 2,602 (s), 2,590 (s), 1,598 (m), 1,505 (m), 1,427 (m), 1,262 (w), 1,122 (w), 1,084 (w), 877 (w), 840 (w), 802 (w), 770 (m), 729 (w), 618 (w), 498 (w), 472 (w).

Elementary Analysis:

Calculated for C$_{12}$H$_{19}$B$_{10}$N$_1$S$_1$: C=45.40% H=6.03% N=4.41%.

Found: C=45.69% H=6.03% N=4.29%.

Comparative Example 3

1-Quinolin-2-ylmethoxy-1,12-dicarba-closo-dodecaborane(12)

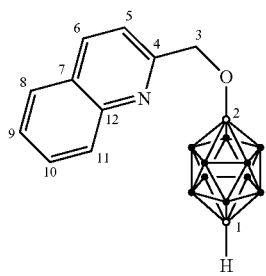

300 mg (1.87 mmol, 1.0 eq.) of 1-hydroxy-1,12-dicarba-closo-dodecaborane(12) and 415 mg (1.87 mmol, 1.0 eq.) of 2-(bromomethyl)quinoline are dissolved in 30 ml of acetone, to which 0.78 g (5.61 mmol, 3.0 eq.) of potassium carbonate is added at room temperature and which is then heated under reflux for 24 hours. The obtained suspension is cooled to room temperature and filtered. The combined organic phases are dried by means of magnesium sulfate, and the solvent is removed under reduced pressure. The residue is applied to silica gel and purified by column chromatography (eluent: hexane/ethyl acetate 5:1 v/v). A colourless solid is obtained.

Yield: 0.40 g (1.38 mmol, 74%)
$R_f$ value: 0.43 (eluent: hexane/ethyl acetate 10:1 v/v)
Melting point: 110.3-111.2° C.

$^1$H NMR (CDCl$_3$): δ=1.20-3.30 (br m, 10H, BH), 2.56 (br s, 1H, 1-CH), 4.67 (s, 2H, 3-CH$_2$), 7.37 (d, 1H, 5-CH, $^3J_{HH}$=8.5 Hz), 7.53 (t, 1H, 9-CH, $^3J_{HH}$=8.0 Hz), 7.70 (t, 1H, 10-CH, $^3J_{HH}$=8.5 Hz), 7.79 (d, 1H, 8-CH, $^3J_{HH}$=8.0 Hz), 7.99 (d, 1H, 11-CH, $^3J_{HH}$=8.5 Hz), 8.15 (d, 1H, 6-CH, $^3J_{HH}$=8.5 Hz) ppm.

$^{11}$B{$^1$H} NMR (CDCl$_3$): δ=−13.6 (s, 2B), −17.4 (s, 5B), −13.7 (s, 5B) ppm.

$^{13}$C{$^1$H} NMR (CDCl$_3$): δ=50.2 (s, 1-CH), 75.6 (s, 3-CH$_2$), 113.9 (s, 2-C$_q$), 118.9 (s, 5-CH), 126.5 (s, 9-CH), 127.5 (s, 7-C$_q$), 127.6 (s, 8-CH), 128.7 (s-11-CH), 129.7 (s, 10-CH), 137.1 (s, 6-CH), 147.1 (s, 12-C$_q$), 156.3 (s, 4-C$_q$) ppm.

Mass spectrometry (ESI pos., CH$_2$Cl$_2$/CH$_3$OH):
Calculated: m/z=301.2
Determined: m/z=302.3 (100%, [M+H]$^+$), 324.2 (10%, [M+Na]$^+$).

IR spectroscopy (KBr, Q in cm$^{-1}$): 3,387 (s), 2,957 (s), 2,928 (s), 2,859 (m), 2,602 (s), 1,461 (w), 1,253 (w), 1,137 (s), 842 (m), 732 (w).

Elementary Analysis:
Calculated for C$_{18}$H$_{28}$B$_{10}$O$_2$S$_1$: C=51.90% H=6.77%.
Found: C=53.23% H=6.92%.

Solubility Tests

Solubility tests in ethanol and DMSO were carried out to determine the solubility. The amount of solvent required to obtain a clear solution was added to 4 mg of the compounds in an Eppendorf tube. The concentration of the solution was then determined on the basis of the mass of the compounds and the amount of solvent. The results of the tests are shown in Table 1.

TABLE 1

| Molecule | Embodiment | Solubility in EtOH | Solubility in DMSO |
|---|---|---|---|
| Solubility behaviour | | | |
| (quinoline-CH$_2$-O-carborane-(CH$_2$)$_n$-OH structure) | 3 | 86.8 mmol/l | 208.3 mmol/l |
| (quinoline-CH$_2$-S-carborane-(CH$_2$)$_n$-OH structure) | 5 | 238.5 mmol/l | 953.9 mmol/l |

• = BH
o = C

TABLE 1-continued
| | | Solubility behaviour | |
|---|---|---|---|
| Molecule | Embodiment | Solubility in EtOH | Solubility in DMSO |
| 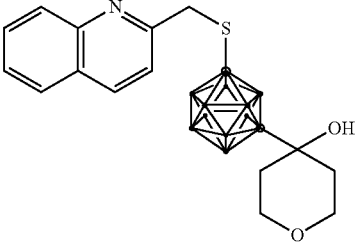<br>● = BH<br>○ = C | 8 | 155 mmol/l | 619 mmol/l |
| 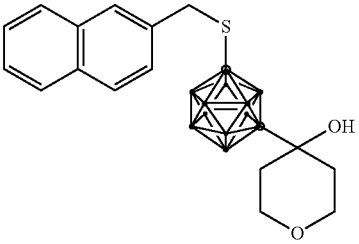<br>● = BH<br>○ = C | 9 | 76 mmol/l | 228 mmol/l |
| 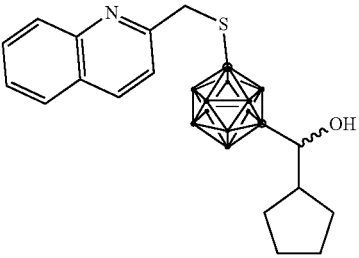<br>● = BH<br>○ = C | 12 | 57.7 mmol/l | 144.4 mmol/l |
| 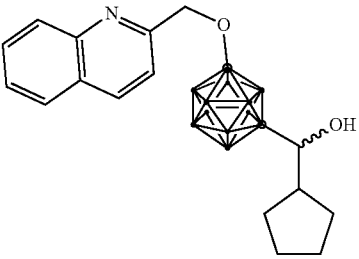<br>● = BH<br>○ = C | 14 | 38.9 mmol/l | 87.6 mmol/l |

TABLE 1-continued

Solubility behaviour

| Molecule | Embodiment | Solubility in EtOH | Solubility in DMSO |
|---|---|---|---|
| [structure: quinoline-CH₂-S-carborane-CH(OH)-cyclopentyl]<br>● = BH<br>○ = C | 16 | 24.06 mmol/l | 132.3 mmol/l |
| [structure: quinoline-CH₂-O-carborane-CH(OH)-cyclopentyl]<br>● = BH<br>○ = C | 18 | 21.2 mmol/l | 91.8 mmol/l |
| [structure: methylsulfonylphenyl-pyrazole-phenyl-CH₂-S-carborane-tetrahydropyran-OH]<br>● = BH<br>○ = C | 19 | 204.50 mmol/l | 409.00 mmol/l |
| [structure: quinoline-CH₂-O-carborane-H]<br>● = BH<br>○ = C | 1 | 72 mmol/l | 432 mmol/l |

TABLE 1-continued

Solubility behaviour

| Molecule | Embodiment | Solubility in EtOH | Solubility in DMSO |
|---|---|---|---|
| 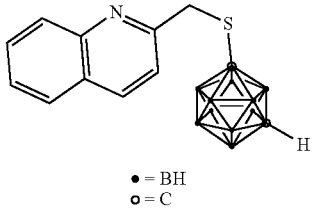 | 2 | 67 mmol/l | 600 mmol/l |

● = BH
○ = C

Inhibition Test

In order to determine the inhibiting effect, $IC_{50}$ tests were carried out on the compounds from embodiments 3, 5, 8 and 9 and comparative examples 1 and 2 in comparison with reference Rev-5901.

The 5-LOX activity of the cells was established on the basis of the concentration of inhibitor.

In this process, intact polymorphonuclear leukocytes were isolated from blood as specified in the known literature [C. Greiner et al., British Journal of Pharmacology, 2011, 164, 781-793]. The cells were grown on cell sheets until a confluence of 95% was reached, i.e. 95% of the cell sheets was covered with cells. Each cell sheet was then treated with 10 µl of a solution of the inhibitor at concentrations of 0.05 µM, 0.1 µM, 0.5 µM, 1 µM, 5 µM, 10 µM, 50 µM and 100 µM at 37° C. for 15 minutes. Each cell sheet was then treated with an arachidonic acid solution for 10 minutes. 10 µl of a 1:1 mixture of 2 mM of arachidonic acid and 250 µM of A23187 $Ca^{2+}$-ionophore solution in ethanol was used for this. Using HPLC, it was then checked how much arachidonic acid had been converted by the enzyme in comparison with a sample without inhibitor.

Conversion of a small amount of arachidonic acid is evidence of a strong inhibiting effect.

The concentration of inhibitor at which only 50% of the arachidonic acid is converted is referred to as the $IC_{50}$ value (i.e. the enzyme has been inhibited by 50%). The $IC_{50}$ values for each compound are shown in Table 2.

TABLE 2

Results of the inhibition tests

| Compound/embodiment | $IC_{50}$ value (at concentration) |
|---|---|
| Rev-5901 | 0.58 µM |
| 3 | 1.4 µM |
| 5 | 2.5 µM |
| 8 | 3.8 µM |
| 9 | 5.1 µM |
| Compound/comparative example | |
| Rev-5901 | 0.58 µM |
| 1 | 2.3 µM |
| 2 | 5.8 µM |

It can be clearly seen that all the compounds shown are able to effectively inhibit enzyme system 5-LOX-FLAP. The $IC_{50}$ values of all cluster analogues are in the range of the reference.

Figure 1:
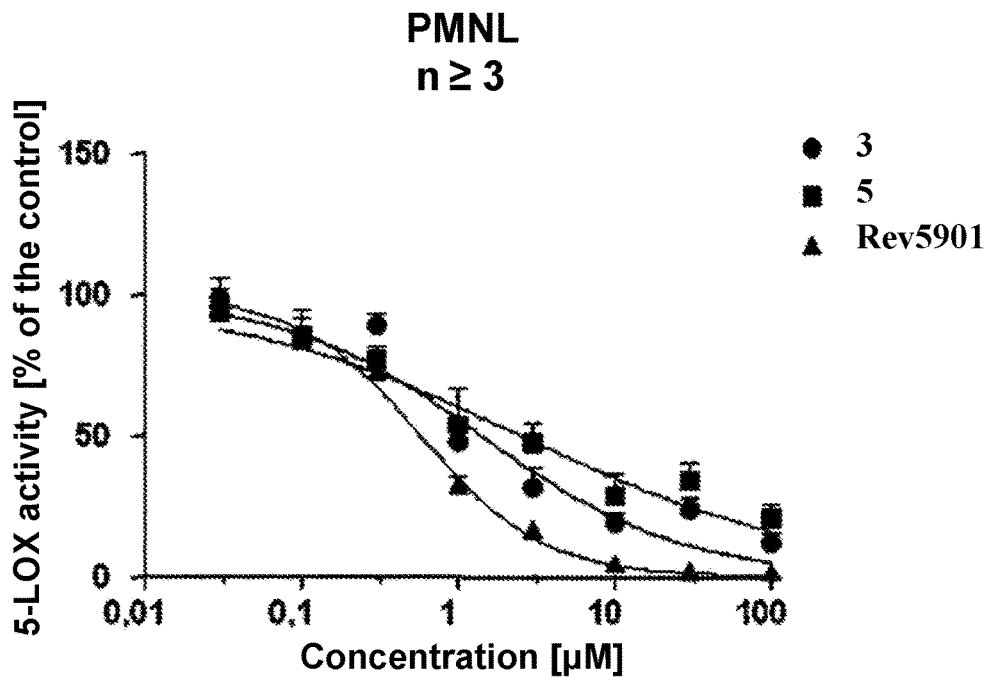
FIG. 1 is a graph illustrating inhibition test results where enzyme activity was plotted with respect to the concentration of the corresponding inhibitor.
Figure 2:
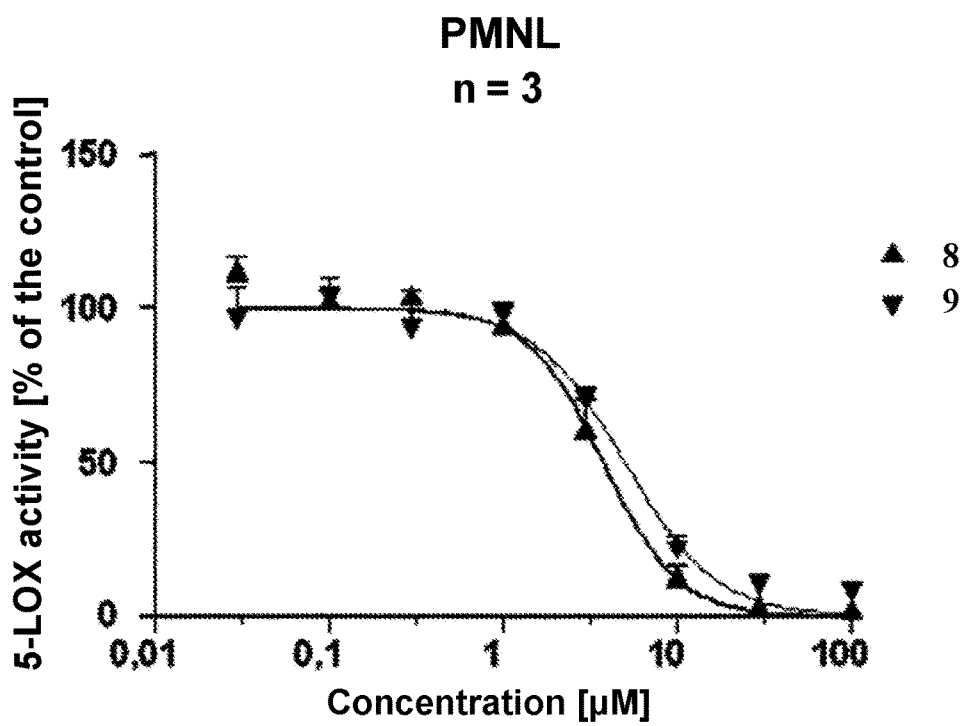
FIG. 2 is a graph illustrating inhibition test results where enzyme activity was plotted with respect to the concentration of the corresponding inhibitor.
Figure 3:
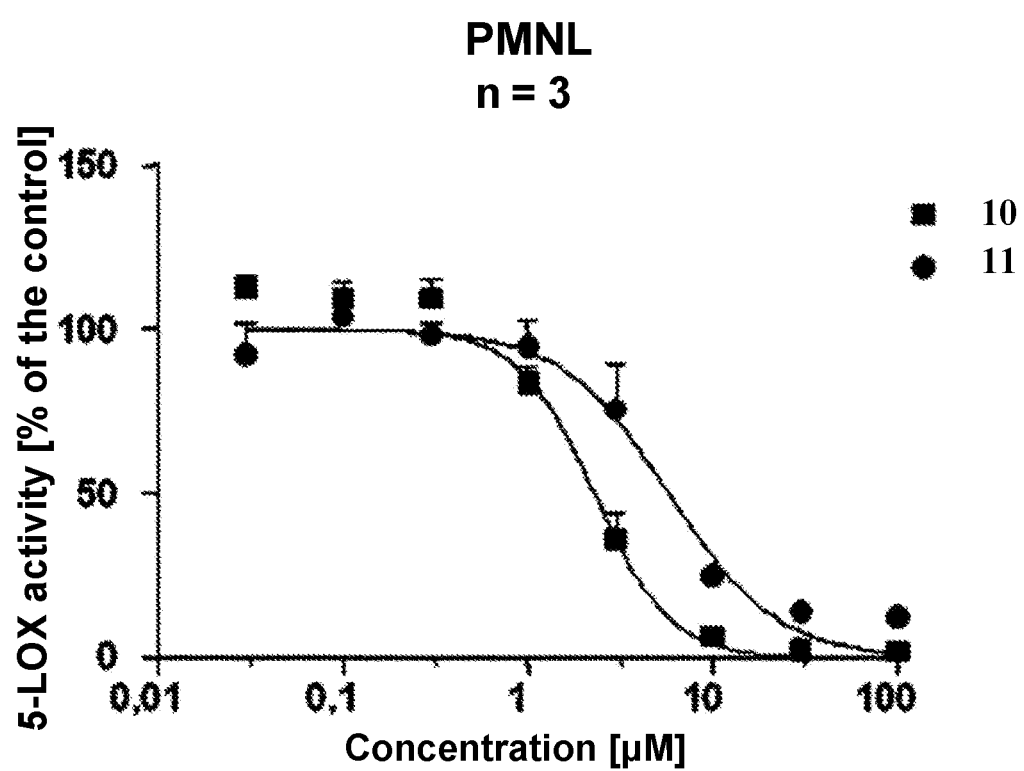
FIG. 3 is a graph illustrating inhibition test results where enzyme activity was plotted with respect to the concentration of the corresponding inhibitor.

The results of the inhibition tests are shown as graphs in FIG. 1 to FIG. 3. In these graphs, the enzyme activity was plotted with respect to the concentration of the corresponding inhibitor.

In FIG. 1, the enzyme activity values are plotted with respect to the concentration of the inhibitors from embodiment 3 (symbol: ●) and 5 (symbol: ▲) and inhibitor Rev-5901 (symbol: ■).

In FIG. 2, the enzyme activity values are plotted with respect to the concentration of the inhibitors from embodiment 8 (symbol: ▲) and 9 (symbol: ▼).

In FIG. 3, the enzyme activity values are plotted with respect to the concentration of the inhibitors from comparative example 1 (symbol: ■) and 2 (symbol: ●).

It can be seen from the curves that the inhibitors halve the activity of the enzyme system at a concentration of 1-6 µM, and even completely inhibit said system at a higher concentration. Embodiments 3 (FIG. 1) and comparative example 1 (FIG. 3), which inhibit the system by 50% at 1.4 and 2.3 µM, respectively, stand out in particular. What is notable about comparative example 1 is that it is a very small, only mono-functionalised compound which nevertheless has a very effective enzyme-inhibiting effect. Comparative examples 1 and 2 even exhibit an improved inhibiting effect in comparison with the phenyl-substituted LOX inhibitors known from the literature. However, the cytotoxicity tests show that this is not sufficient for having a cytotoxic effect on various cancer cell lines.

Cytotoxicity Tests

In order to determine the cytotoxicity towards various cancer cell lines, MTT and crystal violet (CV) assays were carried out. The MTT essay takes place as specified by T. Mosmann [T. Mosmann, J. Immunol. Methods, 1983, 65, 55], and the CV test takes place as specified by D. A. Flick et al. [D. A. Flick, G. E. Gifford, J. Immunol. Methods, 1984, 68, 167].

In order to determine the selective cytotoxicity of the contained compounds from embodiments 3, 5, 8 and 9 and comparative examples 1 and 2, tests were carried out on cancer cell lines and primary fibroblasts (MRC-5), which were isolated from human lung tissue, in comparison with reference compound Rev-5901. In these tests, the percentage of dead cells was analysed on the basis of the concentration of the inhibitors. The obtained $IC_{50}$ value indicates the concentration of a particular inhibitor at which 50% of the analysed cells die off.

The proportion of living cells was determined by the MTT assay (3-(4,5-dimethylthiazolyl-2)-2,5-diphenyltetrazolium-bromide) and the crystal violet (CV) assay. In the MTT assay, the presence of NADH and NADPH is established.

These two compounds are characteristic metabolism products in a functioning respiratory chain. NADH and NADPH reduce the MTT dye, thus leading to a change in colour, which can be measured and is thus directly proportional to the number of living cells.

Meanwhile, in the crystal violet assay, the crystal violet dye can only diffuse through the perforated cell membranes of dead cells. In this case, the number of dyed cells represents the number of dead cells.

Three skin cancer cell lines (A375, B16, B16F10) and three colon cancer cell lines (CT26CL25, HCT116, SW480) were analysed. Primary fibroblasts from human lung tissue (MRC-5) were used as an example of healthy cells and thus as a negative control. The results are shown in Tables 3a to 3c.

Results of the Cytotoxicity Tests

TABLE 3a

| Molecule | Embodiment | $IC_{50}$ MRC-5 | $IC_{50}$ A375 | $IC_{50}$ B16 | $IC_{50}$ HCT116 | $IC_{50}$ CT26CL25 | $IC_{50}$ SW480 |
|---|---|---|---|---|---|---|---|
| Rev-5901 | — | 70.10 μM | 25 μM | 27.57 μM | 50 μM | 28.05 μM | 50 μM |
| Reference substance | — | — | 46.45 μM | 44.95 μM | 50 μM | >50 μM | >50 μM |
| [structure] | 3 | >100 | 8.8 μM<br>26.9 μM | 45.7 μM<br>46 μM | 50 μM<br>>50 μM | 35 μM<br>50 μM | 29 μM<br>50 μM |
| [structure] | 5 | 82.0<br>30.5 μM | 8 μM<br>>50 μM | 50 μM<br>>50 μM | 45 μM<br>50 μM | 46 μM<br>50 μM | 33.1 μM<br>>50 μM |
| [structure] | 8 | 4.7 μM<br>8.7 μM | 30.7 μM<br>44.3 μM | 28 μM<br>39.8 μM | 10.8 μM<br>18.6 μM | 8.5 μM<br>9.9 μM |

● = BH
○ = C

The top value for each cell represents the IC$_{50}$ value in the MTT assay, and the bottom value represents the IC$_{50}$ value in the CV assay (crystal violet).

TABLE 3b

| Molecule | Embodiment | IC$_{50}$ MRC-5 | IC$_{50}$ A375 | IC$_{50}$ B16 | IC$_{50}$ HCT116 | IC$_{50}$ CT26CL25 | IC$_{50}$ SW480 |
|---|---|---|---|---|---|---|---|
| [structure: naphthyl-CH$_2$-S-carborane-C(OH)-tetrahydropyran] ● = BH, ○ = C | 9 | 42.4 µM >50 µM | 50 µM >50 µM | 50 µM 50 µM | 21.4 µM 22.4 µM | 28 µM 40 µM | |
| [structure: methylsulfonyl-phenyl-pyrazole(phenyl)-CH$_2$-S-carborane-C(OH)-tetrahydropyran] ● = BH, ○ = C | 19 | 10.4-11.8 µM 15.1-17.8 µM | | | | 10.8-12.5 µM 25.8-28.6 µM | |

The top value for each cell represents the IC$_{50}$ value in the MTT assay, and the bottom value represents the IC$_{50}$ value in the CV assay (crystal violet).

TABLE 3c

| Molecule | Comparative example | IC$_{50}$ MRC-5 | IC$_{50}$ A375 | IC$_{50}$ B16 | IC$_{50}$ HCT116 | IC$_{50}$ CT26-CL25 | IC$_{50}$ SW480 |
|---|---|---|---|---|---|---|---|
| Rev-5901 | — | 70.10 µM | 25 µM | 27.57 µM | 50 µM | 28.05 µM | 50 µM |
| | Reference substance | — | 46.45 µM | 44.95 µM | 50 µM | >50 µM | >50 µM |
| [structure: quinoline-CH$_2$-O-carborane-H] ● = BH, ○ = C | 1 | 50 µM >50 µM | 47.4 µM 47.6 µM | >50 µM 50 µM | >50 µM >50 µM | >50 µM >50 µM | >50 µM >50 µM |

TABLE 3c-continued

| Molecule | Comparative example | IC$_{50}$ MRC-5 | IC$_{50}$ A375 | IC$_{50}$ B16 | IC$_{50}$ HCT116 | IC$_{50}$ CT26-CL25 | IC$_{50}$ SW480 |
|---|---|---|---|---|---|---|---|
| 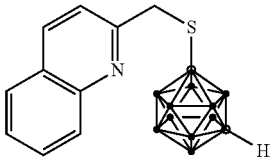 | 2 | 30 μM<br>34.8 μM | >50 μM<br>>50 μM | >50 μM<br>>50 μM | >50 μM<br>>50 μM | 50 μM<br>>50 μM |

● = BH
○ = C

The top value for each cell represents the IC$_{50}$ value in the MTT assay, and the bottom value represents the IC$_{50}$ value in the CV assay (crystal violet).

The invention claimed is:

1. A chemical compound of general structure

[A-A$_3$-X—R$_4$]

where
A=[R$_1$-R$_2$] or [R$_1$]
R$_1$=quinoline or naphthyl
R$_2$=alkyl
R$_3$=O, S, or NH
X=closo- or nido-boron cluster
R$_4$=

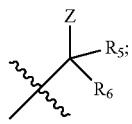

where Z=OH, SH, NH$_2$ or an amino, thio, or hydroxy group that is esterified or etherified by a group that is different from A;
where R$_5$ is selected from H, alkyl, aryl, heteroaryl, alkyl ether, alkyl thioether, or alkylamine;
where R$_6$ is selected from alkyl, aryl, heteroaryl, alkyl ether, alkyl thioether, or alkylamine;
where R$_5$ and R$_6$ may form a tetrahydropyranyl unit; and
where R$_3$ and R$_4$ are in meta or para positions in relation to one another.

2. A chemical compound according to claim 1, wherein R$_1$ is a quinoline substituent.

3. A chemical compound according to claim 1, wherein R$_5$ and R$_6$ form a tetrahydropyranyl unit.

4. A chemical compound according to claim 1, wherein Z is esterified or etherified by a group that is different from A.

5. A chemical compound according to claim 1, wherein X is selected from C$_2$B$_8$H$_{10}$, C$_2$B$_{10}$H$_{12}$, Si$_2$B$_{10}$H$_{12}$, P$_2$B$_{10}$H$_{10}$, SB$_{11}$H$_{11}$, NB$_{11}$H$_{11}^{(-)}$, PB$_{11}$H$_{11}^{(-)}$, CB$_6$H$_7^{(-)}$, CB$_7$H$_8^{(-)}$, CB$_9$H$_{10}^{(-)}$, CB$_9$H$_{12}^{(-)}$, CB$_{10}$H$_{11}^{(-)}$, CB$_{11}$H$_{12}^{(-)}$, SiB$_{11}$H$_{12}^{(-)}$, CB$_{11}$H$_{11}^{(2-)}$, SiB$_{11}$H$_{11}^{(2-)}$, SnB$_{11}$H$_{11}^{(2-)}$, GeB$_{11}$H$_{11}^{(2-)}$, C$_2$B$_9$H$_{12}$, C$_2$B$_9$H$_{12}^{(-)}$, C$_2$B$_9$H$_{11}^{(2-)}$, R$_a$C$_3$B$_n$H$_{n+3-a}^{(-)}$, RC$_2$B$_n$H$_{n+2-a}^{(-)}$, C$_3$B$_8$H$_{11}^{(-)}$, R$_2$C$_3$B$_8$H$_9^{(-)}$, C$_2$B$_9$H$_{11}^{(-)}$, or R$_2$C$_2$B$_9$H$_9^{(-)}$ (where R=H, alkyl, aryl, silyl).

6. A chemical compound according to claim 1, wherein at least one BH unit is substituted by a radiolabelled B-halogen unit.

7. A method for preparing a chemical compound of general formula

[A-R$_3$—X—R$_4$]

where
A=[R$_1$-R$_2$] or [R$_1$]
R$_1$=quinoline or naphthyl
R$_2$=alkyl
R$_3$=O, S, or NH
X=closo- or nido-boron cluster
R$_4$

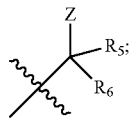

where Z=OH, SH, NH$_2$ or an amino, thio, or hydroxy group that is esterified or etherified by a group that is different from A;
where R$_5$ is selected from H, alkyl, aryl, heteroaryl, alkyl ether, alkyl thioether, or alkylamine;
where R$_6$ is selected from alkyl, aryl, heteroaryl, alkyl ether, alkyl thioether, or alkylamine;
where R$_5$ and R$_6$ may form a tetrahydropyranyl unit; and
where R$_3$ and R$_4$ are in meta or para positions in relation to one another,
comprising the steps of:
a) hydroxyalkylating or thioalkylating or aminoalkylating the cluster X,
b) hydroxylating or thiolating or aminating the boron-containing cluster X,
so as to form an intermediate compound of general formula [H—R$_3$—X—R$_4$]
where
R$_3$=O, S, or NH
X=closo- or nido-boron cluster
R$_4$=

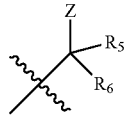

where Z=OH, SH, NH$_2$ or an amino, thio, or hydroxy group that is esterified or etherified by a group that is different from A;

where $R_5$ is selected from H, alkyl, aryl, heteroaryl, alkyl ether, alkyl thioether, or alkylamine;

where $R_6$ is selected from alkyl, aryl, heteroaryl, alkyl ether, alkyl thioether, or alkylamine;

where $R_5$ and $R_6$ may form a tetrahydropyranyl unit; and where $R_3$ and $R_4$ are in meta or para positions in relation to one another, c) selectively etherifying or esterifying H—$R_3$ in order to introduce A, wherein steps a) and b) can be interchanged as desired.

8. A method of inhibiting or modulating lipoxygenases in an individual, said method comprising the step of administering an effective dose of one or more chemical compounds according to claim 1 or a salt thereof to an individual requiring said dose for inhibiting or modulating lipoxygenases.

9. A pharmaceutical composition containing one or more compounds according to claim 1 or salts thereof, in conjunction with a pharmaceutically acceptable carrier.

10. A chemical compound according to claim 1, wherein $R_1$ is a naphthyl substituent.

11. A chemical compound according to claim 1, wherein Z is OH or a hydroxy group that is esterified or etherified by a group that is different from A.

12. A chemical compound according to claim 1, wherein the chemical compound is 1-(2-mercaptomethyl)quinolyl-7-(tetrahydro-2H-pyran-4-olyl)-1,7-dicarba-closo-dodecaborane.

* * * * *